United States Patent
Doulatov et al.

(10) Patent No.: US 11,980,620 B2
(45) Date of Patent: May 14, 2024

(54) COMPOUNDS AND METHODS FOR TREATMENT OF DIAMOND BLACKFAN ANEMIA

(71) Applicant: THE CHILDREN'S MEDICAL CENTER CORPORATION, Boston, MA (US)

(72) Inventors: Sergei Doulatov, Seattle, WA (US); George Q. Daley, Cambridge, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 339 days.

(21) Appl. No.: 16/620,064

(22) PCT Filed: Jun. 8, 2017

(86) PCT No.: PCT/US2017/036520
§ 371 (c)(1),
(2) Date: Dec. 6, 2019

(87) PCT Pub. No.: WO2018/226230
PCT Pub. Date: Dec. 13, 2018

(65) Prior Publication Data
US 2020/0188402 A1    Jun. 18, 2020

(51) Int. Cl.
| | |
|---|---|
| *A61K 31/517* | (2006.01) |
| *A61P 3/00* | (2006.01) |
| *A61P 7/06* | (2006.01) |
| *C12N 5/0789* | (2010.01) |
| *C12N 15/86* | (2006.01) |
| *G01N 33/50* | (2006.01) |
| *A61K 45/06* | (2006.01) |

(52) U.S. Cl.
CPC .............. *A61K 31/517* (2013.01); *A61P 3/00* (2018.01); *A61P 7/06* (2018.01); *C12N 5/0647* (2013.01); *C12N 15/86* (2013.01); *G01N 33/5047* (2013.01); *A61K 45/06* (2013.01)

(58) Field of Classification Search
None
See application file for complete search history.

(56) References Cited

U.S. PATENT DOCUMENTS

| | | |
|---|---|---|
| 2008/0033000 A1 | 2/2008 | Chang et al. |
| 2015/0265627 A1 | 9/2015 | Zon et al. |
| 2015/0329498 A1 | 11/2015 | Romero et al. |

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Doulatov et al., "Drug discovery for Diamond-Blackfan anemia using reprogrammed hematopoietic progenitors", Science Translational Medicine 9(376):eaah5645 (2017).

* cited by examiner

*Primary Examiner* — Po-Chih Chen
(74) *Attorney, Agent, or Firm* — NIXON PEABODY LLP; David S. Resnick; Jeanne Jodoin

(57) ABSTRACT

The present invention relates generally to methods for treatment of ribosomal disorders and ribosomopathy, e.g. Diamond Blackfan anemia (DBA). In some embodiments, the invention relates to methods for the use of a small-molecule autophagy modulator for treatment of ribosomal disorders and ribosomopathy. The invention also relates to small molecule drug discovery and methods of screening compositions to determine their effectiveness for treatment of ribosomal disorders and ribosomopathies.

21 Claims, 24 Drawing Sheets
Specification includes a Sequence Listing.

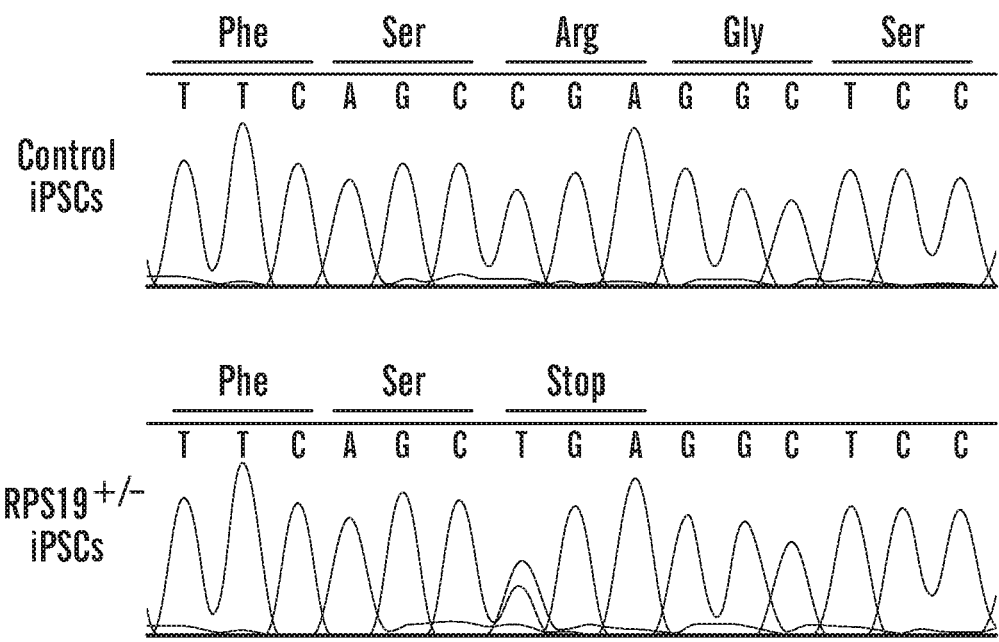
FIG. 1A
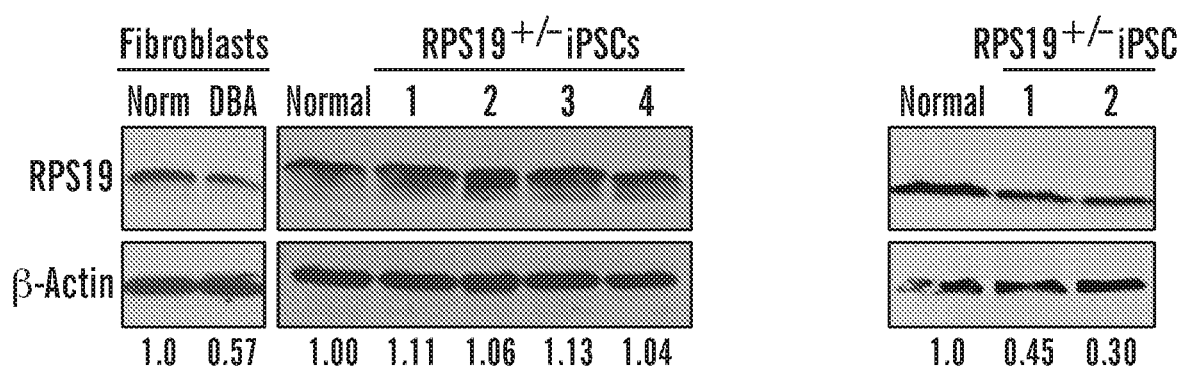
FIG. 1B
FIG. 1C

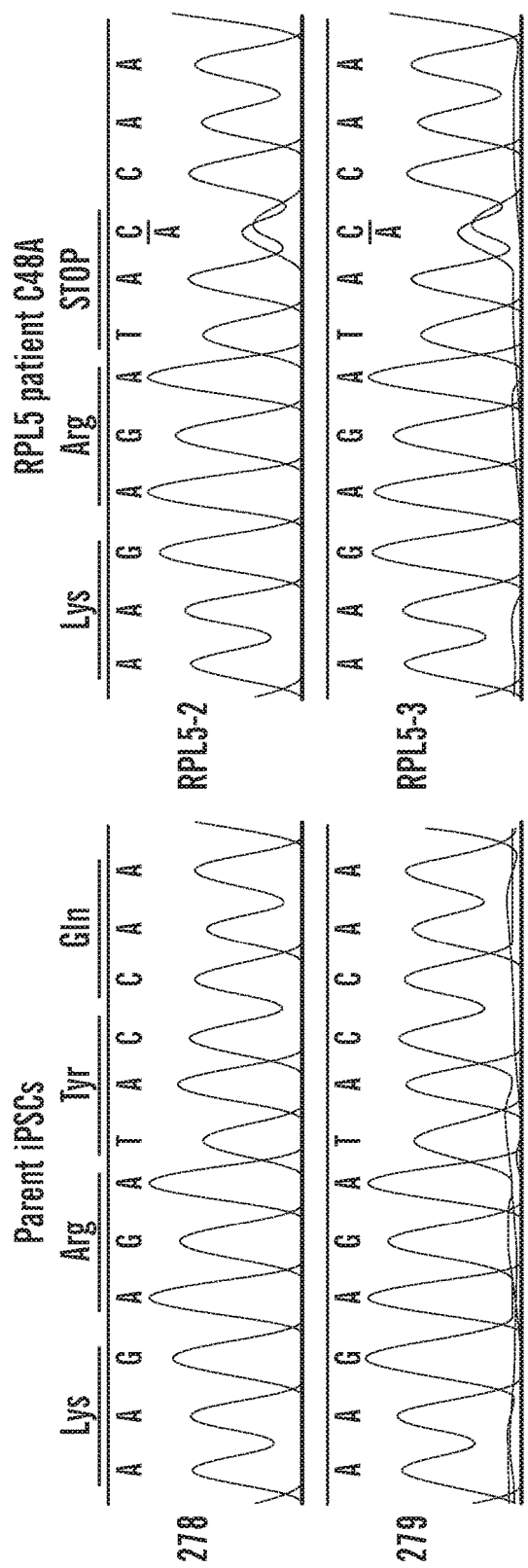
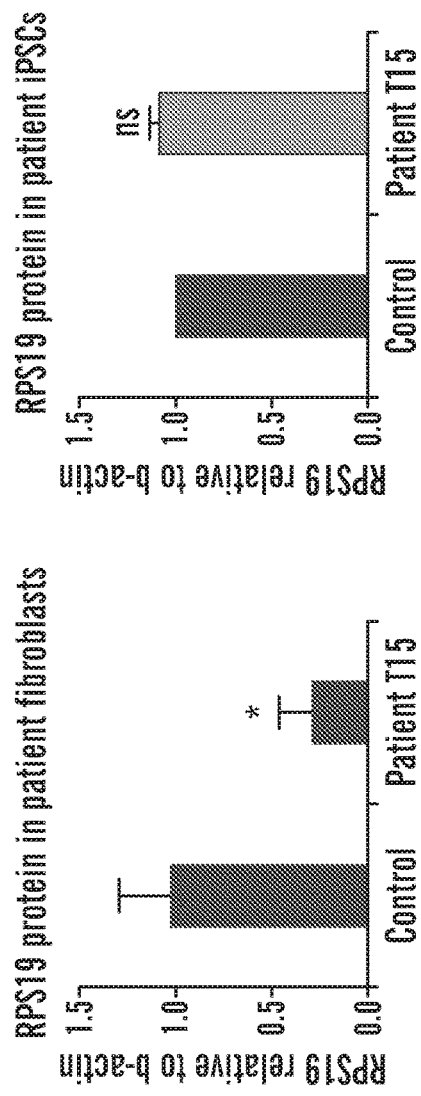
FIG. 2A
FIG. 2B

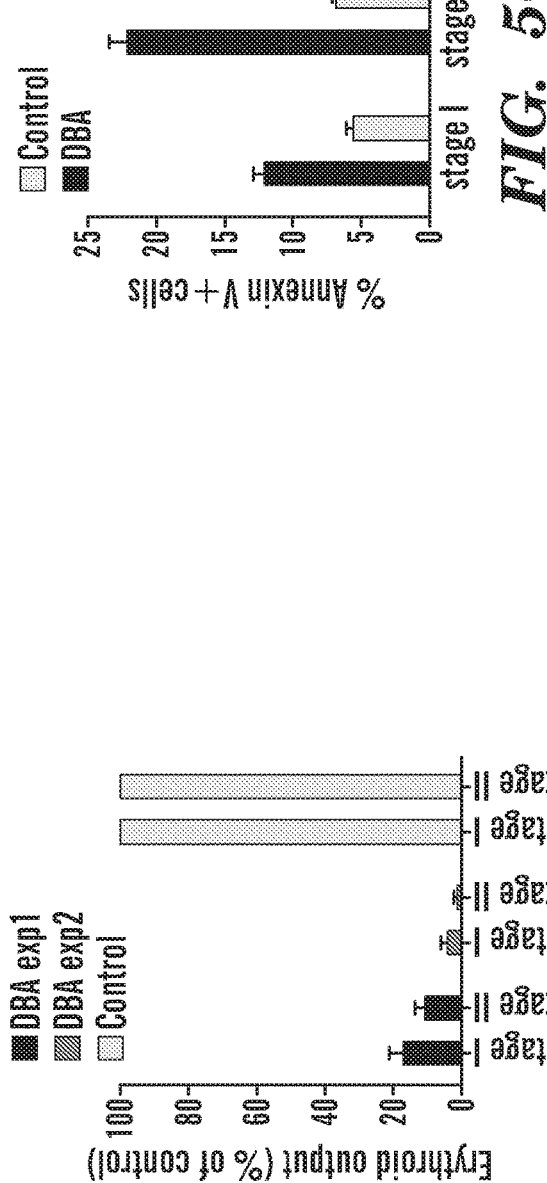
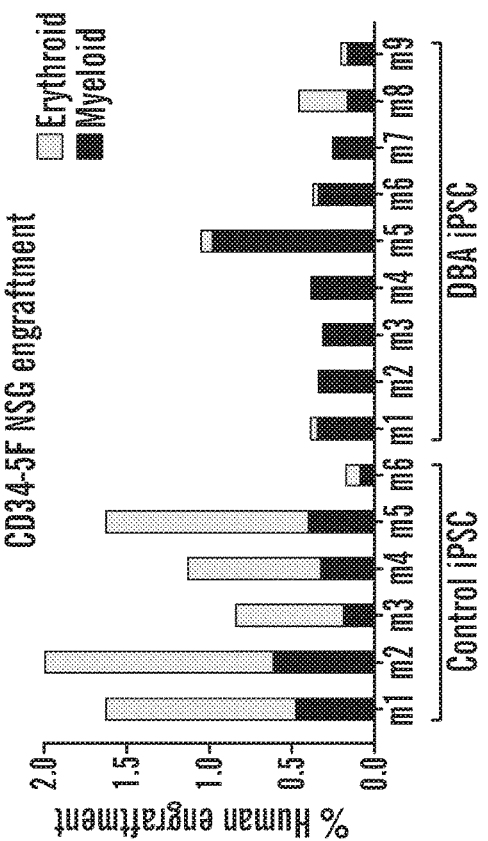
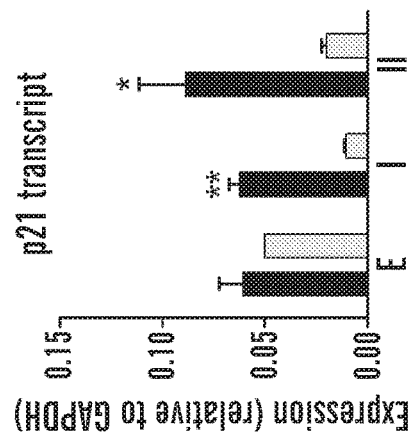
FIG. 5B
FIG. 5C
FIG. 5D
FIG. 5E

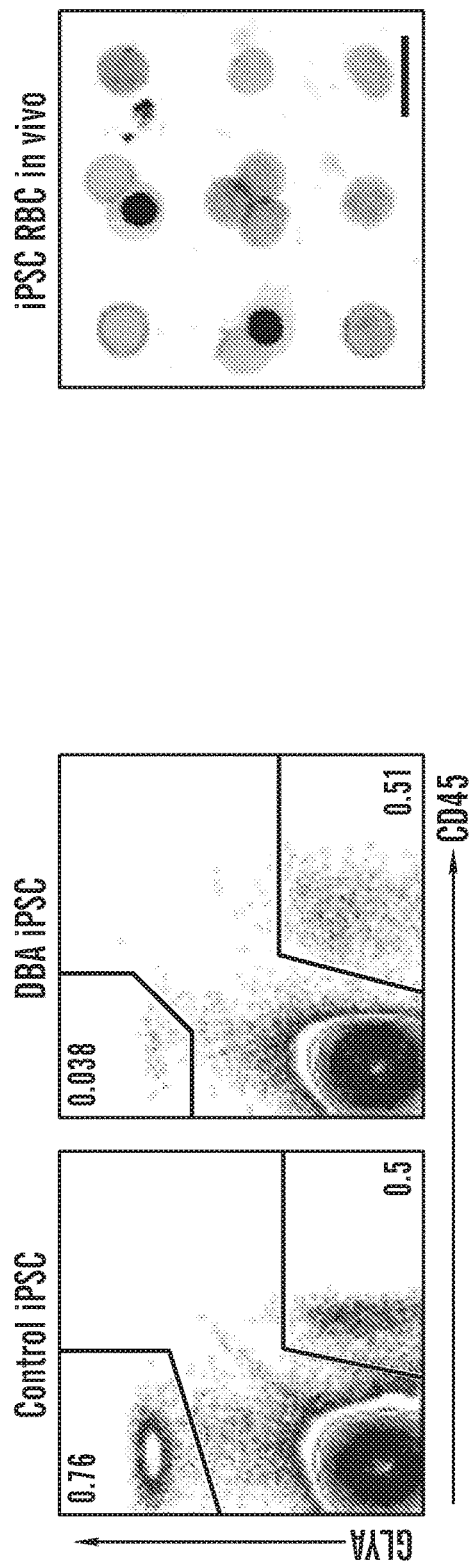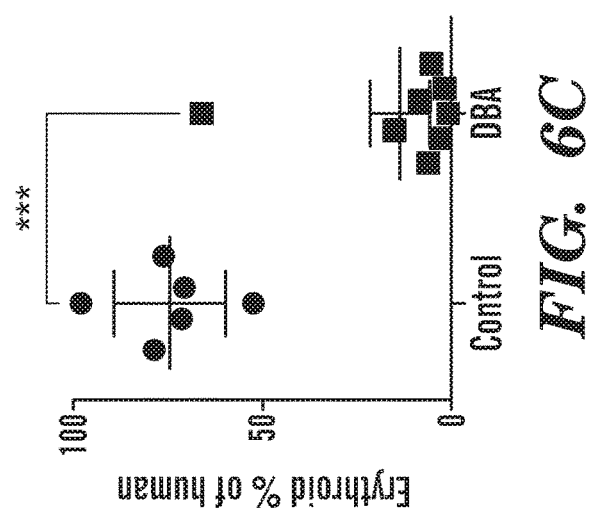
FIG. 6A
FIG. 6B
FIG. 6C

| | |
|---|---|
| 1. 8-MIMX | Calmodulin-PDE1 inhibitor |
| 2. Cilnidipine | Calcium channel inhibitor |
| 3. Carbamazepine | Inducer of autophagy |
| 4. Sodium Taurocholate | Taurine biosynthesis |
| 5. Pyrilamine maleate | H1 histamine reverse agonist |
| 6. 1-Aminobenzotriazole | Cytochrome P450 inhibitor |
| 7. Aminoreservatrol sulfate | Inducer of autophagy |
| 8. SMER28 | Inducer of autophagy |
| 9. A3 hydrochloride | Casein Kinase inhibitor |
| 10. Bicalutamide (CDX) | Androgen receptor inhibitor |
| 11. EHNA | Adenosine deaminase inhibitor |

*FIG. 9B*

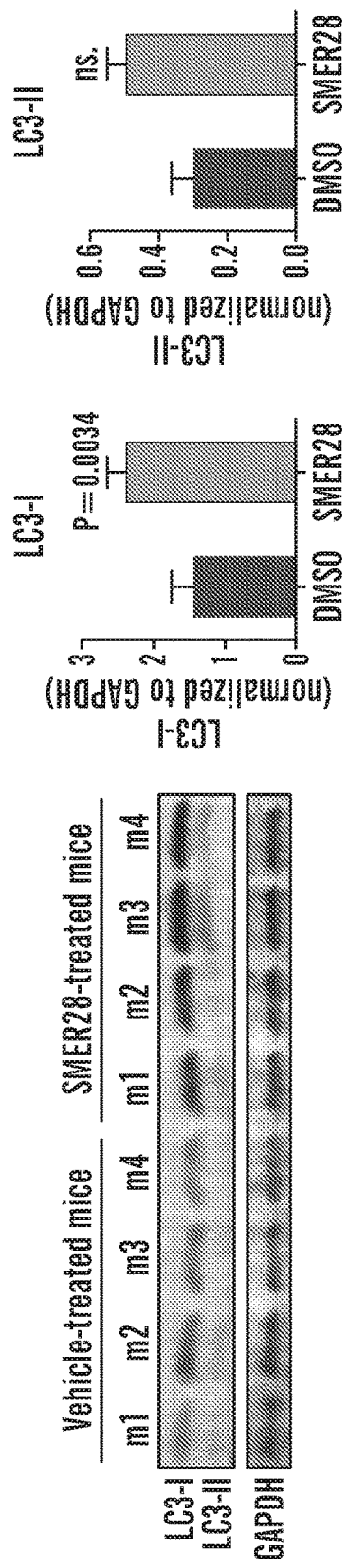
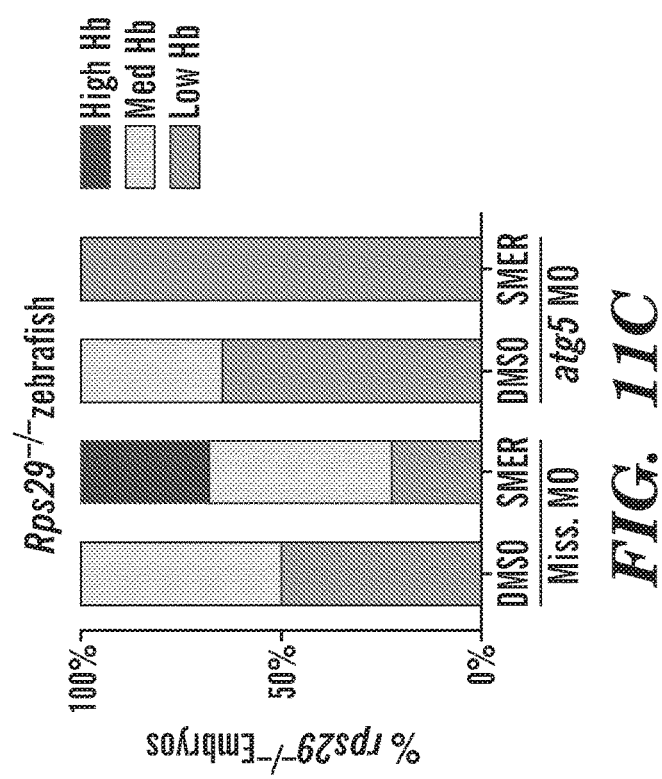
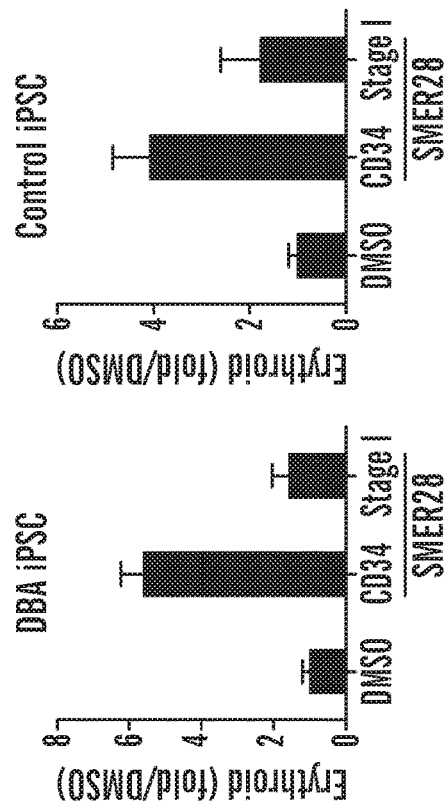
FIG. 11A
FIG. 11B
FIG. 11C

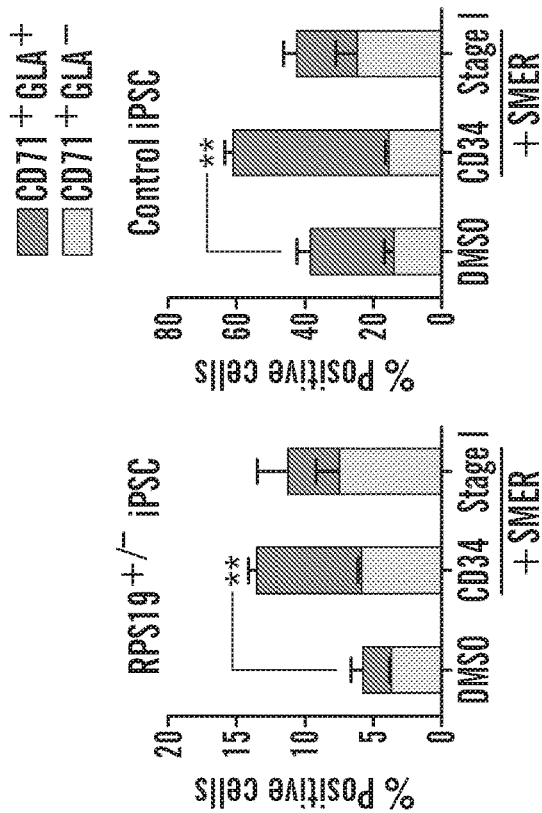
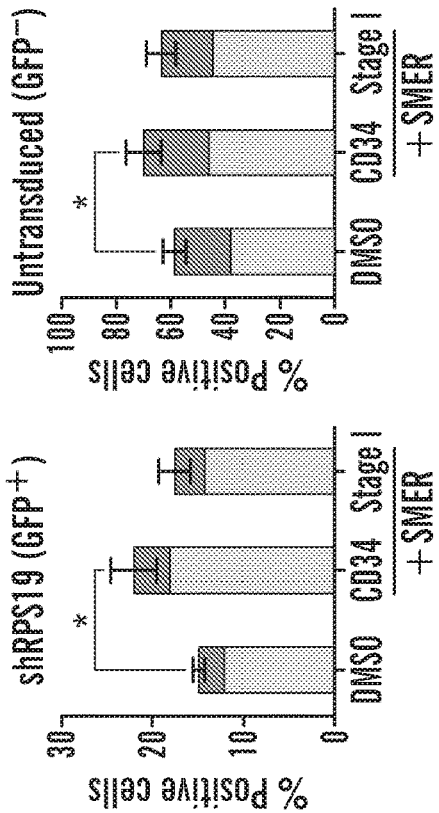
FIG. 12B
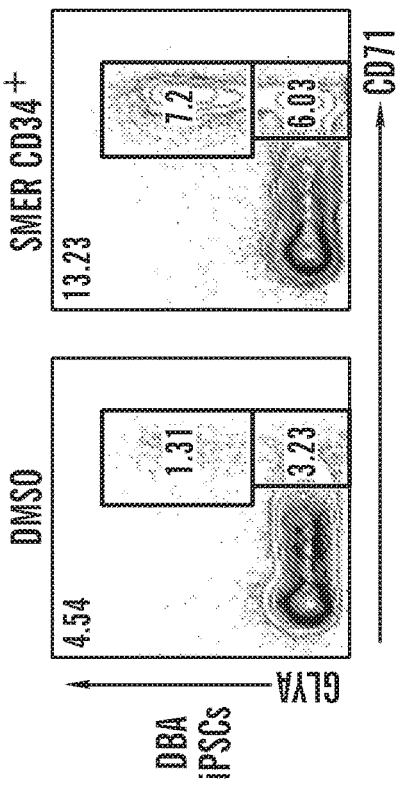
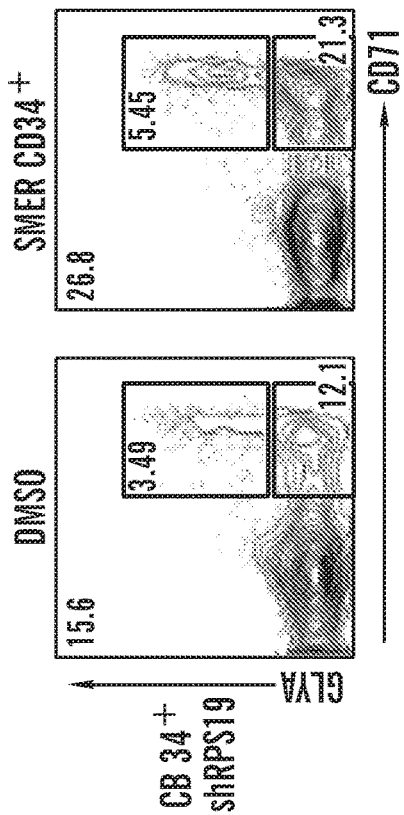
FIG. 12A
FIG. 12C

COMPOUNDS AND METHODS FOR TREATMENT OF DIAMOND BLACKFAN ANEMIA

GOVERNMENT SUPPORT

This invention was made with government support under Grant Numbers HL100001 AND DK092760, awarded by the National Institutes of Health. The Government has certain rights in the invention.

CROSS-REFERENCE TO RELATED APPLICATIONS

This Application is a 35 U.S.C. § 371 National Phase Entry Application of International Application No. PCT/US2017/036520 filed Jun. 8, 2017, which designates the U.S.

SEQUENCE LISTING

The instant application contains a Sequence Listing which has been submitted electronically in ASCII format and is hereby incorporated by reference in its entirety. Said ASCII copy, created on Jul. 5, 2017, is named 701039-089700-PCT_SL.txt and is 2,015 bytes in size.

FIELD OF THE INVENTION

The present invention relates generally to methods, compositions and kits for treatment of ribosomal disorders and ribosomopathies, e.g. Diamond Blackfan Anemia (DBA) and screening methods for finding treatments to these conditions. In some embodiments, the invention relates to the use of autophagy modulators for treatment of ribosomal disorders and ribosomopathies.

BACKGROUND OF THE INVENTION

Diamond Blackfan anemia (DBA) is a congenital anemia that presents in children, often before one year of age (Vlachos et al., 2008). The primary symptom for these patients is a block in erythroid differentiation and possible defect in hematopoietic stem cells (HSCs), and some patients also have 4818-2650-1449.3 craniofacial anomalies. Ribosomal protein S19 (RPS19) was the first gene found mutated in DBA patients (Draptchinskaia et al., 1999). Sequencing of patient samples has identified mutations of either large (60s) or small (40s) subunit ribosomal proteins in over 50% of patients (Vlachos et al., 2010), most recently rps29. Patients are heterozygous for these mutations, always maintaining a wildtype copy of the affected ribosomal protein gene.

Ribosomal protein knockdown leads to an increase of free ribosomal proteins. Some ribosomal proteins, including RPL11 and RPL5, can prevent p53 degradation, as they are able to bind MDM2 and sequester it from p53 (Fumagalli et al, 2009). RPL26 has been shown to increase p53 protein by an alternative mechanism, as it can bind p53 mRNA, increasing its translation (Tagaki et al., 2005). p53 activation plays an important role in DBA pathogenesis, as well as in other diseases where ribosomal and related genes are mutated, now termed ribosomopathies. These include 5q-myelodysplastic syndrome, where one copy of RPS14 is lost. p53 activation is also a common feature in bone marrow failure disorders, such as Fanconi Anemia (Ceccaldi et al., 2012). In human CD34+ cells, RPS19 knockdown leads to p53 activation (Ebert et al., 2005; Flygare et al., 2005), with increased accumulation in erythroid cells. Differentiation defects can be rescued by p53 inhibition (Dutt et al., 2011). Mouse models of RPS19 mutation or knockdown have hematopoietic defects that can be rescued by p53 mutation (McGowan et al., 2008; Jaako et al., 2011). Rps19 has been targeted by morpholino in zebrafish embryos, and the hematopoietic defects in rpl11 mutant zebrafish are rescued by p53 knockdown (Danilova et al., 2008; Torihara et al., 2011; Danilova et al., 2011).

Ribosomal protein mutations are common in patients with Diamond Blackfan anemia (DBA), who have red cell aplasia and craniofacial abnormalities. The inventors have previously characterized zebrafish mutant rps29, a ribosomal protein in the small subunit, that have hematopoietic and endothelial defects (Taylor et al., 2012). Rps29−/− embryos have morphological defects in the head, as well as decreased hematopoietic stem cells, hemoglobin, and staining of endothelial markers. Consistent with other models of DBA, knockdown of p53 near completely rescues the rps29 mutant phenotype.

The inventors demonstrated that Rps29−/− embryos have a defect in arterial specification, leading to decreased HSCs and decreased flk1 expression in the intersegmental vessels at 24 hours post fertilization (hpf). Primitive erythropoiesis is also affected, as rps29−/− embryos have less hemoglobin. These embryos also have increased apoptosis, particularly in the head, and die by five days post fertilization (dpf). p53 pathways are activated in the embryo, and p53 mutation rescues all hematopoietic and apoptotic phenotypes.

The current treatment options for diseases associated with a ribosomal disorder or ribosomopathy, e.g., a mutation in a ribosomal protein are far from optimal, especially for Diamond Blackfan anemia (DBA). There is therefore an urgent need for effect screening methods to discover treatments for theses diseases and to apply these screening methods for the discovery of novel, effective, and targeted therapies for diseases associated with a ribosomal disorder or ribosomopathy, e.g., a mutation in a ribosomal protein. In particular, there is a strong need in the art for improved methods for treatment of DBA with small-molecule drugs.

SUMMARY OF THE INVENTION

The present invention is generally directed to methods, compositions and kits for treatment of ribosomal disorders and ribosomopathies, e.g. Diamond Blackfan Anemia (DBA). The invention also relates to methods of screening compositions to determine their effectiveness for treatment of ribosomal disorders and ribosomopathies.

In one aspect the invention relates to a method of treating a subject with ribosomal disorder or ribosomopathy, comprising administering an effective amount of a compound having Structure I or a derivative, analogue or pharmaceutically acceptable form thereof.

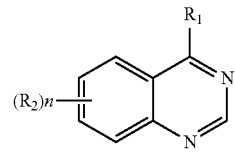

Structure I $R_1$ can be hydrogen; halogen; cyclic or acyclic, substituted or unsubstituted, branched or unbranched aliphatic;

cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; —C(═O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; —C(R$_A$)$_3$;

—CH$_2$CH$_2$R$_D$; wherein each occurrence of R$_A$, R$_C$, or R$_D$ is independently a hydrogen, a protecting group, an aliphatic moiety (e.g., ethyl, methyl or propyl), a heteroaliphatic moiety, an unsaturated group (e.g., Allyl), an acyl moiety, 4-(1,3-Benzodioxol-5-ylmethyl), Phenol, 4-Chlorophenyl, 4-Phenoxypheny, 4-(Cyclopentyloxy)phenyl, 4-(Benzyloxy)phenyl or Ethyl (4-phenoxy)acetate; an aryl moiety (e.g., benzyl); a heteroaryl moiety; alkoxy; aryloxy; alkylthio; arylthio; amino, alkylamino, dialkylamino, heteroaryloxy; or heteroarylthio moiety.

R$_2$ can be hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_B$; —C(═O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

n is an integer between 0 and 4, inclusive. In certain embodiments, n is 1. In certain embodiments, n is 2. In certain embodiments, n is 3.

In certain embodiments, R$_1$ is —OR$_A$. In certain embodiments, R$_1$ is —SR$_A$. In certain embodiments, R$_1$ is —NHR$_A$. In certain embodiments R$_1$ is

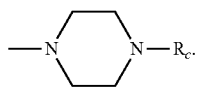

In certain embodiments R$_1$ is —CH$_2$CH$_2$R$_D$. In certain embodiments, R$_A$ is C$_1$-C6 aliphatic. In certain embodiments, R$_A$ is C$_2$-C$_6$ alkenyl.

In certain embodiments, R$_A$ is vinyl. In certain embodiments, R$_A$ is allyl. In certain embodiments, R$_1$ is —OR$_A$, wherein R$_A$ is allyl. In certain embodiments, R$_1$ is —NHR$_A$, wherein R$_A$ is allyl. In certain embodiments, R$_A$ is benzyl.

In certain embodiments, R$_2$ is halogen. In certain embodiments, R$_2$ is fluoro. In certain embodiments, R$_2$ is chloro. In certain embodiments, R$_2$ is bromo. In certain embodiments, R$_2$ is —OR$_B$. In certain embodiments, R$_2$ is —OH.

Optionally, the compound has Structure II, or is a derivative or analogue of the compound with Structure II, or is a pharmaceutically acceptable form thereof.

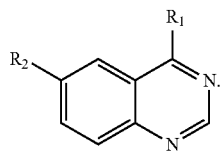

Structure II

Optionally, the compound is 6-Bromo-N-2-propenyl-4-quinazolinam (SMER28) or a derivative or analogue of the compound with Structure III, or is a pharmaceutically acceptable form thereof.

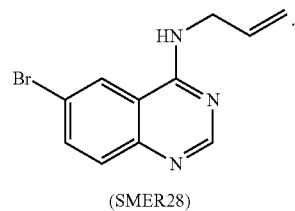

Structure III (SMER28)

Optionally, the ribosomal disorder or ribosomopathy is selected from a group consisting of: Diamond Blackfan Anemia (DBA), inherited erythroblastopenia, 5q-syndrome, Schwachman-Diamond syndrome, Dyskeratosis congenita, Cartilage hair hypoplasia, and Treacher Collins syndrome, Hoyeraal-Hreidarsson syndrome, and Prader-Willi syndrome. Optionally, the ribosomal disorder or ribosomopathy is Diamond Blackfan Anemia (DBA). Optionally, the ribosomal disorder or ribosomopathy or inherited erythroblastopenia. Optionally, the subject has DBA1, DBA2, DBA3, DBA4, DBA5, DBA6, DBA7, or DBA8. Optionally, the subject has at least one mutation in ribosomal protein selected from the group consisting of: RPS7, RPS10, RPS19, RPS24, PRS26, RPS17, PRS27L RPS29. RPL35A, RPL5 and RPL11. Optionally, the subject has a mutation in ribosomal protein 19 (RPS19). Optionally, the subject is administered another therapeutic agent to treat the ribosomal protein defect. For example, the subject is administered another therapeutic agent to treat the ribosomal protein defect, selected from the group consisting of: corticosteroids and blood transfusions.

Optionally, the compound increases erythroid differentiation of a hematopoietic progenitor cell in the subject. Optionally, the compound increases differentiation of a CD71$^+$GlyA$^+$erythroid cell or population thereof in the subject. Optionally, the compound increases the levels of hemoglobin in the subject. Optionally, the compound increases the levels of Red blood cells in the subject. Optionally, the compound induces autophagic flux in a erythroid cell or population thereof in the subject. Optionally, the compound increases erythropoiesis in vivo or in vitro. Optionally, the compound decreases p62 levels and increases the levels of lipidated LC3-II.

Accordingly, one aspect of the present invention relates to a method for treating DBA, the method comprising; administering to a subject in need thereof a therapeutically effective amount of 6-Bromo-N-2-propenyl-4-quinazolinam (SMER28). Optionally, the patient has a mutation in the ribosomal protein RPS19.

Another aspect of the invention relates to a method for increasing the rate of red blood cell (RBC) differentiation, the method comprising: contacting a erythroblast or a population thereof at stage I-III of differentiation with SMER28. Optionally, the erythroblast is derived from an embryonic stem cell or induced pluripotent stem cell in vitro. Optionally, the erythroblast is isolated from a patient.

In another aspect, the invention relates to a method for inducing Red Blood Cells (RBC) differentiation. The method includes contacting a hemtopoietic progenitor cell (HPC) or population thereof with nucleic acid encoding the reprogramming factors HOXA9, ERG, RORA, SOX4, and MYB for a sufficient time to induce a differentiated RBC. In certain embodiments, the sufficient time is at least 2 weeks. Optionally, the nucleic acid is expressed by a lentivirus. Optionally, the lentivirus is inducible. Optionally, the method further comprises erythroid maturation. Optionally, the HPC or population thereof is/are $CD34^+$ $CD45^+$. Optionally, the HPC or population thereof is derived from a inducible pluripotent stem cell (iPS) or a pluripotent stem cell. Optionally, the HPC or population thereof is isolated from a patient. Optionally, the (iPS) is derived from a somatic fibroblast. Optionally, the somatic fibroblast cell is a mammalian cell. Optionally, the somatic fibroblast cell is a human cell. Optionally, the somatic fibroblast cell is a human cell and isolated from a subject with a ribosomal disorder. Optionally, the somatic fibroblast cell is a human cell and isolated from a subject with DBA. Optionally, the somatic fibroblast cell is a human cell and isolated from a subject with a mutation in the ribosomal protein RSP19. Optionally, the somatic fibroblast cell differentiated to a iPS in vitro, ex vivo, or in vivo. Optionally, the iPS or pluripotent stem cell is differentiated to a HPS in vitro, ex vivo, or in vivo. Optionally, the method further comprises engraftment of the differentiated RBC ex vivo or in vivo. Optionally the somatic fibroblast cell is a mammalian cell. Optionally, the somatic fibroblast cell is a human cell. Optionally, the somatic fibroblast cell is a human cell and isolated from a subject with a ribosomal disorder. Optionally, the somatic fibroblast cell is a human cell and isolated from a subject with DBA. Optionally, the somatic fibroblast cell is a human cell and isolated from a subject with a mutation in the ribosomal protein RSP19. Optionally, the differentiated RBC is $CD71^+GlyA^+$. Optionally, the differentiated RBC is enucleated.

In another aspect the invention relates to an ex vivo method for screening agents to promote hematopoietic cell differentiation comprising the steps of: exposing a population of cells (e.g., RBC that have been induced to differentiation as described herein) to a candidate agent ex vivo; and comparing hematopoietic cell differentiation rate of the population of cells exposed to the candidate agent to a population of cells that has not been exposed to the candidate agent, wherein if the hematopoietic cell differentiation rate is increased in the population of cells exposed to the candidate agent compared to the population of cells that has not been exposed to the candidate agent, the agent is indicated as an agent that expands hematopoietic stem cells. Optionally, the hematopoietic cell is an erythroid. Optionally, the hematopoietic cell is an erythroblast. Optionally, the hematopoietic cell is a non-enucleated red blood cell. Optionally, the hematopoietic cell is a enucleated red blood cell. Optionally, the hematopoietic stem activity is self-renewal.

In another aspect, the methods relate to a method of treating a subject anemia, comprising administering an effective amount of methoctramine to the subject. Optionally, the subject has treatment-related anemia due to treatment for another disorder such as cancer or dysplasia which include myelosuppression, chemotherapy, immunosuppression, or radiation therapy.

In another aspect, the method relates to a method of treating a subject with a ribosomal disorder or ribosomopathy, comprising administering an effective amount of a autophagy modulator to the subject to decrease p21 and apoptosis in at least one of CD34+ cells, erythroid cells or erythroid differentiated cells in the subject. Optionally, the autophagy is activated. Optionally, the autophagy activator is a compound having Structure I, or a derivative, analogue or pharmaceutically acceptable form thereof. For example, the autophage activator is SMER28.

The methods, compositions, such as compounds with Structure I are useful in treatments of ribosomal disorders and ribosomopathies. In addition, the methods described herein useful for discovering new therapies, treatments and compositions for ribosomal disorders and ribosomopathies.

BRIEF DESCRIPTION OF THE DRAWINGS

FIGS. 1A-1G show DBA iPSCs phenocopy erythroid defects in vitro. (FIG. 1A) Genomic RPS19 DNA sequence from control and DBA T15 iPSC lines. The sequence confirms the presence of a heterozygous C280T nonsense mutation in patient-derived iPSCs. One representative iPSC line is shown. (FIG. 1B) RPS19 expression in T15 patient fibroblasts (left) and multiple iPSC lines derived from them (right). RPS19 protein levels were quantified, normalized to control fibroblasts or iPSC lines, and indicated below lanes. (FIG. 1C) RPS19 expression in erythroid cells differentiated from T15 DBA iPSCs. RPS19 protein levels were quantified, normalized to erythroid cells from control iPSCs, and indicated below lanes. (FIG. 1D) Experimental outline. From left to right: DBA iPSCs are differentiated into $CD34^+$ $CD45^+$d14 EB-HPCs, transduced with 5F, and respecified on Dox for 14 days (CD34-5F cells). During this stage progenitors are maintained in an undifferentiated $CD34^+$ $CD38^-$ state. Next, Dox is removed, initiating differentiation into erythroid ($CD34^+$ $CD71^+$) and myeloid progenitors (day 0-4 of differentiation). Erythroid maturation occurs over the next 17 days in the presence of Epo (stages I-III; days 5-21 of differentiation). Approximate cell counts for each stage are listed (see FIG. S3C). (FIG. 1E) May-Grunwald-Giemsa staining of normal CD34-5F cells from different stages of erythroid culture. The day of differentiation corresponding to each stage is in top left corner (Dox withdrawal=day 0). Day 18 includes benzidine staining for hemoglobin. E: erythroblast; M: myeloid. (FIG. 1F) Erythroid differentiation of CD34-5F cells derived from control, $RPS19^{+/-}$, and $RPL5^{+/-}$ DBA iPSCs. Top: May-Grunwald-Giemsa and benzidine stain for hemoglobin of cells after stage I (day 9 of differentiation). Bottom: Erythroid markers, CD71 and GlyA. Data are representative of 4 experiments with 3 control iPSC lines, 4 $RPS19^{+/-}$ DBA iPSC lines, and 2 $RPL5^{+/-}$ iPSCs. (FIG. 1G) Colony-forming capacity of control (n=4) and DBA (n=5) CD34-5F cells showing myeloid (left) and erythroid (right) colonies. ***p<0.001 by unpaired t-test.

FIGS. 2A and 2B show sequence analysis for parent and patient iPSCs. (FIG. 2A) Sequence analysis confirms heterozygous nonsense mutation in iPSCs by Sanger sequencing. (FIG. 2B) RPS19 protein levels in parent and patient iPSCs.

(FIG. 3A) FACS plots showing CD34 and CD45 expression levels. (FIG. 3B) Bar graph showing the percentage of CD34$^+$ CD45$^+$ cells in the indicated genotypes.

(FIG. 4A) Bar graph showing the percent of erythroid in the indicated population. (FIG. 4B) Bar graphs shows the level of p21 relative to GAPDH in iPSC and RBC in the indicated genotype. (FIG. 4C) Plot showing that the expansion of erythroids is unchanged in two different iPSC populations.

FIGS. 5A-5E show differentiation defects in patient-derived cells. (FIG. 5A) Micrographs highlighting a reduction in CD71$^+$GlyA$^+$ cells frequency and number in patient-derived cells compared to control. (FIG. 5B) Bar graph showing the erythroid output as a percentage of the control for the indicated genotypes. (FIG. 5C) Bar graph showing the percentage of Annexin positive cells for the indicated genotype.

FIGS. 6A-6C show DBA iPSCs show defective erythropoiesis in vivo. (FIG. 6A) Representative flow plots of human erythroid (GLYA$^+$) and myeloid (CD45) engraftment in the bone marrow of NSG mice transplanted with control (n=6 mice) or DBA (n=9 mice) CD34-5F cells. Engraftment was analyzed 4 weeks after transplantation using human-specific lineage antibodies as detailed in Experimental Procedures. Each plot is a single mouse, and two mice engrafted with different control and DBA lines are shown. (FIG. 6B) Morphology of sorted GLYA$^+$ red blood cells from the bone marrow of mice engrafted with control iPSC progenitors. (FIG. 6C) Erythroid cells as proportion of total human engraftment for control and DBA iPSCs, plotted as a percentage. Data are shown as mean±s.e.m of two independent experiments, using 2 control lines and 2 RPS19$^{+/-}$ DBA lines.

(FIG. 7A) Erythroid differentiation of RFP- and RPS19-complemented RPS19 DBA iPSCs in vitro. Erythroid cells were analyzed on day 9 using markers CD71 and GlyA. Quantitation on the right is shown as mean±s.e.m. for 3 DBA iPSC, 3 RFP-corrected (RFP), and 4 RPS19-corrected (RPS19) iPSC lines independently derived during gene correction. (FIG. 7B) Erythroid engraftment of RFP- and RPS19-complemented RPS19$^{+/-}$ DBA iPSCs 4 weeks after transplantation in NSG mice (n=3 each). Quantitation on the right shows human GlyA$^+$ erythroid cells as percent of total human engraftment. (FIG. 7C) Erythroid differentiation of CD34-5F cells derived from the RPL5$^{+/-}$ patient and unaffected parent iPSCs. Erythroid cells were analyzed on day 9 using markers CD71 and GlyA. *p<0.001, p<0.01, by unpaired t-test.

(FIG. 8A) The distribution of 1440 compounds by Z-score in a proliferation-based screen of the Sigma LOPAC chemical library. DBA CD34-5F cells were plated in erythroid-promoting conditions in 384-well format. Erythroid proliferation was measured in the presence of 5 µM of each compound, and converted into Z-scores. The cut-off for significance was set at Z=3 (22 compounds, shown in red; listed in FIG. S5B). The screen was carried out with 3 RPS19 DBA and 2 normal iPSC lines. (FIG. 8B) Dose-dependent effect of SMER28 (in µM) on erythroid differentiation, shown as the absolute number of erythroid cells in each drug-treated condition normalized to vehicle (DMSO) control. Erythroid cells were analyzed on day 9 of differentiation using markers CD71 and GlyA. Dose curve was performed with DBA (n=5) and control (n=3) iPSCs. Non-linear regression curve was plotted to calculate EC$_{50}$ values. Data for RPL5$^{+/-}$ iPSCs are shown in FIG. S5C. (FIGS. 8C and 8D) Dose-dependent effect of SMER28 (in µM) on erythroid differentiation of CB CD34$^+$ RPS19$^+$ cells. (FIG. 8C) Absolute number of erythroid cells (analyzed on day 9) in each drug-treated condition normalized to vehicle (DMSO) control (4 independent experiments). Non-linear regression curve was plotted to calculate EC$_{50}$ values. (FIG. 8D) Representative flow plots of control (shLUC) and RPS19$^{sh}$ cells treated with DMSO or increasing doses of SMER28.

FIGS. 9A-9D show compounds screened for rescue of erythroid differentiation defects. (FIG. 9A) Shows Z-scores for compounds tested on control or DBA iPSC. (FIG. 9B) List of compounds screened that provided promising results. (FIG. 9C) FACS plots showing GlyA and CD71 expression levels for indicated genotype (top panels). Micrographs showing GlyA$^+$ CD71$^+$ cells in indicated genotype (bottom panels). (FIG. 9D) Plot showing the percentage of Annexin and DAPI positive cells following varying doses of SMER28.

(FIG. 10A) SMER28 rescues RBC output in rps29$^{+/-}$ zebrafish embryos. The level of hemoglobin in the yolk sac was visualized 40hpf with benzidine staining. Images are representative of the proportion of embryos indicated (of total counted). (FIG. 10B) Quantitation of SMER28 rescue for a range of 0.1-1 µM, with embryos grouped by high, medium, and low levels of hemoglobin staining. (FIG. 10C) Peripheral blood (PB) RBC counts and hematocrit in mice with irradiation-induced anemia. Mice were treated with the PEG400-based vehicle containing DMSO (VEH) (n=11), 1 mg/kg Dex (sodium-phosphate) (n=13), or 10 mg/kg SMER28 (n=9) for 3 weeks, bled, and assessed. Data are combined from 3 independent experiments. (FIG. 10D) Erythroid cells as proportion of the human graft in mice transplanted with DBA CD34-5F progenitors, and treated as in (FIG. 1c). (FIG. 10E) Levels of human engraftment in NSG mouse bone marrow (BM) transplanted with CB CD34$^+$ cells. Mice were treated with DMSO plus vehicle (VEH) (n=10), 1 mg/kg Dex (sodium-phosphate) (n=6), or 2 mg/kg SMER28 (n=11) for 4 weeks. (FIG. 10F) The proportion of erythroid, myeloid, and lymphoid (B cells) lineages within the human graft in vehicle- and SMER28-treated mice transplanted with CB CD34$^+$ cells. Only the effect on the erythroid lineage was significant. Data in FIGS. 10E-10G are pooled from 2 independent experiments. For all panels, *p<0.05, **p<0.01.

FIGS. 11A-11C show effect of SMER28 on CD34+ progenitors. (FIG. 11A) Protein levels of LC3-I and LC3-II in control and SMER28 treated mice. GADPH is used as a loading control. (FIG. JIB) Absolute numbers; CD34$^+$ progenitors treated only during the initial expansion phase displayed increased output of GlyA$^+$ cells. (FIG. 11C) Atg5 morpholino treatment of rps29$^{+/-}$ zebrafish.

FIGS. 12A-12F shows SMER28 promotes erythroid differentiation of CD34 progenitors. (FIG. 12A) Erythroid differentiation of control and DBA CD34-5F cells treated with DMSO vehicle or SMER28 (10 µM) during the initial CD34$^+$ progenitor phase (day 0-4 of differentiation), or stage I of erythroid culture (day 4-9 of differentiation). Percent of erythroid cells after stage I of differentiation is indicated in top left for each condition, and quantitated in (FIG. 12B). Absolute numbers of erythroid cells are shown in FIG. S6B. Data are shown as mean f s.e.m. of 4 independent experiments, with 2 control and 4 DBA iPSCs. (FIG. 12C) Same as (FIG. 12A) for CB CD34+ cells transduced with shRPS19 hairpins. GFP$^+$ RPS19$^{sh}$ and GFP$^-$ control cells were quantitated separately. Quantitation on the right shows mean±s.e.m. of 3 experiments. (FIG. 12D) RBC pellets at the end of stage III initiated with equal numbers of CD34-5F or CB progenitors. SMER28 was added at 10 M. (FIG. 12E) May-Grunwald-Giemsa stain of erythroid cells from CB CD34$^+$ at end of stage III. Arrows indicate enucleated RBCs, which are quantitated by flow cytometry. (FIG. 12F) Quantitation of the enucleation efficiency (left) of GLYA$^+$ cells. Data in FIGS. 12E-12F represents 3 independent experiments. For all panels, *p<0.05, **p<0.01.

(FIG. 13A) Induction of autophagy by SMER28 (40 μM) monitored by protein levels of p62, LC3-I, and LC3-II after 24 hours. Cells were also treated with 5-FU (100 nM) to induce autophagy, or inhibitor of transcription actinomycin D (ActD; 100 nM). (FIG. 13B) Induction of autophagy by SMER28 (40 μM) monitored by protein levels of p62, LC3-I, and LC3-II after 24 hours treatment with or without lysosomal blockade with bafilomycin A (200 nM for 4 hours). Untreated samples are shown at higher exposure, to capture dynamic changes in the LC3-II levels. Rapamycin (200 nM) is a positive control. LC3-II levels relative to GAPDH are quantitated on the right. (FIG. 13C) Erythroid differentiation of CD34-5F cells transduced with shRNAs for luciferase (LUC) or ATG5±SMER28. Representative flow plots and quantitation showing the number of erythroid cells induced by SMER28 (10 μM) normalized to DMSO. 2 control luciferase shRNAs and 2 ATG5 shRNAs are included (knockdown efficiency in hematopoietic cells of 58% and 50%, respectively), each with 2 independent lines; p=0.005, 3 independent experiments. (FIG. 13D) Atg5 deficiency causes anemia in zebrafish. Wild-type zebrafish embryos were treated with 1.6 ng atg5 or missense morpholino, and hemoglobin staining was visualized with benzidine staining at 40 hpf with SMER28 (1 μM). Representative images (left), and quantitation (right) with embryos grouped by high, medium, and low levels of benzidine staining. Atg5 morpholino treatment of rps29$^{+/-}$ zebrafish is shown in FIG. 11C.

DETAILED DESCRIPTION OF THE INVENTION

Figure 1D:
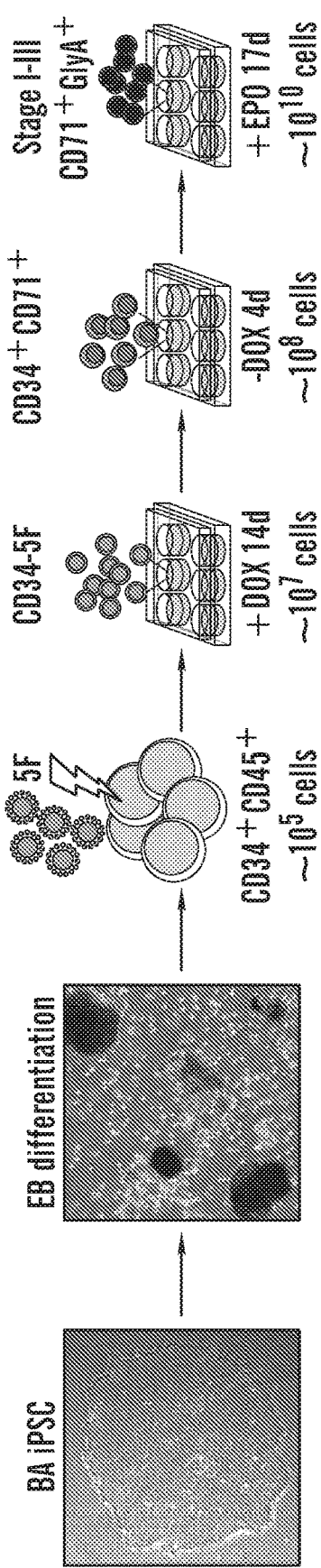

In some embodiments, the present invention is based upon the discovery that autophagy activators can be used to treat ribosomal disorders and ribosomopathies in subjects, for example, e.g. human subjects with Diamond Blackfan anemia (DBA). The inventors have discovered that autophagy activator rescued morphological defects and hematopoietic and endothelial defects in rps29−/− zebrafish embryos, an in vivo model of ribosomal protein defect, and also rescued rps19 knockdown in CD34+ differentiated cells, as well as decreased p21 levels back to normal. Therefore, the autophagy activator as disclosed herein can be used in a method for treatment of subjects with ribosomal protein disorders or ribosomopathies, e.g. Diamond Blackfan anemia (DBA) and other ribosomopathies, such as myelodysplasia, including 5q syndrome, Shwachman-Diamond syndrome and Treacher Collins Syndrome in human subjects.

In some embodiments the present invention is based on the discovery that small molecules such as those depicted by Structures I, II and III are effective for treatment of DBA. In addition to these structures, the compounds as set forth in International Patent Application Number PCT/US2008/059129 having international filing date Apr. 2, 2008, herein incorporated for reference, can be used for the treatments described herein. For example, molecules, analogues and derivatives of the structure in FIGS. 23, 24 and 31 of the PCT/US2008/059129 application that published as WO 2008/122038 on October 9, can be used.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Definitions

The term "regulate" used herein in reference to expression of a gene, refers to producing an effect on, for example, gene expression. In some embodiments, the effect can be stimulatory, such as increasing expression of a gene. In some embodiments, the effect can be inhibitory, such as decreasing expression of a gene. The terms "regulate" and "modulate" are interchangeably used herein.

The term "ribosomal protein", are also referred to herein as "r-proteins" refers to any of the intracellular ribonucleoprotein particles concerned with protein synthesis; they consist of reversibly dissociable units and are found either bound to cell membranes or free in the cytoplasm. They may occur singly or occur in clusters (polyribosomes). They may occur singly or in clusters, called polyribosomes or polysomes, which are ribosomes linked by mRNA and are actively engaged in protein synthesis. Ribonucleoproteins (often referred to as "RNPs") are important in protein synthesis; they consist of two, one large (L) and one small (S), reversibly dissociable units (called also 60S and 40S subunits in eukaryotes (50S and 30S in bacteria)). The term includes any of the proteins that, in conjunction with rRNA, make up the ribosomal subunits involved in the cellular process of translation. The term encompasses proteins of the small (S) subunit and the large (L) subunit of the ribosomes. Due to the high conservation of both the RNA and proteins moieties of ribosomes and of the ribosome biogenesis machinery from yeast and bacteria, a large part of the knowledge about these organic molecules has come from the study of E. coli ribosomes, and also applies to humans. In the small (30S) subunit of E. coli ribosomes, the proteins denoted S4, S7, S8, S15, S17, S20 bind independently to 16S rRNA. After assembly of these primary binding proteins, S5, S6, S9, S12, S13, S16, S18, and S19 bind to the growing ribosome. These proteins also potentiate the addition of S2, S3, S10, S11, S14, and S21. Protein binding to helical junctions is important for initiating the correct tertiary fold of RNA and to organize the overall structure. Nearly all the proteins contain one or more globular domains. Moreover, nearly all contain long extensions that can contact the RNA in far-reaching regions. Additional stabilization results from the proteins' basic residues, as these neutralize the charge repulsion of the RNA backbone. Protein-protein interactions also exist to hold structure together by electrostatic and hydrogen bonding interactions.

Theoretical investigations pointed to correlated effects of protein-binding onto binding affinities during the assembly process [2]

The term "ribosomal disorder" or "ribosomal protein disorder" refers to a disease or disorder linked to a mutated and/or abnormal function of a ribosome protein. It can include a disease due to mutation in a ribosomal protein, or a disease due to a decreased level, or partial loss of function, of a ribosomal protein, or alternatively, a disease due to an increased level of a ribosomal protein, as compared to a normal healthy control subject. The term ribosomal disorder includes genetic diseases of ribosomal proteins, including but not limited to, Diamond Blackfan Anemia (DBA), inherited erythroblastopenia, 5q-syndrome, Schwachman-Diamond syndrome, Dyskeratosis congenita, Cartilage hair hypoplasia, and Treacher Collins syndrome, Hoyeraal-Hreidarsson syndrome, and Prader-Willi syndrome.

The term "ribosomopathy" or "ribosomopathies" refers to any disease or malfunction of ribosomes. Ribosomes are small organelles found in all cells which are involved in the production of proteins by translating messenger RNA. A disease or malfunction of ribosomes include (i) disease of ribosomal biogenesis proteins, (ii) disease of small nucleolar ribonuceloproteins, and (iii) diseases of ribosomal proteins (as discussed above in the definition of "ribosomal protein disorder"), and are all reviewed in Freed et al., Mol. Biosyst. 2010; 6(3); 481-493 entitled "When ribosomes go bad: diseases of ribosome biogenesis", which is incorporated herein in its entirety by reference. Diseases of ribosomal biogenesis proteins include, but are not limited to Treachers Collins syndrome (TCS), male infertility due to a mutation in UTP14c, native American indian childhood cirrhosis (NAIC), Bowen-Conradi syndrome (BCS), alopecia neurological defect and endrocrinopathy syndrome (ANE syndrome), shwachman-diamond syndrome (SDS), candidate gene for primary open angle glaucoma (POAG), and modifier of neurofibromatosis type I (NF 1). Diseases of small nucleolar ribonucleoproteins include, but are not limited to, Anauxetic dysplasia (AD), cartilage-hair dysplasia (also called metaphyseal chondrodysplaia, McKusick type; CCH), metaphyseal dysplasia without hypotrichosis (MDWH), Dyskeratosis congenita (also called Zinzzer-Engman-Cole syndrome), Hoyeraal-Hreidarsson syndrome (where some cases are severe variants of Dyskeratosis congenita), and Prader-Willi syndrome (PWS)

The term "derivative" as used herein refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

The term "functional derivative" and "mimetic" are used interchangeably herein, and refers to compounds which possess a biological activity (in particular functional biological activity) that is substantially similar to the biological activity of the entity or molecule for which it's a functional derivative of. The term functional derivative is intended to include the fragments, variants, analogues or chemical derivatives of a molecule. In certain embodiments, functional derivatives and functional analogues of autophagy modulators (e.g., functional analogues of the compounds noted herein) can be assessed for their biological activity using the assay as disclosed herein, where derivatives and analogues which activate autophagy would be considered as functional derivatives or functional analogues of such autophagy modulators.

The term "analog" as used herein refers to an agent that retains the same, or a substantially similar biological function and/or structure as the molecule or chemical or polypeptide it is an analogue of. Examples of analogs include peptidomimetics (a peptide analog), peptide nucleic acids (a nucleic acid analog), small and large organic or inorganic compounds, as well as derivatives and variants of a polypeptide or nucleic acid herein.

The term "substantially similar", when used to define the biological activity of a derivative or analogue of a autophagy activator as compared to the biological activity of the autophagy activator to which it is a derivative or analogue of, means that a particular derivative or analogue differs from the initial autophagy activator in chemical structure, by one or more groups or elements, including substitutions, deletions, or additions of groups of elements, the net effect of which is to retain at least some of the biological activity found in the initial autophagy activator with respect to the activation of autophagy. Such biological activity of autophagy activation by a functional derivative or analogue of can be assessed by one of ordinary skill in the art using assays well known in the art, for example, autophagy activation may, inter alia, be determined in the following in vitro assay, which measured the autophagy-dependent reduction in p62 levels. If autophagy is activated the level of p62 is reduced in the cell. One skilled in the art will be able to assess p62 levels in cells contacted with an autophagy activator or derivative thereof.

The term "tissue" is intended to include intact cells, blood, blood preparations such as plasma and serum, bones, joints, muscles, smooth muscles, and organs.

The term "subject" includes human and other mammalian subjects that receive either prophylactic or therapeutic treatment. The term "subject" and "individual" are used interchangeably herein, and refer to an animal, for example a human, to whom treatment, including prophylactic treatment, with the cells according to the present invention, is provided. The "non-human animals" of the invention include mammals such as rats, mice, rabbits, sheep, cats, dogs, cows, pigs, and non-human primates.

The terms "a reference sample" or "a reference level" as used interchangeably herein refer to a negative control of the condition. For example, in the context of treatment, a reference level is the level if a subject is not treated. In some embodiments, a reference level in the context of diagnosis is the level present in a normal healthy subject. The term "normal healthy subject" refers to a subject who has no symptoms of any diseases or disorders, or who is not identified with any diseases or disorders, or who is not on any medication treatment, or a subject who is identified as healthy by physicians based on medical examinations. In some embodiments, a reference level or sample used herein refers to the level measured at a previous time point from a subject being treated.

The terms "treat", "treatment" and "treating" used interchangeably, with respect to treatment of a disease or disorder, mean preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis in a subject who is at risk of the disease, as well as slowing or reducing progression of existing disease. The term treating encompasses reducing or alleviating at least one adverse effect or symptom of a condition, disease or disorder associated with inappropriate ribosomal protein function. As used herein with respect to a ribosomal protein disorder, the term treating is used to refer to the reduction of a symptom and/or a biochemical marker of a ribosomal protein disorder by at least 10%., for example an increase of p21 expression levels in CD34+ cells in the subject, or a return of hemoglobin back to normal levels. For example but are not limited to, a increase of p21 in CD34+ cells in the subject, as an illustrative example only, by 10%, would be considered effective treatments by the methods as disclosed herein.

As used herein, the term "treating" includes preventing the progression and/or reducing or reversing at least one adverse effect or symptom of a condition, disease or disorder associated with a ribosomal protein disorder or ribosomopathy, for example, DBA. Accordingly, in some embodiments, treatment can be prophylactic in terms of completely or partially preventing a disease or sign or symptom of a ribosomal protein disorder or ribosomopathy. For example, subjects known to have a mutation in ribosomal protein or alternatively, low expression levels of a specific ribosomal protein, can be subjected to prophylactic treatment to prevent the onset of one or more symptoms associated with such a mutation in the ribosomal protein, and/or decreased levels in the ribosomal protein. In some embodiments, prophylactic treatment can be administered to subjects who had prior treatment of a disease associated with a ribosomal protein disorder. For example, for subjects who have received corticosteroids or blood transfusions for the treatment of DBA and/or other previous treatment to stabilize their DBA can be prophylactically treated (e.g. with a autophagy modulators as disclosed herein).

As used herein, the terms "prevent," "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the complete avoidance or prevention of symptoms or markers, but also a reduced severity or degree of any one of those symptoms or markers, relative to those symptoms or markers arising in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

The term "prophylactic" or "therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

Hematopoietic stem cells refer to a subset of multipotent stem cells that give rise to all the blood or immune cell types, including myeloid (monocytes and macrophages, neutrophils, basophils, eosinophils, erythrocytes, megakaryocytes/platelets, dendritic cells), and lymphoid lineages (T-cells, B-cells, NKT-cells, NK-cells). "Stem cells," as used herein, refer to cells that retain the ability to renew themselves through mitotic cell division and can differentiate into a diverse range of specialized cell types. The two broad types of mammalian stem cells are: embryonic stem (ES) cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

Accordingly, "hematopoietic stem cells," or "HSCs," as the terms are used herein, encompass all multipotent cells capable of differentiating into all the cell types of the hematopoietic system, including, but not limited to, granulocytes, monocytes, erythrocytes, megakaryocytes, B-cells and T-cells, and having multi-lineage hematopoietic differentiation potential and sustained self-renewal activity. "Self-renewal" refers to the ability of a cell to divide and generate at least one daughter cell with the identical (e.g., self-renewing) characteristics of the parent cell. The second daughter cell may commit to a particular differentiation pathway. For example, a self-renewing hematopoietic stem cell divides and forms one daughter stem cell and another daughter cell committed to differentiation in the myeloid or lymphoid pathway. In contrast, a committed progenitor cell has typically lost the self-renewal capacity, and upon cell division produces two daughter cells that display a more differentiated (i.e., restricted) phenotype. True hematopoietic stem cells have the ability to regenerate long term multi-lineage hematopoiesis (e.g., "long-term engraftment" or "hematopoietic multipotency") in individuals receiving a bone marrow or umbilical cord blood transplant, as described herein.

Hematopoietic stem cells arc traditionally identified as being lineage marker negative, Seal-positive, cKit-positive (or "LSK cells"), CD34-negative, Flk2-negative, CD48-negative, and CD150 positive. HSCs give rise to "multipotent progenitor cells" or "hematopoietic progenitor cells," which, as the terms are used herein, refer to a more differentiated subset of multipotent stem cells that are committed to the hematopoietic cell lineage but generally do not self-renew. The terms "hematopoietic progenitor cells" or "multi-potent progenitor cells" (MPPs) encompass short term hematopoietic stem cells (also known as ST-HSCs, which are lineage marker negative, Seal-positive, cKit-positive, CD34-positive, and Flk2-negative); common myeloid progenitor cells (CMPs); lymphoid-primed progenitor cells (LMPPs), granulocyte-monocyte progenitor cells (GMPs), and megakaryocyte-erythrocyte progenitor cells (MEPs). Hematopoietic stem cells subsets are sometimes also identified and discriminated on the basis of additional cell-surface marker phenotypes, such as by using combinations of members of the SLAM family, or the "SLAM phenotype," such as, long-term multi-lineage repopulating and self-renewing hematopoietic stein cells (HSCs): CD150+CD48-CD244-; MPPs: CD150-CD48-CD244+; lineage-restricted progenitor cells (LRPs): CD150-CD48+CD244+; common myeloid progenitor cells (CMP): lin-SCA-1-c-kit+CD34+CD16/32mid; granulocyte-macrophage progenitor (GMP): lin-SCA-1-c-kit+CD34+CD16/32hi; and megakaryocyte-erythroid progenitor (MEP): lin-SCA-1-c-kit+CD34+CD16/32low.

As used herein, the term "population of hematopoietic cells" encompasses a heterogeneous or homogeneous population of hematopoietic stem cells and/or hematopoietic progenitor cells. In addition, differentiated hematopoietic cells, such as lymphocytes, can be present in a population of hematopoietic cells. A population of hematopoietic cells comprising at least two different cell types is referred to herein as a "heterogeneous population." A population of hematopoietic cells comprising only one cell type (e.g., hematopoietic stem cells expressing a hematopoietic stem cell identifier molecule under the operative control of the endogenous Fdg5 locus) is referred to herein as a "homogeneous population of cells."

As used herein, the term "autophagy activator" is in reference to a small molecule that activates autophagy in a cell by any mechanism. For example, Apicidin induces autophagy via inhibition of histone deacetylase; Brefeldin A, Tunicamycin, and Thapsigargin induces autophagy via the induction of ER stress, Rapamyocin and Torin inhibit mTOR signaling to activate autophagy, and SMER28 enhances A53T alpha-synuclein clearance to activate autophagy.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "gene product(s)" as used herein refers to include RNA transcribed from a gene, or a polypeptide encoded by a gene or translated from RNA.

The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease" or "inhibition" is used in the context of the level of expression or activity of a gene or a protein, it refers to a reduction in protein or nucleic acid level or activity in a cell, a cell extract, or a cell supernatant. For example, such a decrease may be due to reduced RNA stability, transcription, or translation, increased protein degradation, or RNA interference The terms "up-regulate", "increase" or "activate" are all used herein to generally mean an increase by a staticly significant amount; for the avoidance of any doubt, the terms "up-regulate", "increase" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or a 100% increase or more, or any increase between 10-100% as compared to a reference level, or an increase greater than 100%, for example, an increase at least about a 2-fold, or at least about a 3-fold, or at least about a 4-fold, or at least about a 5-fold or at least about a 10-fold increase, or any increase between 2-fold and 10-fold or greater as compared to a reference level. When "increase" is used in the context of the expression or activity of a gene or protein, it refers to a positive change in protein or nucleic acid level or activity in a cell, a cell extract, or a cell supernatant. For example, such an increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions. In some embodiments, an autophagy modulator which is a small-molecule as disclosed herein can activate autophagy. Preferably, this increase is at least about 5%, at least about 10%, at least about 25%, at least about 50%, at least about 75%, at least about 80%, or even at least about 90% of the level of expression or activity under control conditions.

The terms "significantly different than,", "statistically significant," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

A "pharmaceutical composition" refers to a chemical or biological composition suitable for administration to a mammalian subject. Such compositions may be specifically formulated for administration via one or more of a number of routes, including but not limited to, oral, parenteral, intravenous, intraarterial, subcutaneous, intranasal, sublingual, intraspinal, intracerebroventricular, and the like.

The term "effective amount" is used interchangeably with the term "therapeutically effective amount" and refers to the amount of at least one agent, e.g., autophagy activator of a pharmaceutical composition, at dosages and for periods of time necessary to achieve the desired therapeutic result, for example, to reduce or stop at least one symptom of the ribosomal disorder or ribosomopathy, for example a symptom of high levels of p21 in CD34+ cells in the subject. For example, an effective amount using the methods as disclosed herein would be considered as the amount sufficient to reduce a symptom of the ribosomal disorder or ribosomopathy by at least 10%. An effective amount as used herein would also include an amount sufficient to prevent or delay the development of a symptom of the disease, alter the course of a symptom disease (for example but not limited to, slow the progression of a symptom of the disease), or reverse a symptom of the disease. Accordingly, the term "effective amount" or "therapeutically effective amount" as used herein refers to the amount of therapeutic agent (e.g. at least one autophagy modulator as disclosed herein) of pharmaceutical composition to alleviate at least one symptom of a ribosomal disorder or ribosomopathy, e.g. DBA. Stated another way, "therapeutically effective amount" of a autophagy activator as disclosed herein is the amount of a autophagy activator which exerts a beneficial effect on, for example, the symptoms of the ribosomal disorder or ribosomopathy. The dosage administered, as single or multiple doses, to an individual will vary depending upon a variety of factors, including pharmacokinetic properties of the autophagy modulator, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify the a autophagy modulator as disclosed herein which will achieve the goal of reduction in the severity of at least one symptom of a ribosomal protein disease or disorder or ribosomopathy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

The terms "administered" and "subjected" are used interchangeably in the context of treatment of a disease or disorder. Both terms refer to a subject being treated with an effective dose of pharmaceutical composition comprising an autophagy modulator of the invention by methods of administration such as parenteral or systemic administration.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of a pharmaceutical composition comprising at least an autophagy modulator as disclosed herein such that it enters the animal's system and, thus, is subject to metabolism and other like processes, for example, subcutaneous administration.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "optional" or "optionally" means that the subsequent described event, circumstance or substituent may or may not occur, and that the description includes instances where the event or circumstance occurs and instances where it does not.

The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a pharmaceutical composition comprising "an agent" includes reference to two or more agents.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of elements that do not materially affect the basic and novel or functional characteristic(s) of that embodiment of the invention.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

The term "enantiomer" is used to describe one of a pair of molecular isomers which are mirror images of each other and non-superimposable. The designations may appear as a prefix or as a suffix; they may or may not be separated from the isomer by a hyphen; they may or may not be hyphenated; and they may or may not be surrounded by parentheses. The designations "(+)" and "(−)" are employed to designate the sign of rotation of plane-polarized light by the compound, with (−) meaning that the compound is levorotatory (rotates to the left). A compound prefixed with (+) is dextrorotatory (rotates to the right). Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in *E. B. Roche ed. Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11, 345-365; Gaignault et al. (1996) "Designing Prodrugs and Bioprecursors I. Carrier Prodrugs," *Pract. Med. Chem.* 671-696; Asgharnejad, "Improving Oral Drug Transport", in Transport Processes in Pharmaceutical Systems, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs-principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [Symp.] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.*: 39(1-3):63-80 (1999); Waller et al., "Prodrugs", *Br. J. Clin. Pharmac.* 28: 497-507 (1989), content of all of which is herein incorporated by reference in its entirety.

Dosage Forms

The dosages to be administered can be determined by one of ordinary skill in the art depending on the clinical severity of the disease, the age and weight of the patient, the exposure of the patient to conditions that may precipitate outbreaks of psoriasis, and other pharmacokinetic factors generally understood in the art, such as liver and kidney metabolism. The interrelationship of dosages for animals of various sizes and species and humans based on mg/m$^3$ of surface area is described by E. J. Freireich et al., "Quantitative Comparison of Toxicity of Anticancer Agents in Mouse, Rat, Hamster, Dog, Monkey and Man," Cancer Chemother. Rep. 50: 219-244 (1966). Adjustments in the dosage regimen can be made to optimize the therapeutic response. Doses can be divided and administered on a daily basis or the dose can be reduced proportionally depending on the therapeutic situation.

Typically, these drugs will be administered orally, and they can be administered in conventional pill or liquid form. If administered in pill form, they can be administered in conventional formulations with excipients, fillers, preservatives, and other typical ingredients used in pharmaceutical formations in pill form. Typically, the drugs are administered in a conventional pharmaceutically acceptable formulation, typically including a carrier. Conventional pharmaceutically acceptable carriers known in the art can include alcohols, e.g., ethyl alcohol, serum proteins, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and conventional anti-bacterial or anti-fungal agents, such as parabens, chlorobutanol, phenol, sorbic acid, thimerosal, and the like. A pharmaceutically-acceptable carrier within the scope of the present invention meets industry standards for sterility, isotonicity, stability, and non-pyrogenicity.

The pharmaceutically acceptable formulation can also be in pill, tablet, or lozenge form as is known in the art, and can include excipients or other ingredients for greater stability or acceptability. For the tablets, the excipients can be inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc, along with the substance for autophagy modulation and other ingredients.

The drugs can also be administered in liquid form in conventional formulations, that can include preservatives, stabilizers, coloring, flavoring, and other generally accepted pharmaceutical ingredients. Typically, when the drugs are administered in liquid form, they will be in aqueous solution. The aqueous solution can contain buffers, and can contain alcohols such as ethyl alcohol or other pharmaceutically tolerated compounds.

Alternatively, the drugs can be administered by injection by one of several routes well known in the art. It is, however, generally preferred to administer the drugs orally.

The drugs can be administered from once per day to up to at least five times per day, depending on the severity of the disease, the total dosage to be administered, and the judgment of the treating physician. In some cases, the drugs need not be administered on a daily basis, but can be administered every other day, every third day, or on other such schedules. However, it is generally preferred to administer the drugs daily.

Autophagy Activator

In most cells, autophagy occurs at low levels and is often induced to confer stress resistance and sustain cellular survival under adverse conditions. Mutations in the autophagic machinery components are associated with a number of human disorders, e.g., ribosomal disorders, cardiomyopathies, infectious diseases, Crohn's disease, and neurodegenerative disorders including Alzheimer's, Huntington's, and Parkinson's diseases. Small molecules that activate autophagy in cells has been shown to reverse disease states, as well as promote longevity in the cell. Autophagy activators have been shown to reduce the amount of toxic protein aggregates and promote cell survival under stress. Exemplary autophagy activators include, e.g., A23187, Amiodarone hydrochloride, Apicidin, Brefeldin A, Carbamazepine, Clonidine hydrochloride, Dexamethasone, Dorsomorphin dihydrochloride, EB 1089, FK 866 hydrochloride, GF 109203X, GPP 78 hydrochloride, L-690,330, NF 449, Niclosamide, Nimodipine, Nitrendipine, 3-Nitropropionic acid, Perifosine, PI 103 hydrochloride, Pifithrin-α hydrobromide, Rapamycin, Rilmenidine hemifumarate, Rottlerin, Salirasib, SMER28, Temozolomide, Thapsigargin, Torin 1, Tunicamycin, Valproic acid, Verapamil hydrochloride SMER28 is a small molecule modulator of mammalian autophagy. Enhances A53T alpha-synuclein clearance in PC-12 cells independent of rapamycin treatment and appears to act independent of the mTOR pathway, but combined treatment with saturating rapamycin concentration enhances the effect of either compound alone on A53T alpha-synuclein clearance. SMER28 also augments the cytostatic effects of Rapamycin in *Saccharomyces cerevisiae* and acts as an autophagy stimulator in mammalian cultures in vitro. Although SMER28 and Rapamycin do exhibit additive effects on the clearance of cellular autophagy substrates, SMER28 functions independently of Rapamycin by presumably acting on celluar target(s) downstream of the Rapamycin/FKBP12 target, mTOR.

All autophagy activators as disclosed herein are provided herein for illustrative purpose and disclose a particular isomer. However, one of ordinary skill in the art will recognize all possible isomers of the structures of any of the formulas of the autophagy activator, e.g., A-3, W-7, A-7, W-5 and CGS-9343. Therefore, other isomers and derivatives such as enantiomers of any of formulas of A-3, W-7, A-7, W-5 are considered to fall within the scope of the invention. As used herein, the term "isomer" refers to a compound having the same molecular formula but differing in structure. Isomers which differ only in configuration and/or conformation are referred to as "stereoisomers." The term "isomer" is also used to refer to an enantiomer.

In various embodiments, autophagy activators as disclosed herein include enantiomers, derivatives, prodrugs, and pharmaceutically acceptable salts thereof.

In some embodiments, prodrugs of autophagy activators are disclosed herein also fall within the scope of the invention. As used herein, a "prodrug" refers to a compound that can be converted via some chemical or physiological process (e.g., enzymatic processes and metabolic hydrolysis) to a functionally active autophagy activator.

Autophagy activators as disclosed herein also include pharmaceutically acceptable salts thereof. As used herein, the term "pharmaceutically-acceptable salts" refers to the conventional nontoxic salts or quaternary ammonium salts of autophagy activators as disclosed herein, e.g., from non-toxic organic or inorganic acids. These salts can be prepared in situ in the administration vehicle or the dosage form manufacturing process, or by separately reacting a autophagy activator in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", J. Pharm. Sci. 66:1-19 (1977), content of which is herein incorporated by reference in its entirety.

In some embodiments of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Use of the Autophagy Activators to Treat Ribosomal Disorders and Ribosomopathies In some embodiments, an autophagy activators as disclosed herein can be used to treat various disease and disorders associated with ribosomal proteins or ribosomopathies. For instance, the autophagy activators can be used to treat a subject who has a mutation in one or more ribosomal proteins, or have a decreased level of the ribosomal protein.

In some embodiments, the autophagy activators as disclosed herein can be used in a method of treating a subject with a ribosomal disorder such as Diamond Blackfan Anemia (DBA). There are a variety of types of Diamond Blackfan anemeia, for example, where the subject has DBA1, DBA2, DBA3, DBA4, DBA5, DBA6, DBA7, or DBA8. Diamond Blackfan anemia (DBA), also known as Blackfan-Diamond anemia and Inherited erythroblastopenia, is a congenital erythroid aplasia that usually presents in infancy. DBA patients have low red blood cell counts (anemia). The rest of their blood cells (the platelets and the white blood cells) are normal. This is in contrast to Shwachman-Bodian-Diamond syndrome, in which the bone marrow defect results primarily in neutropenia, and Fanconi anemia, where all cell lines are affected resulting in pancytopenia. A variety of other congenital abnormalities may also occur. Diamond Blackfan anemia is characterized by anemia (low red blood cell counts) with decreased erythroid progenitors in the bone marrow. This usually develops during the neonatal period. About 47% of affected individuals also have a variety of congenital abnormalities, including craniofacial malformations, thumb or upper limb abnormalities, cardiac defects, urogenital malformations, and cleft palate. Low birth weight and generalized growth delay are sometimes observed. DBA patients have a modest risk of developing leukemia and other malignancies.

Typically, a diagnosis of DBA is made through a blood count and a bone marrow biopsy. A diagnosis of DBA is made on the basis of anemia, low reticulocyte (immature red blood cells) counts, and diminished erythroid precursors in bone marrow. Features that support a diagnosis of DBA include the presence of congenital abnormalities, macrocytosis, elevated fetal hemoglobin, and elevated adenosine deaminase levels in red blood cells. Most patients are diagnosed in the first two years of life. However, some mildly affected individuals only receive attention after a more severely affected family member is identified. About 20-25% of DBA patients may be identified with a genetic test for mutations in the RPS19 gene. Approximately 10-25% of DBA cases have a family history of disease, and most pedigrees suggest an autosomal dominant mode of inheritance.

Accordingly, in some embodiments, the autophagy modulators as disclosed herein can be used in a method of treating a subject that has a mutation in ribosomal protein 19 (RPS19). The phenotype of DBA patients indicates a hematological stem cell defect specifically affecting the erythroid progenitor population. The RPS19 protein is involved in the production of ribosomes. Disease features may be related to the nature of RPS19 mutations. The disease is characterized by dominant inheritance, and therefore arises due to a partial loss of RPS19 protein function. I In alternative embodiments, the autophagy activators as disclosed herein can be used in a method of treating a subject with a mutation in ribosomal protein from at least one of, but not limited to RPS7, RPS10, RPS19, RPS24, PRS26, RPS17, RPS27L, RPS29, RPL35A, RPL5 and RPL11. For example, a mutation or variant in RPS19 causes DBA1, and a mutation or variant in RPS24 causes DBA3, a mutation or variant in RPS17 causes DBA4, a mutation or variant in RPS34A causes DBA5, a mutation or variant in RPL5 causes DBA6, a mutation or variant in RPL11 causes DBA7, and a mutation or variant in RPS7 causes DBA8.

In some embodiments of all aspects of the present invention, the method further comprises administering another therapeutic agent to treat the ribosomal protein defect. The additional therapeutic can be selected from the group consisting of: corticosteroids, blood transfusions and bone marrow transplants and other treatments known to persons of ordinary skill in the art. Corticosteroids can be used to treat anemia in DBA. Blood transfusions can also be used to treat severe anemia in DBA. Periods of remission may occur, during which transfusions and steroid treatments are not required. Bone marrow transplantation (BMT) can cure hematological aspects of DBA, adverse events in transfusion patients can occur (Diamond Blackfan Anemia Foundation; Pospisilova D et al., (2007). "Successful treatment of a Diamond-Blackfan anemia patient with amino acid leucine. Haematologica 92 (5): e66.)

In some embodiments of all aspects of the present invention, autophagy activators administered to the subject increases the number of CD71+ erythroid cells in the subject and/or increases hemoglobin levels in the subject.

In some embodiments of all aspects of the present invention, the methods and autophagy activators as disclosed herein can be used to treat a subject with a ribosomal disorder, such as DBA has a symptom of macrocytic anemia and/or craniofacial abnormalities.

In another embodiment, an autophagy activator as disclosed herein can be used in a method of treating a subject with a ribosomal disorder such as myelodysplasia, for example, but not limited to 5q-myelodysplasia (5q syndrome). Myelodysplasia or myelodysplastic syndromes (MDS, formerly known as preleukernia) are a diverse collection of hematological (blood-related) medical conditions that involve ineffective production (or dysplasia) of the myeloid class of blood cells, and where the bone marrow does not function normally and produces insufficient number of normal blood cells.

Patients with MDS often develop severe anemia and require frequent blood transfusions. In most cases, the disease worsens and the patient develops cytopenias (low blood counts) caused by progressive bone marrow failure. In about one third of patients with MDS, the disease transforms into acute myelogenous leukemia (AML), usually within months to a few years.

The myelodysplastic syndromes are all disorders of the stem cell in the bone marrow. In MDS, hematopoiesis (blood production) is disorderly and ineffective. The number and quality of blood-forming cells decline irreversibly, further impairing blood production.

MDS affects the production of any, and occasionally all, types of blood cells including red blood cells, platelets, and white blood cells (cytopenias). About 50 percent of pediatric myelodysplasia can be classified in five types of MDS: refractory anemia, refractory anemia with ring sideroblasts, refractory anemia with excess blasts, refractory anemia with excess blasts in transformation, and chronic myelomonocytic leukemia. The remaining 50 percent typically present with isolated or combined cytopenias such as anemia, leucopenia and/or thrombocytopenia (low platelet count). Although chronic, MDS progresses to become acute myeloid leukemia (AML) in about 30 percent of patients.

5q-myelodysplasia, (also known as 5q-syndrome) is a rare disorder caused by loss of part of the long arm (q arm, band 5q31.1) of human chromosome 5. 5q-myelodysplasia is characterized by macrocytic anemia often thrombocytosis, erythroblastopenia, megakaryocyte hyperplasia with nuclear hypolobation and an isolated interstitial deletion of chromosome 5. The 5q-syndrome is found predominantly in females of advanced age.

Some subjects with 5q-myelodysplasia have a decrease in Rps14 expression. Deletion of the miR-145 and miR-146 loci has been associated with elevated platelet count and megakaryocytic dysplasia associated with the 5q-syndrome. 5q-myelodysplasia affects bone marrow cells causing treatment-resistant anemia and myelodysplastic syndromes that may lead to acute myelogenous leukemia. Examination of the bone marrow shows characteristic changes in the megakaryocytes. They are more numerous than usual, small and mononuclear. There may be accompanying erythroid hypoplasia in the bone marrow. Accordingly, in some embodiments, a subject with 5q-myelodysplasia can have dysplastic bone marrow. Subjects with 5q-myelodysplasia can be treated with Lenalidomide (Bennett J et al. (2006). "Lenalidomide in the myelodysplastic syndrome with chromosome 5q deletion". N. Engl. J. Med. 355 (14): 1456-65; Raza et al., (2008), "Phase 2 study of lenalidomide in transfusion-dependent, low-risk, and intermediate-1 risk myelodysplastic syndromes with karyotypes other than deletion 5q". Blood 111 (1): 86-93.)

The median age at diagnosis of a MDS is between 60 and 75 years; a few patients are younger than 50; MDS diagnoses are rare in children. Males are slightly more commonly affected than females. Signs and symptoms are nonspecific and generally related to the blood cytopenias include, but are not limited to: (a) Anemia (low RBC count or reduced hemoglobin)—chronic tiredness, shortness of breath, chilled sensation, sometimes chest pain, (b) Neutropenia (low neutrophil count)—increased susceptibility to infection, (c) Thrombocytopenia (low platelet count)—increased susceptibility to bleeding and ecchymosis (bruising), as well as subcutaneous hemorrhaging resulting in purpura or petechial. Many individuals are asymptomatic, and blood cytopenia or other problems are identified as a part of a routine blood count: neutropenia, anemia and thrombocytopenia (low cell counts of white and red blood cells, and platelets, respectively); splenomegaly or rarely hepatomegaly; abnormal granules in cells, abnormal nuclear shape and size; and/or chromosomal abnormalities, including chromosomal translocations and abnormal chromosome number. Although there is some risk for developing acute myelogenous leukemia, about 50% of deaths occur as a result of bleeding or infection. Leukemia that occurs as a result of myelodysplasia is notoriously resistant to treatment.

In aspect of the present invention, the methods and autophagy activators as disclosed herein can be used to treat a subject with anemia. In one embodiment, a subject has treatment-related anemia due to treatment for another disorder such as cancer or dysplasia which include myelosuppression, chemotherapy, immunosuppression, or radiation therapy.

In some embodiments of all aspects of the present invention, the methods and autophagy activators as disclosed herein can be used to treat a subject with a ribosomopathy such as Shwachman-Diamond syndrome, for example, where the subject has a mutation in Sbds. In some embodiments, a subject with Shwachman-Diamond syndrome has one or more symptoms selected from pancreatic insufficiency, bone marrow dysfunction, skeletal deformities.

In another embodiment, autophagy activators as disclosed herein can be used in a method of treating a subject with a ribosomopathy such as Treacher Collins Syndrome, for example, where the subject has a mutation in TCOFI (nucleolar). Treacher-Collins syndrome is a condition that is passed down through families (hereditary) that leads to problems with the structure of the face. Treacher-Collins syndrome is caused by a defective protein called treacle. The condition is passed down through families (inherited). This condition may vary in severity from generation to generation and from person to person. Symptoms of Treacher-Collins syndrome include at least one of, but are not limited to: abnormal or almost completely missing outer part of the ears, hearing loss, very small jaw (micrognathia), very large mouth, defect in the lower eyelid (coloboma), scalp hair that reaches to the cheeks, cleft palate. Accordingly, a subject with Treacher Collins Syndrome has one or more craniofacial deformities. While a child with Treacher Collins Syndrome usually will show normal intelligence, diagnosis can be made on the bases of an examination of the infant which may reveal a variety of problems, including: (a) Abnormal eye shape, (b) Flat cheekbones, (c) Clefts in the face, (d) Small jaw, (e) Low-set ears, (f) Abnormally formed ears, (g) Abnormal ear canal, (h) Hearing loss, (i) Defects in the eye (coloboma that extends into the lower lid), (j) Decreased eyelashes on the lower eyelid, (k) genetic tests can help identify gene changes linked to this condition. The diagnosis of Treacher Collins Syndrome also relies upon clinical and radiographic findings, and there is a set of typical symptoms within Treacher Collins Syndrome which can be detected by a critical clinical view. The wide spectrum of diseases which have similar characteristics make it sometimes difficult to diagnose TCS. The OMENS classification was developed as a comprehensive and stage-based approach to differentiate the diseases. This acronym describes five distinct dysmorphic manifestations, namely O; orbital asymmetry, M; mandibular hypoplasia, E; auricular deformity, N; nerve development and S; soft-tissue disease.

Pharmaceutical Compositions Comprising an Autophagy Activator

Another aspect of the present invention relates to pharmaceutical compositions for treatment of diseases or disorders associated with ribosomal proteins or dysfunction or where a subject has a ribosomopathy, e.g., DBA, myelodysplasia, for example, but not limited to 5q syndrome, Shwachman-Diamond syndrome and Treacher Collins Syndrome. In some embodiments, a pharmaceutical composition of the invention comprises a therapeutically effective amount of at least one autophagy activator as disclosed herein. In one embodiment, an autophagy activator is, for example, but not limited to, a quinazolinamine compound, e.g., SMER28.

An autophagy activator as disclosed herein can be used in an amount of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some embodiments, an autophagy activator can be used in an amount of about 0.1 to 1000 µg/kg of body weight or about 1 to 100 µg/kg of body weight or about 10 to 50 µg/kg of body weight. In some embodiments, an autophagy activator as disclosed herein can be used at a concentration of about 0.001 mg/ml or 0.1 mg/ml or a higher concentration of 0.1 mg/ml. In some embodiments, a pharmaceutical composition comprises at least one autophagy activator at a concentration of about 0.01 µM to 300 µM, or about 0.1 µM to 150 µM, or about 1 µM to 50 µM, or about 1 µM to 25 µM. The dosage may vary within this range depending upon the dosage form employed and the route of administration utilized.

Depending on routes of administration, one of skill in the art can determine and adjust an effective dosage of an autophagy activator disclosed herein to a subject such as a human subject accordingly, by determining pharmacokinetics and bioavailability of an autophagy modulator and analyzing dose-response relationship specific to an autophagy activator in animal models such as a mouse.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

The data obtained from the cell culture assays and animal studies can be used in formulating a range of dosage for use in humans. The therapeutically effective dose can be determined by one of ordinary skill in the art, e.g. using cell culture assays. A dose can be formulated in animal models to achieve a circulating plasma concentration range that includes the IC50 (i.e., the concentration of the therapeutic which achieves a half-maximal inhibition of symptoms) as determined by methods disclosed in the Examples. An effective dose of an autophagy activator can be determined in an animal model by measuring the levels of hemoglobin over the course of treatment with an autophagy activator as compared to no treatment. In some embodiments, a dosage comprising an autophagy activator is considered to be effective if the dosage increases hemoglobin levels, red cell number, and/or reduces expression of p2l in CD34+ cells by at least about 15%, at least about 20%, at least about 30%, at least about 40%, at least about 50%, at least about 60%, at least about 70%, at least about 80%, at least about 90%, 95%, 99% or even 100%, as compared to a control (e.g. in the absence of an autophagy activator). In some embodiments, a therapeutically effective amount of an autophagy activator administered to a subject is dependent upon factors known to a person of ordinary skill, including bioactivity and bioavailability of an autophagy activator (e.g. half-life and stability of an autophagy activator in the body), chemical properties of an autophagy activator (e.g. molecular weight, hydrophobicity and solubility); route and frequency of administration, time of administration (e.g. before or after a meal), and the like. Further, it will be understood that the specific dose of the pharmaceutical composition comprising an autophagy activator as disclosed herein to provide the therapeutic or prophylactic benefits can depend on a variety of factors including physical condition of the subject (e.g. age, gender, weight), medical history of the subject (e.g. medications being taken, other diseases or disorders) and clinical condition of the subject (e.g. health condition, stage of the disease). The precise dose of a pharmaceutical composition comprising an autophagy activator can be determined by methods known to a skilled artisan such as pharmacologists and physicians.

According to the invention, an autophagy activator as disclosed herein can be administered prophylactically or therapeutically to a subject prior to, simultaneously or sequentially with other therapeutic regimens or agents (e. g. multiple drug regimens), in a therapeutically effective amount. In some embodiments, an autophagy activator administered concurrently with other therapeutic agents can be administered in the same or different compositions. Additional therapeutic agents or regimens include, but are not limited to, steroids, corticosteroids, blood transfusions and bone marrow transplants.

The active ingredients (e.g. an autophagy activator) of the pharmaceutical composition according to the invention can be administered to an individual by any route known to persons skilled in the art. The routes of administration include intradermal, transdermal (e.g. in slow release formulations), intramuscular, intraperitoneal, intravenous, subcutaneous, oral, buccal, nasal, rectal, epidural, topical, intrathecal, rectal, intracranial, intratracheal and intrathecal and intranasal routes. Any other therapeutically efficacious route of administration can be used, for example absorption through epithelial or endothelial tissues or systemic administration. In addition, an autophagy activator according to the invention can be administered together with other components of biologically active agents such as pharmaceutically acceptable surfactants, excipients, carriers, diluents and vehicles.

For parenteral (e.g. intravenous, subcutaneous, intramuscular) administration, an autophagy activator can be formulated as a solution, suspension, emulsion or lyophilized powder in association with a pharmaceutically acceptable parenteral vehicle (e.g. water, saline, dextrose solution) and additives that maintain isotonicity (e g. mannitol) or chemical stability (e.g. preservatives and buffers). The formulation is sterilized by commonly used techniques.

In some embodiments, the route of administration is administration by subcutaneous route. Intramuscular administration is another alternative route of administration. In some embodiments, a pharmaceutical composition comprising an autophagy activator can be administered as a formulation adapted for systemic delivery. In some embodiments, the compositions can be administered as a formulation adapted for delivery to specific organs, for example but not limited to the liver. In some embodiments, a pharmaceutical composition comprising an autophagy activator as disclosed herein can be administered as a formulation adapted not to pass through the blood-brain barrier.

Alternatively, in some embodiments, a pharmaceutical composition can be incorporated in a gel, sponge, or other permeable matrix (e.g., formed as pellets or a disk) and placed in proximity to the liver endothelium for sustained, local release. The composition comprising an autophagy activator can be administered in a single dose or in multiple doses, which are administered at different times.

The exact route of administration as well as the optimal dosages can be determined by standard clinical techniques for each specific case, mainly based on the nature of the disease or disorder and on the stage of this disease. Preferably, the medicament according to the present invention is applied locally or systemically, in particular, orally, intravenously, parenterally, epicutaneously, subcutaneously, intrapulmonarily by inhalation or bronchoalveolar lavage, intramuscularily, intracranially, locally into intervertebral discs or other connective tissues.

As disclosed herein, a pharmaceutical composition comprising an effective amount of at least one autophagy activator can be administered to a subject for the therapeutic treatment or prevention (e.g. prophylactic treatment) of ribosomal diseases and disorders or ribosomopathies.

In some embodiments, a composition of the invention comprising an autophagy activator as disclosed herein is formulated for ribosomal diseases and/or ribosomophaties, e.g. DBA, myelodysplasia, for example, but not limited to 5q Syndrome, Shwachman-Diamond syndrome and Treacher Collins Syndrome. In one embodiment, an autophagy activator as disclosed herein is a derivative, analogue, prodrug, or pharmaceutically acceptable salts thereof.

In some embodiments, a pharmaceutical composition comprising at least one autophagy activator further comprises a second therapeutic agent. In one embodiment, the second therapeutic agent is but not limited to a corticosteroid.

In prophylactic applications, pharmaceutical compositions (or medicaments) comprising an autophagy activator can be administered to a subject susceptible to, or otherwise at risk of, a ribosomal disease or disorder and/or ribosomopathy in an amount sufficient to eliminate or reduce the risk or delay the onset of the disease. In one embodiment, a pharmaceutical composition of the invention disclosed herein comprises an autophagy activator, or enantiomers, prodrugs, derivatives or pharmaceutically acceptable salts thereof.

In therapeutic applications, according to the invention provided herein, when an effective amount or effective dose of a pharmaceutical composition comprising an autophagy modulator as disclosed herein can be administered to the subject with a ribosomal disease or disorder and/or ribosomopathy so that at least one of the symptoms of such a ribosomal disease can be delayed or inhibited. In some embodiments, administration of an effective amount or effective dose of a pharmaceutical composition comprising an autophagy activator to a subject with a ribosomal disease or disorder and/or ribosomopathy can inhibit or delay progression of facial abnormalities, and/or other symptoms associated with the ribosomal disease or ribosomopathy. In further embodiments, treating subjects with an effective dose of a pharmaceutical composition comprising an autophagy activator can prevent or delay a symptom of the ribosomal disease or ribosomopathy in the subject.

In some embodiments, the present invention also provides compositions an autophagy activator as discussed herein for practicing the therapeutic and prophylactic methods described herein. In some embodiments, combinations of an autophagy activator and another therapeutic agent can be tailored to be combined in a pharmaceutical composition, where each therapeutics can target a different symptom, a different disease or a different disorder. In further embodiments, an autophagy activator and another therapeutic can be mixed together in a pharmaceutical composition as disclosed herein. In other embodiments, an autophagy activator and another therapeutic can be present in a different formulation when combined in a pharmaceutical composition. For example, in one embodiment, an autophagy activator can be present in a liquid formulation, while another therapeutic can be lypholized into powder. The formulations of different active ingredients in a pharmaceutical composition as disclosed herein (e.g. an autophagy activator and/or another therapeutics) can be optimized accordingly by various factors such as physical and chemical properties of a drug, bioavailability, route of administration, and whether it is a sustained or a burst release for the drug. Therapeutic and prophylactic compositions of the present invention can further comprise a physiologically tolerable carrier together with an autophagy activator as disclosed herein, or derivatives, enantiomers, prodrugs or pharmaceutically acceptable salts thereof. In additional embodiments, an autophagy activator and another therapeutics can employ different physiologically tolerable carriers when combined in a pharmaceutical composition of the invention as disclosed herein.

In some embodiments, a pharmaceutical composition as disclosed herein comprises an autophagy activator together with other therapeutics and a pharmaceutically acceptable excipient. Suitable carriers for an autophagy activator of the invention, and their formulations, are described in Remington's Pharmaceutical Sciences, 22nd ed., 2013, Mack Publishing Co. Typically an appropriate amount of a pharmaceutically acceptable salt is used in the formulation to render the formulation isotonic. Examples of the carrier include buffers such as saline, Ringer's solution and dextrose solution. Further carriers include sustained release preparations such as semipermeable matrices of solid hydrophobic polymers, which matrices are in the form of shaped articles, e.g. liposomes, films or microparticles. It will be apparent to those of skill in the art that certain carriers can be more preferable depending upon for instance the route of administration and concentration of an autophagy activator being administered.

In some embodiments, bioavailability of an autophagy activator according to the invention can be also enhanced by encapsulating an autophagy activator in biocompatible delivery vehicles which increase the half-life of an autophagy activator in a human body. Exemplary biocompatible delivery vehicles include polymeric vehicles such as PEG-based vehicles, or liposome-based vehicles.

In some embodiments, an autophagy activator can be dissolved or dispersed as an active ingredient in the physiologically tolerable carrier to increase the half-life of an autophagy activator in a subject.

The preparation of a pharmacological composition that contains active ingredients (e.g. an autophagy activator) dissolved or dispersed therein is well understood in the art and need not be limited based on formulation. Typically such compositions are prepared as injectable either as liquid solutions or suspensions, however, solid forms suitable for solution or suspension in liquid prior to use can also be prepared. The preparation can also be emulsified or presented as a liposome composition. In some embodiments, an autophagy activator can be mixed with excipients which are pharmaceutically acceptable and compatible with the active ingredient and in amounts suitable for use in the therapeutic methods described herein. In addition, if desired, the composition comprising an autophagy activator can contain minor amounts of auxiliary substances such as wetting or emulsifying agents, pH buffering agents and the like which enhance the effectiveness of the active ingredient.

Physiologically tolerable carriers (i.e. physiologically acceptable carriers) are well known in the art. Selection of pharmaceutically acceptable carriers can be accomplished by means of administration by a skilled artisan. For example, if the composition is orally administered, it can be formulated in coated tablets, liquids, caplets and so forth. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. For topical application, the carrier may be in the form of, for example, and not by way of limitation, an ointment, cream, gel, paste, foam, aerosol, suppository, pad or gelled stick. In some embodiments, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997). An autophagy activator as disclosed herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

A skilled artisan will be able to determine the appropriate way of administering pharmaceutical compositions comprising at least one an autophagy activator as disclosed herein in view of the general knowledge and skill in the art.

Treatment Regimes

Another aspect of the present invention relates to methods for therapeutic and prophylactic treatment of diseases or disorders, where activation of autophagy is desirable for the treatment or prevention of a ribosomal disorder or a ribosomopathy. The methods comprise administering to a subject in need thereof a pharmaceutical composition comprising a therapeutically effective amount of at least one autophagy activator selected from for example, any, or a combination, of compounds such as SMER28 and analogues and variants as disclosed herein.

In one embodiment, Diamond-Blackfan anemia (DBA) is treated or prevented by the methods and compositions of the present invention with an autophagy activator as disclosed herein. In one embodiment the autophagy activator is SMER28.

Effective doses of the pharmaceutical composition comprising an autophagy activator as disclosed herein, for the treatment of ribosome protein diseases or disorders or associated with a ribosomopathy depend upon many different factors, including means of administration, physiological state of the subject, whether the subject is human or an animal, other medications administered, and whether treatment is prophylactic or therapeutic. Depending on the clinical condition of a subject, dosage and frequency of pharmaceutical compositions of the present invention can be adjusted accordingly over time by one of the skill in the art, e.g. physicians.

In therapeutic applications, a relatively high dosage in relatively short intervals is sometimes required until progression of the disease is reduced or terminated, or until the subject shows partial or complete amelioration of symptoms of disease. Thereafter, the subject can be administered a prophylactic regime. For example, subjects with DBA can be treated with an autophagy activator as disclosed herein at an effective dose in a therapeutic regimen accordingly to decrease the p21 levels back to a normal level, and then be administered a maintenance dose, e.g., prophylactically. In some embodiments an autophagy activator as disclosed herein can be administered to subjects prior to, concurrently with, or sequentially to treatment with a corticosteroid, and/or when the subject us undergoing an adjuvant therapy, such as a blood transfusion and/or bone marrow transplant. In some embodiments for example, a DBA subject which is selected for other therapeutic procedures or surgeries, such as blood transfusions and/or bone marrow transplant, can be subjected to a treatment with an autophagy activator as disclosed herein. For example, a pharmaceutical composition of the invention can be administered prior to, during or after therapeutic procedures. Route of administration can vary with therapeutic procedures or surgeries and can be determined by a skilled artisan. In yet another embodiment, compositions and methods of the invention can be used as an adjuvant therapy.

In some embodiments, the subject is a human, and in alternative embodiments the subject is a non-human mammal. Treatment dosages need to be titrated to optimize safety and efficacy. The amount of an autophagy activator depends on the stage of the disease, as well as the species.

In some embodiments, an autophagy activator can be administered to a subject in a pharmaceutical composition comprising an amount of an autophagy activator of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some embodiments an autophagy activator can be used in an amount of about 0.1 to 1000 µg/kg of body weight or about 1 to 100 µg/kg of body weight or about 10 to 50 µg/kg of body weight. In some embodiments, an autophagy activator can be administered at a concentration of about 0.001 mg/ml or 0.1 mg/ml or a higher concentration of 0.1 mg/ml. In alternative embodiments, a pharmaceutical composition comprises at least one autophagy activator at a concentration of about 0.01 µM to 300 µM, or about 0.1 µM to 150 µM, or about 1 µM to 50 µM, or about 1 µM to 25 µM.

The inventors have demonstrated herein that an autophagy activator reverses the vascular deformations and morphology in vivo of rps29−/− zebrafish embryos at a concentration of between 5-50 µg/mL, and that TFP restored the percentage of CD71+ cells in a erythroid cell population at between 5-20 µM in vitro. Accordingly, in some embodiments, an autophagy activator as disclosed herein can be administered to a subject according to the methods as disclosed herein in an effective dose to increase the levels of CD71+ cells in an erythroid cell population obtained from the subject by at least about 1%, at least about 2%, at least about 3%, at least about 5%, at least about 10%, at least about 15%, least about 20%, at least about 30%, at least about 40%, at least about 50%, or more than 50%, as compared to in the absence of an autophagy activator.

The inventors have demonstrated herein that the autophagy activator SMER28, at 1.5 µM decreased the levels of p21 in CD34+ cells present in DBA patient derived erythroid cell population in vitro. Accordingly, in another embodiment, an autophagy activator as disclosed herein can be administered to a subject according to the methods as disclosed herein in an effective dose to decrease the levels of p21 expression in CD34+ cells present in an erythroid cell population obtained from the subject by at least about 1%, at least about 2%, at least about 3%, at least about 5%, at least about 10%, at least about 15%, at least about 20%, at least about 30%, at least about 40%, at least about 50%, at least about 60%, at least about 70%, at least about 80%, at least about 90%, at least about 95%, at least about 98%, at least about 99%, or more than 99%, as compared to in the absence of an autophagy activator.

Generally, effective dosages and dosing schedules can be adjusted based on, for example, the outcome of the treatment such as whether the subject has reduced symptoms of anemia, and/or whether at least one of the symptoms associated with the ribosomal protein disorder, such as DBA is reduced. In accordance with the teachings provided herein, the effectiveness of the treatment can be monitored by obtaining a biological sample from a subject, e.g. a blood serum sample, and determining the level of biomarkers for DBA, such as percentage of CD71+ cells in a erythroid cell population and/or level of p21 in CD34+ cells, using methods well known in the art and the diagnostic methods as disclosed later herein.

In some embodiments, the daily dose administered to a subject in a form of a bolus composition comprising an autophagy activator can be given in a single dose, in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease. It is also within the skill of the art to start doses at levels lower than required to achieve the desired therapeutic effect and to gradually increase the dosage until the desired effect is achieved.

The pharmaceutical compositions comprising at least one autophagy activator as disclosed herein can be administered by parenteral, topical, intravenous, oral, subcutaneous, intraperitoneal, intranasal or intramuscular means for prophylactic and/or therapeutic treatment. Other routes of administration of an autophagy activator as disclosed herein are intramuscular (i.m.), intravenous (i.v.), subcutaneous (s.c.), or orally, although other routes can be equally effective. Intramuscular injection is most typically performed in the arm or leg muscles. In some methods, an autophagy activator as disclosed herein can be administered as a sustained release composition or device, such as a Medipad™ device.

In some embodiments, an autophagy activator as disclosed herein can optionally be administered in combination with other agents that are at least partly effective in treatment of ribosomal protein diseases and disorders, such as blood transfusions, bone marrow transplants and the like. In other embodiments, an autophagy activator of the invention can be administered prior to, concurrently, or after administration of another therapeutic that targets another disease or disorder, or a different symptom.

In various embodiments, an autophagy activator can be a pro-drug, where it is activated by a second agent. Accordingly, in such embodiments, administration of such the second agent which activates the pro-drug of the autophagy activator into its active form can be administered the same time, concurrent with, or prior to, or after the administration of the pharmaceutical composition comprising an autophagy activator as disclosed herein.

In some embodiments, an autophagy activator as disclosed herein is often administered as pharmaceutical compositions comprising an active therapeutic agent, i.e. an autophagy activator, and a variety of other pharmaceutically acceptable components. See Remington's Pharmaceutical Science (15th ed., Mack Publishing Company, Easton, Pa., 1980). The formulation of the compositions depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, non-therapeutic, non-immunogenic stabilizers and the like. However, some reagents suitable for administration to animals may not necessarily be used in compositions for human use.

For parenteral administration, an autophagy activator as disclosed herein can be administered as injectable dosages of a solution or suspension of the substance in a physiologically acceptable diluent with a pharmaceutical carrier which can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Other mode of administration includes systemic delivery. In some embodiments, at least one autophagy activator as disclosed herein can be injected systemically such as by intravenous injection, or by injection or application to the relevant site, such as direct application to the site when the site is exposed in surgery. In some embodiments, a pharmaceutical composition of the invention can be formulated in a tablet and used orally for systemic administration. In various embodiments, pharmaceutical compositions of the invention can further comprises non-active ingredients (i.e. ingredients that have no therapeutic values for treatment of diseases, disorders or symptoms), such as physiologically acceptable carriers.

In various embodiments, modification of an autophagy activator by addition of a polymer is specifically contemplated, for example, using a covalent attachment to a polymer. In other embodiments, an autophagy activator can be mixed with or encapsulated in a biocompatible polymer.

In another aspect, biodegradable or absorbable polymers can provide extended, often localized, release of an autophagy activator as disclosed herein. The potential benefits of an increased half-life or extended release for a therapeutic agent are clear. A potential benefit of localized release is the ability to achieve much higher localized dosages or concentrations, for greater lengths of time, relative to broader systemic administration, with the potential to avoid possible undesirable side effects that may occur with systemic administration.

Bioabsorbable polymeric matrix suitable for delivery of an autophagy activator as disclosed herein, or variants or fragments or derivatives thereof can be selected from a variety of synthetic bioabsorbable polymers, which are described extensively in the literature. Such synthetic bioabsorbable, biocompatible polymers, which may release proteins over several weeks or months can include, for example, poly-hydroxy acids (e.g. polylactides, polyglycolides and their copolymers), polyanhydrides, polyorthoesters, segmented block copolymers of polyethylene glycol and polybutylene terephtalate (POLYACTIVE™), tyrosine derivative polymers or poly(ester-amides). Suitable bioabsorbable polymers to be used in manufacturing of drug delivery materials and implants are discussed e.g. in U.S. Pat. Nos. 4,968,317, 5,618,563 (which are incorporated herein in their entirety by reference), among others, and in "Biomedical Polymers" edited by S. W. Shalaby, Carl Hanser Verlag, Munich, Vienna, New York, 1994 and in many references cited in the above publications. The particular bioabsorbable polymer that should be selected will depend upon the particular patient that is being treated.

The methods of the present invention also are useful for monitoring a course of treatment being administered to a subject. The methods can be used to monitor both therapeutic treatment on symptomatic subject and prophylactic treatment on asymptomatic subject.

A treatment administered to a subject is considered to be effective if the level of expression of p21 in CD34+ cells present in a biological sample obtained from the subject is decreased by at least about 20%, at least about 30%, at least about 40%, at least about 50%, at least about 60%, at least about 70%, at least about 80%, at least about 90%, at least about 95%, at least about 98%, about 99% or about 100% as compared to a reference level, or in the absence of the autophagy activator. In such embodiments, the reference level is the measurement of p21 in CD34+ cells present in a biological sample obtained from the subject at a previous time point, e.g., who has not been administered the autophagy activator. Based on the outcome of treatment, the dosage and frequency of administration using the methods and compositions as disclosed herein can be adjusted accordingly by one of skill in the art.

One can use any immunoassay to determine the level of p21 expression in CD34+ cells in a biological sample, such as ELISA or immunohistochemical methods which are commonly known in the art and are encompassed for use in the present invention.

Cell Differentiation

Differentiation is the process by which an unspecialized ("uncommitted") or less specialized cell acquires the features of a specialized cell (e.g., a terminally differentiated cell) such as, for example, a hematopoietic cell, cardiomyocyte, a nerve cell or a skeletal muscle cell. A differentiated or differentiation-induced cell is one that has taken on a more specialized ("committed") position within the lineage of a cell (e.g., reduced differentiation potential). The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell (i.e., increased developmental potential). As used herein, the lineage of a cell defines the heredity or fate of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

Cells that are differentiated using the compositions and methods described herein, can be differentiated into any cell type or lineage known to one of skill in the art. Such cells can be of a lineage selected from an ectodermal lineage, a mesodermal lineage, or an endodermal lineage. Exemplary ectodermal lineage cells include, but are not limited to, cells of the epidermis (skin cells, melanocytes), and cells of the neuronal lineage. Exemplary mesodermal lineage cells include, but are not limited to, cells of the circulatory system (cardiac cells and blood vessel cells), cells of the connective tissue, bone cells, dermal cells, myocytes (smooth and skeletal), certain cells of the urinary system, such as kidney cells, splenic cells, mesothelial cells (cells of the peritoneum, pleura, and pericardium), non-germ cells of the reproductive system, and hematopoietic lineage cells. Exemplary endodermal lineage cells include, but are not limited to, cells of the gastrointestinal system, cells of the respiratory tract, cells of the endocrine glands, cells of the auditory system, and certain cells of the urinary system, such as the bladder and parts of the urethra.

Accordingly, methods described herein include a method for programming or directing the differentiation of cells (e.g., stem cells) comprising contacting the cells desired to be differentiated with a nucleic acid encoding differentiation-inducing genes. The cells can be transfected a plurality of times until the desired differentiated phenotype is achieved, as measured by e.g., a gene expression array of cell-type specific markers, Western blotting, cell function assays etc. A selection compound may be added to the mixture, but is not required.

Typically, nucleic acid encoding differentiation-inducing genes transfected into the cells to promote their differentiation is cell-type specific. For example, to differentiate a cell to a neuronal cell phenotype, a synthetic, modified RNA encoding at least one neuronal differentiation factor, for example Ascl1, Brn2, Myt11, or a combination thereof is transfected into the cell. To promote differentiation to a myogenic phenotype, a nucleic acid encoding MyoD can be transfected into a cell. To differentiate a cell to a macrophage phenotype, a macrophage factor such as e.g., CEBP-alpha or PU.1 is transfected into the cell. In one embodiment, a nucleic acid that encodes Ngn3, Pdx1, MAFA, or any combination thereof can be used to differentiate cells to a pancreatic beta cell phenotype. A nucleic acid encoding PRDM16 can be applied to Myf5-expressing progenitors to induce differentiation into brown fat cells. Oligodendrocytes may be specified from neural precursors using a synthetic, modified RNA encoding Ascl1. It has been reported that hepatocyte differentiation requires the transcription factor HNF-4α. (Li et al., Genes Dev. 14:464, 2000). A nucleic acid can be applied to a cell, such as a stem cell or induced pluripotent stem cell generated using the methods described herein, that inhibit or suppress one or more component of the wnt/β-catenin pathway to become a cardiovascular progenitor cell. These examples are not meant to be limiting and essentially any cell-type specific factor or differentiation factor known in the art can be expressed in a cell using a nucleic acid encoding a differentiation-inducing gene as described herein.

In other embodiments, cells with higher or increased developmental potential, e.g., pluripotent cells, multipotent cells, etc., can be induced to differentiate by manipulating their external environment. For example, cells can be maintained under culture conditions that induce differentiation of the cells to a desired lineage. As but one example, in some embodiments, cells with higher or increased developmental potential, generated using the compositions and methods comprising a nucleic acid encoding a differentiation-inducing gene described herein, can be differentiated into islet-like cells for administration to a patient in need thereof, for example, a patient having or at risk for diabetes.

The success of a differentiation program can be monitored by any of a number of criteria, including characterization of morphological features, detection or quantitation of expressed cell markers and enzymatic activity, and determination of the functional properties of the desired end cell types in vitro or in vivo. The level of mRNA corresponding to a marker can be determined both by in situ and by in vitro formats. The isolated mRNA can be used in hybridization or amplification assays that include, but are not limited to, Southern or Northern analyses, polymerase chain reaction analyses and probe arrays. Protein markers can be measured e.g., by immunohistochemical techniques or the morphology of the cell can be monitored. Biochemical approaches, e.g., the ability of the differentiated cell to respond to a cell-type specific stimulus can also be monitored. An increase in the expression of a cell specific marker may be by about 5%, 10%, 25%, 50%, 75% or 100%, e.g. Seal-positive, cKit-positive, CD34-positive, and Flk2-negative. Other methods for assaying cell morphology and function are known in the art and are described in the Examples.

In some embodiments, the cells of the compositions and methods described herein are further cultured in the presence of cell specific growth factors, such as angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-1S, bone morphogenic protein receptor IA, bone morphogenic protein receptor IB, brain derived neurotrophic factor, ciliary neutrophic factor, ciliary neutrophic factor receptor-alpha, cytokine-induced neutrophil chemotactic factor 1, cytokine-induced neutrophil, chemotactic factor 2-alpha, cytokine-induced neutrophil chemotactic factor 2-beta, beta-endothelial cell growth factor, endothelia 1, epidermal growth factor, epithelial-derived neutrophil attractant, fibroblast growth factor 4, fibroblast growth factor 5, fibroblast growth factor 6 fibroblast growth factor 7, fibroblast growth factor 8, fibroblast growth factor b, fibroblast growth factor c, fibroblast growth factor 9, fibroblast growth factor 10, fibroblast growth factor acidic, fibroblast growth factor basic, glial cell line-derived neutrophil factor receptor-alpha-1, glial cell line-derived neutrophil factor receptor-alpha-2, growth related protein, growth related protein-alpha, growth related protein-beta, growth related protein-gamma, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-alpha, nerve growth factor, nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-alpha, platelet derived growth factor receptor-beta, pre-B cell growth stimulating factor, stem cell factor, stem cell factor receptor, transforming growth factor-alpha, transforming growth factor-beta, transforming growth factor-beta-1, transforming growth factor-beta-1-2, transforming growth factor-beta-2, transforming growth factor-beta-3, transforming growth factor-beta-5, latent transforming growth factor-beta-1, transforming growth factor-beta-binding protein I, transforming growth factor-beta-binding protein II, transforming growth factor-beta-binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. Such factors can also be injected or otherwise administered directly into an animal system for in vivo integration.

Screening Methods

The ability to safely and efficiently reprogram, differentiate, transdifferentiate cells using the differentiation-inducing agents and methods thereof described herein has high applicability for use in high-throughput screening technologies of disease model systems and assays for the characterization of candidate agents for identifying novel agents for use in the treatment of human disease. Such screening methods and platforms can be used, for example, to identify novel agents for treating a desired disorder; to identify novel agents involved in reprogramming and differentiation, and/or alteration/maintenance of developmental states; or to identify effects of a candidate agent on one or more parameters of a particular cell type or engineered tissue generated using the compositions and methods described herein. Characterization of candidate agents can include aspects such as compound development, identifying cell-specific toxicity and cell-specific survival, and assessments of compound safety, compound efficacy, and dose-response parameters. For example, an engineered myocardium tissue can be contacted with a test agent, and the effect, if any, of the test agent on a parameter, such as an electrophysiological parameter, associated with normal or abnormal myocardium function, such as contractibility, including frequency and force of contraction, can be determined, or e.g., whether the agent has a cardiotoxic effect.

The drug discovery process is time-consuming and costly, in part owing to the high rate of attrition of compounds in clinical trials. Thus, modifications and alternative platforms that could accelerate the advancement of promising drug candidates, or reduce the likelihood of failure, would be extremely valuable. High-throughput screening technologies refer to the platforms and assays used to rapidly test thousands of compounds. For example, reporter systems used in cell lines can be used to assess whether compounds activate particular signaling pathways of interest.

The method of using nucleic acid encoding differentiation-inducing genes for reprogramming, and differentiating described herein provide a reliable source of cells that can be generated and expanded in an efficient manner to quantities necessary for drug screening and toxicology studies. As has been described herein, cells can be differentiated to generate specific cell types (for example, blood cells), and induced pluripotent stem cells can be generated from patients with specific diseases, such as, for example, a patient with DBA, as demonstrated herein.

In such embodiments, human stem cells, such as iPSC cells, derived from patients can be exposed to appropriate differentiation factors using the methods described herein, and instructed to form the various cell types found in the human body, which could then be useful for assessing multiple cellular parameters and characteristics upon exposure to a candidate agent or compound. For example, the cells could be used to assess the effects of drug candidates on functional hematopoietic cell, or non-hematopoietic cell having a specific genetic mutation. Also, for example, such cells can be used to identify metabolic biomarkers in hematopoietic cells derived from human stem cells after toxin exposure. Such embodiments allow potentially toxic compounds to be eliminated at an early stage of the drug discovery process, allowing efforts to be directed to more promising candidates In other aspects, the methods described herein, can be used to screen for drugs that may correct an observed disease phenotype. In such aspects, cells can be expanded, differentiated into the desired cell type using methods described herein, and then used to screen for drugs that may correct the observed disease phenotype. A candidate agent or drug can be used to directly contact the surface of a reprogrammed, differentiated, transdifferentiated cell population, or engineered tissue by applying the candidate agent to a media surrounding the cell or engineered tissue. Alternatively, a candidate agent can be intracellular as a result of introduction of the candidate agent into a cell.

As used herein, "cellular parameters" refer to quantifiable components of cells or engineered tissues, particularly components that can be accurately measured, most desirably in a high-throughput system. A cellular parameter can be any measurable parameter related to a phenotype, function, or behavior of a cell or engineered tissue. Such cellular parameters include, changes in characteristics and markers of a cell or cell population, including but not limited to changes in viability, cell growth, expression of one or more or a combination of markers, such as cell surface determinants, such as receptors, proteins, including conformational or posttranslational modification thereof, lipids, carbohydrates, organic or inorganic molecules, nucleic acids, e.g. mRNA, DNA, global gene expression patterns, etc. Such cellular parameters can be measured using any of a variety of assays known to one of skill in the art. For example, viability and cell growth can be measured by assays such as Trypan blue exclusion, CFSE dilution, and $^3H$ incorporation. Expression of protein or polypeptide markers can be measured, for example, using flow cytometric assays, Western blot techniques, or microscopy methods. Gene expression profiles can be assayed, for example, using microarray methodologies and quantitative or semi-quantitiative real-time PCR assays. A cellular parameter can also refer to a functional parameter, such as a metabolic parameter (e.g., expression or secretion of a hormone, such as insulin or glucagon, or an enzyme, such as carboxypeptidase), an electrophysiological parameter (e.g., contractibility, such as frequency and force of mechanical contraction of a muscle cell; action potentials; conduction, such as conduction velocity), or an immunomodulatory parameter (e.g., expression or secretion of a cytokine or chemokine, such as an interferon, or an interleukin; expression or secretion of an antibody; expression or secretion of a cytotoxin, such as perform, a granzyme, and granulysin; and phagocytosis).

The "candidate agent" used in the screening methods described herein can be selected from a group of a chemical, small molecule, chemical entity, nucleic acid sequences, an action; nucleic acid analogues or protein or polypeptide or analogue of fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof. A candidate agent also includes any chemical, entity or moiety, including without limitation synthetic and naturally-occurring non-proteinaceous entities. In certain embodiments, the candidate agent is a small molecule having a chemical moiety. Such chemical moieties can include, for example, unsubstituted or substituted alkyl, aromatic, or heterocyclyl moieties and typically include at least an amine, carbonyl, hydroxyl or carboxyl group, frequently at least two of the functional chemical groups, including macrolides, leptomycins and related natural products or analogues thereof. Candidate agents can be known to have a desired activity and/or property, or can be selected from a library of diverse compounds.

Also included as candidate agents are pharmacologically active drugs, genetically active molecules, etc. Such candidate agents of interest include, for example, chemotherapeutic agents, hormones or hormone antagonists, growth factors or recombinant growth factors and fragments and variants thereof. Exemplary of pharmaceutical agents suitable for use with the screening methods described herein are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all of which are incorporated herein by reference in their entireties. Also included are toxins, and biological and chemical warfare agents, for example see Somani, S. M. (Ed.), "Chemical Warfare Agents," Academic Press, New York, 1992), the contents of which is herein incorporated in its entirety by reference.

Candidate agents, such as chemical compounds, can be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Synthetic chemistry transformations and protecting group methodologies (protection and deprotection) useful in synthesizing the candidate compounds for use in the screening methods described herein are known in the art and include, for example, those such as described in R. Larock (1989) Comprehensive Organic Transformations, VCH Publishers; T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof, the contents of each of which are herein incorporated in their entireties by reference.

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233, the contents of each of which are herein incorporated in their entireties by reference.

Libraries of candidate agents can be presented in solution (e.g., Houghten (1992), Biotechniques 13:412-421), or on beads (Lam (1991), Nature 354:82-84), chips (Fodor (1993) Nature 364:555-556), bacteria (Ladner, U.S. Pat. No. 5,223, 409), spores (Ladner U.S. Pat. No. 5,223,409), plasmids (Cull et al. (1992) Proc Natl Acad Sci USA 89:1865-1869)

or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.), the contents of each of which are herein incorporated in their entireties by reference.

Kits

Another aspect of the present invention relates to a kit comprising one or more autophagy modulator as disclosed herein, and instructions for carrying out a method as disclosed herein.

In some embodiments, a kit can optionally additionally comprise reagents or agents for measuring the level of p21 expression in a biological sample from the subject, such as, for example, a blood sample, for example to identify the efficacy of treatment with the autophagy modulator as disclosed herein. Such agents are well known in the art, and include without limitation, labeled antibodies that specifically bind to p21 protein and/or mRNA and the like. In some embodiments, the labeled antibodies are fluorescently labeled, or labeled with magnetic beads and the like. In some embodiments, a kit as disclosed herein can further comprise at least one or more reagents for profiling and annotating a biological sample from the subject in high throughput assay.

In some embodiments, the kit can further comprise instructions for administering a composition comprising a autophagy modulator to a subject in need thereof, e.g., with a ribosomal protein disease or disorder, e.g., DBA and instructions for doses and the like.

In addition to the above mentioned component(s), the kit can also include informational material. The informational material can be descriptive, instructional, marketing or other material that relates to the methods described herein and/or the use of the components for the assays, methods and systems described herein.

In some embodiments, the methods and kits comprising a autophagy modulator as disclosed herein can be performed by a service provider, for example, where an investigator or physician can send the biological sample to a diagnostic laboratory service provider to measure the level of p21 expression in CD34+ cells in a erythroid cell population present in the biological subject from the subject. In such an embodiment, after performing the such measurements, the service provider can provide the investigator or physician a report of the efficacy of the autophagy modulator and/or report if the subject is a suitable or amenable to be treated with a autophagy modulator according to the methods and composition as disclosed herein.

In alternative embodiments, a service provider can provide the investigator with the raw data of the levels of p21 expression in CD34+ cells in a erythroid cell population present in the biological subject from the subject and leave the analysis to be performed by the investigator or physician. In some embodiments, the report is communicated or sent to the investigator via electronic means, e.g., uploaded on a secure web-site, or sent via e-mail or other electronic communication means. In some embodiments, the investigator can send the samples to the service provider via any means, e.g., via mail, express mail, etc., or alternatively, the service provider can provide a service to collect the samples from the investigator and transport them to the diagnostic laboratories of the service provider. In some embodiments, the investigator can deposit the samples to be analyzed at the location of the service provider diagnostic laboratories. In alternative embodiments, the service provider provides a stop-by service, where the service provider send personnel to the laboratories of the investigator and also provides the kits, apparatus, and reagents for performing the assays to measure the levels of p21 expression in CD34+ cells in a erythroid cell population present in the biological subject from the subject as disclosed herein in the investigators laboratories, and analyses the result and provides a report to the investigator for each subject, and leaves the physician to make appropriate recommendations of treatment, and dose to administer the subject with a composition comprising a autophage modulator according to the methods as disclosed herein.

Other than in the operating examples, or where otherwise indicated, all numbers expressing quantities of ingredients or reaction conditions used herein should be understood as modified in all instances by the term "about." The term "about" when used in connection with percentages can mean ±1%. The present invention is further explained in detail by the following, including the Examples, but the scope of the invention should not be limited thereto.

This invention is further illustrated by the examples which should not be construed as limiting. The contents of all references cited throughout this application, as well as the figures and tables are incorporated herein by reference. All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of the various aspects described herein can be illustrated by the following numbered paragraphs.

1. A method of treating a subject with a ribosomal disorder or ribosomopathy, comprising administering an effective amount of a compound having Structure I or a derivative, analogue or pharmaceutically acceptable form thereof.

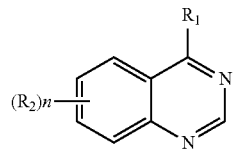

Structure I wherein $R_1$ can be hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_n$; —$NO_2$; —$N(R_A)_2$; —$NHC(O)R_A$; —$C(R_A)_3$,

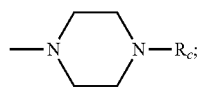

—CH₂CH₂R_D; wherein each occurrence of R_A, R_c, and R_D is independently a hydrogen, a protecting group, an aliphatic moiety (e.g., ethyl, methyl or propyl), a heteroaliphatic moiety, an unsaturated group (e.g., Allyl), an acyl moiety, 4-(1,3-Benzodioxol-5-ylmethyl), Phenol, 4-Chlorophenyl, 4-Phenoxypheny, 4-(Cyclopentyloxy)phenyl, 4-(Benzyloxy)phenyl, Ethyl (4-phenoxy)acetate; an aryl moiety (e.g., benzyl); a heteroaryl moiety; alkoxy; aryloxy; alkylthio; arylthio; amino, alkylamino, dialkylamino, heteroaryloxy; or heteroarylthio moiety;

R₂ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR_B; —C(=O)R_B; —CO₂R_B; —CN; —SCN; —SR_B; —SOR_B; —SO₂R_B; —NO₂; —N(R_B)₂; —NHC(O)R_B; or —C(R_B)₃; wherein each occurrence of R_B is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

n is an integer between 0 and 4, inclusive;

and pharmaceutically acceptable forms thereof.

2. The method of numbered paragraph 1, wherein R₁ is —OR_A, —SR_A, NHR_A

or —CH₂CH₂R_D

3. The method of numbered paragraph 1 or 2, wherein R_A is a C2-C6 alkenyl moiety, a vinyl moiety, or an allyl moiety.

4. The method of any one of the above numbered paragraphs, wherein R₂ is a halogen, —OR_B or —OH.

5. The method of any one of the above numbered paragraphs, wherein R₁ is —OR_A, R_A is an allyl moiety and R₂ is a halogen.

6. The method of any one of the above numbered paragraphs, wherein n is 1, 2 or 3.

7. The method of any one of the above numbered paragraphs, wherein the compound has the following structure:

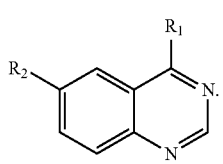

Structure II

8. The method of any one of the above numbered paragraphs, wherein the compound is 6-Bromo-N-2-propenyl-4-quinazolinam (SMER28) having Structure III, or a derivative or analogue thereof

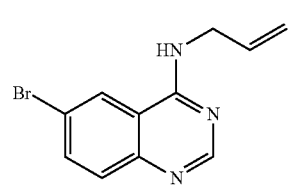

Structure III

9. The method of any one of the above numbered paragraphs, wherein the ribosomal disorder or ribosomopathy is selected from a group consisting of: Diamond Blackfan Anemia (DBA), inherited erythroblastopenia, 5q-syndrome, Schwachman-Diamond syndrome, Dyskeratosis congenita, Cartilage hair hypoplasia, and Treacher Collins syndrome, Hoyeraal-Hreidarsson syndrome, and Prader-Willi syndrome.

10. The method of any one of the above numbered paragraphs, wherein the ribosomal disorder or ribosomopathy is Diamond Blackfan Anemia (DBA) or inherited erythroblastopenia.

11. The method of any one of the above numbered paragraphs, wherein the subject has DBA1, DBA2, DBA3, DBA4, DBA5, DBA6, DBA7, or DBA8.

12. The method of any one of the above numbered paragraphs, wherein the subject has at least one mutation in ribosomal protein selected from the group consisting of: RPS7, RPS10, RPS19, RPS24, PRS26, RPS17, PRS27L RPS29. RPL35A, RPL5 and RPL11.

13. The method of any one of the above numbered paragraphs, wherein the subject has a mutation in ribosomal protein 19 (RPS19).

14. The method of any one of the above numbered paragraphs, wherein the subject is administered another therapeutic agent to treat the ribosomal protein defect.

15. The method of any one of the above numbered paragraphs, wherein the subject is administered another therapeutic agent to treat the ribosomal protein defect, selected from the group consisting of: corticosteroids and blood transfusions.

16. The method of any one of the above numbered paragraphs, wherein the compound increases erythroid differentiation of a hematopoietic progenitor cell in the subject.

17. The method of any one of the above numbered paragraphs, wherein the compound increases differentiation of a CD71⁺GlyA⁺erythroid cell or population thereof in the subject.

18. The method of any one of the above numbered paragraphs, wherein the compound increases the levels of hemoglobin in the subject.

19. The method of any one of the above numbered paragraphs, wherein the compound increases the levels of red blood cells in the subject.

20. The method of any one of the above numbered paragraphs, wherein the compound induces autophagic flux in a erythroid cell or population thereof in the subject.

21. The method of any one of the above numbered paragraphs, wherein the compound increases erythropoiesis in vivo or in vitro.

22. The method of any one of the above numbered paragraphs wherein the compound decreases p62 levels and increases the levels of lipidated LC3-II.
23. A method for treating DBA, the method comprising; administering to a subject in need thereof a therapeutically effective amount of 6-Bromo-N-2-propenyl-4-quinazolinam (SMER28) having Structure III or a derivative or analogue thereof.
24. The method of numbered paragraph 23, wherein the patient has a mutation in the ribosomal protein RPS19.
25. A method for increasing the rate of red blood cell (RBC) differentiation, the method comprising: contacting a erythroblast or a population thereof at stage I-III of differentiation with SMER28.
26. The methods of numbered paragraph 25, wherein the erythroblast is derived from an embryonic stem cell or induced pluripotent stem cell in vitro.
27. The method of numbered paragraph 25, wherein the erythroblast is isolated from a patient.
28. A method for inducing Red Blood Cells (RBC) differentiation, the method comprising: contacting a hemtopoietic progenitor cell (HPC) or population thereof with nucleic acid encoding the reprogramming factors HOXA9, ERG, RORA, SOX4, and MYB for at least two weeks, thereby inducing a differentiated RBC.
29. The method of numbered paragraph 28, wherein the nucleic acid is expressed by a lentivirus.
30. The method of numbered paragraph 29, wherein the lentivirus is inducible.
31. The method of numbered paragraph 28, further comprising erythroid maturation.
32. The method of numbered paragraph 28, wherein the HPC or population thereof is/are $CD34^+$ $CD45^+$.
33. The method of numbered paragraph 28, wherein the HPC or population thereof is derived from a inducible pluripotent stem cell (iPS) or a pluripotent stem cell.
34. The method of numbered paragraph 28, wherein the HPC or population thereof is isolated from a patient.
35. The method of numbered paragraph 33, wherein the iPS is derived from a somatic fibroblast.
36. The method of numbered paragraph 35, wherein the somatic fibroblast cell is a mammalian cell.
37. The method of numbered paragraph 35, wherein the somatic fibroblast cell is a human cell.
38. The method of numbered paragraph 35, wherein the somatic fibroblast cell is a human cell and isolated from a subject with a ribosomal disorder.
39. The method of numbered paragraph 35, wherein the somatic fibroblast cell is a human cell and isolated from a subject with DBA.
40. The method of numbered paragraph 35, wherein the somatic fibroblast cell is a human cell and isolated from a subject with a mutation in the ribosomal protein RSP19.
41. The method of numbered paragraph 35, wherein the somatic fibroblast cell is differentiated to a iPS in vitro, ex vivo, or in vivo.
42. The method of numbered paragraph 32, wherein the iPS or pluripotent stem cell is differentiated to a HPS in vitro, ex vivo, or in vivo.
43. The method of numbered paragraph 28, further comprising engraftment of the differentiated RBC ex vivo or in vivo.
44. The method of numbered paragraph 28, wherein the differentiated RBC is $CD71^+GlyA^+$.
45. The method of numbered paragraph 28, wherein the differentiated RBC is enucleated.
46. An ex vivo method for screening agents to promote hematopoietic cell differentiation comprising the steps of: exposing a population of cells of paragraphs 28 to 45 to a candidate agent ex vivo; and comparing hematopoietic cell differentiation rate of the population of cells exposed to the candidate agent to a population of cells that has not been exposed to the candidate agent, wherein if the hematopoietic cell differentiation rate is increased in the population of cells exposed to the candidate agent compared to the population of cells that has not been exposed to the candidate agent, the agent is indicated as an agent that expands hematopoietic stem cells.
47. The method of numbered paragraph 46, wherein the hematopoietic cell is an erythroid.
48. The method of numbered paragraph 46, wherein the hematopoietic cell is an erythroblast.
49. The method of numbered paragraph 46, wherein the hematopoietic cell is a non-enucleated red blood cell.
50. The method of numbered paragraph 46, wherein the hematopoietic cell is a enucleated red blood cell.
51. The method of numbered paragraph 46, wherein the hematopoietic stem activity is self-renewal.
52. A method of treating a subject with a ribosomal disorder or ribosomopathy, comprising administering an effective amount of a autophagy modulator to the subject to decrease p21 and apoptosis in at least one of CD34+ cells, erythroid cells or erythroid differentiated cells in the subject.
53. The method of numbered paragraph 52, wherein the autophagy is activated.
54. The method of numbered paragraph 52 or 53, wherein the autophagy modulator is a compound having Structure I or a derivative, analogue or pharmaceutically acceptable form thereof.
55. The use of a compound having Structure I or a derivative, analogue or pharmaceutically acceptable form thereof in an effective amount to treat a subject with a ribosomal disorder or ribosomopath.
56. The use as in numbered paragraph 55, wherein $R_1$ is —$OR_A$, —$SR_A$ or —$NHR_A$.
57. The use as in numbered paragraph 55 or 56, wherein $R_A$ is a C2-C6 alkenyl moiety, a vinyl moiety, or an allyl moiety.
58. The use as in any of any one of numbered paragraphs 55-57, wherein $R_2$ is a halogen, —$OR_B$ or —OH.
59. The use as in any one of numbered paragraphs 55-58, wherein $R_1$ is —$OR_A$, $R_A$ is an allyl moiety and $R_2$ is a halogen.
60. The use as in any one of numbered paragraphs 55-59, wherein n is 1, 2 or 3.
61. The use as in any one of numbered paragraphs 55-60, wherein the compound has Structure II.
62. The use as in any one of numbered paragraphs 55-61, wherein the compound is 6-Bromo-N-2-propenyl-4-quinazolinam (SMER28).
63. The use as in any one of numbered paragraphs 55-62, wherein the ribosomal disorder or ribosomopathy is selected from a group consisting of: Diamond Blackfan Anemia (DBA), inherited erythroblastopenia, 5q-syndrome, Schwachman-Diamond syndrome, Dyskeratosis congenita, Cartilage hair hypoplasia, and Treacher Collins syndrome, Hoyeraal-Hreidarsson syndrome, and Prader-Willi syndrome.

64. The use as in any one of numbered paragraphs 55-63, wherein the ribosomal disorder or ribosomopathy is Diamond Blackfan Anemia (DBA) or inherited erythroblastopenia.

65. The use as in any one of numbered paragraphs 55-64, wherein the subject has DBA1, DBA2, DBA3, DBA4, DBA5, DBA6, DBA7, or DBA8.

66. The use as in any one of numbered paragraphs 55-65, wherein the subject has at least one mutation in ribosomal protein selected from the group consisting of: RPS7, RPS10, RPS19, RPS24, PRS26, RPS17, PRS27L RPS29. RPL35A, RPL5 and RPL11.

67. The use as in any one of paragraphs 55-66, wherein the subject has a mutation in ribosomal protein 19 (RPS19).

68. The use as in any one of numbered paragraphs 55-67, wherein the subject is administered another therapeutic agent to treat the ribosomal protein defect.

69. The use as in any one of numbered paragraphs 55-68, wherein the subject is administered another therapeutic agent to treat the ribosomal protein defect, selected from the group consisting of: corticosteroids and blood transfusions.

70. The use as in any one of numbered paragraphs 55-69, wherein the compound increases erythroid differentiation of a hematopoietic progenitor cell in the subject.

71. The use as in any one of numbered paragraphs 55-70, wherein the compound increases differentiation of a $CD71^+GlyA^+$ erythroid cell or population thereof in the subject.

72. The use as in any one of numbered paragraphs 55-71, wherein the compound increases the levels of hemoglobin in the subject.

73. The use as in any one of numbered paragraphs 55-72, wherein the compound increases the levels of red blood cells in the subject.

74. The use as in any one of numbered paragraphs 55-73, wherein the compound induces autophagic flux in a erythroid cell or population thereof in the subject.

75. The use as in any one of numbered paragraphs 55-74, wherein the compound increases erythropoiesis in vivo or in vitro.

76. The use as in any one of numbered paragraphs 55-75, wherein the compound decreases p62 levels and increases the levels of lipidated LC3-II.

77. The use of 6-Bromo-N-2-propenyl-4-quinazolinam (SMER28, Structure III) or a derivative or analogue of a SMER28 in a therapeutically effective amount to treat a patient that has DBA.

78. The use as in numbered paragraph 77, wherein the patient has a mutation in the ribosomal protein RPS19.

79. The use of an autophagy modulator in an effective amount to decrease p21 and apoptosis in at least one of CD34+ cells, erythroid cells or erythroid differentiated cells, in a subject with a ribosomal disorder or ribosomopathy.

80. The use as in numbered paragraph 79, wherein the autophagy is activated.

81. The use as in numbered paragraph 79 or 80, wherein the autophagy modulator is a derivative or analogue of a compound having Structure I.

82. A method for treating anemia, the method comprising: administering to a subject having and/or at risk of having anemia the compound set forth in numbered paragraph 1 and all numbered paragraphs therein.

83. The method of numbered paragraph 82, wherein the subject has treatment-related anemia due to treatment for another disorder such as cancer or dysplasia which include myelosuppression, chemotherapy, immunosuppression, or radiation therapy.

84. The use of the compound set forth in numbered paragraph 1 and all dependent numbered paragraphs therein for treating a subject having and/or at risk of having anemia.

85. The use as in numbered paragraph 84, wherein the subject has treatment-related anemia due to treatment for another disorder such as cancer or dysplasia which include myelosuppression, chemotherapy, immunosuppression, or radiation therapy.

EXAMPLES

Although any known methods, devices, and materials may be used in the practice or testing of the invention, the methods, devices, and materials in this regard are described herein.

SUMMARY

The present invention relates in part to the use of induced pluripotent stem cells (iPSCs) for drug discoveryiPSC-derived hematopoietic cells can be respecified with five transcription factors into expandable $CD34^+$ progenitors (CD34-5F) that undergo robust erythroid differentiation in vitro and after transplantation in immunodeficient mice. This platform was applied to discover drugs that promote erythroid development using Diamond-Blackfan anemia (DBA) as a genetically tractable disease model. Herein is shown that CD34-5F progenitors derived from DBA iPSCs recapitulate defects in erythroid differentiation which were rescued by gene complementation. In unbiased chemical screens, the compound SMER28 enhanced erythropoiesis in a range of in vitro and in vivo models. The induction of erythropoiesis by SMER28 involved lipidation of autophagic marker LC3, and was dependent on autophagy factor Atg5. These findings report the first unbiased drug screen with iPSCs for hematological disease, and identify a therapeutic for DBA, which implicates Atg5/LC3 in early erythroid development.

INTRODUCTION

The discovery of induced pluripotency has opened new avenues to regenerative medicine, including transplantation of autologous replacement tissues, disease modeling to gain new insights into pathophysiology, and drug screening against disease-relevant human cells. However, prior to the herein description there have been only limited demonstrations of induced pluripotent stem cell (iPSC)-based disease models yielding new drug candidates (Avior et al., 2016; Engle and Vincent, 2014; Stemeckert et al., 2014). Owing to the complexity of disease mechanisms and the paucity of robust protocols for deriving disease-relevant cells, an affected cell type or tissue is challenging to generate at the scale and purity needed for drug screening (Grskovic et al., 2011; Heilker et al., 2014). Directed differentiation protocols typically generate mature non-dividing cells, and do not capture somatic stem cells that normally sustain tissue homeostasis (Doulatov and Daley, 2013; Sterneckert et al., 2014). A strategy to overcome this problem is to expand the somatic stem or progenitor cell state as an abundant precursor of mature cells to enable chemical screens.

The blood system is a classical developmental hierarchy in which hematopoietic stem and progenitor cells (HPCs)

continuously replenish a pool of short-lived mature cells. HPCs differentiated directly from iPSCs are largely lineage restricted, have limited proliferative potential, and fail to engraft in vivo. While a large number of iPSC models have been established from patients with hematological diseases, inability to derive multipotential HPCs has hampered the utility of these models to interrogate disease mechanisms (Vo and Daley, 2015). Thus, the blood system is ideally suited to developing modeling approaches that induce or expand intermediate progenitors. It has been previously reported that five transcription factors (5F) can convert iPSC-derived HPCs into reversibly immortalized multilineage progenitors (Doulatov et al., 2013). Doxycycline-regulated conditional induction of 5F expands and maintains an immature $CD34^+$ $CD38^-$ self-renewing state (CD34-5F) while removing doxycycline (Dox) initiates differentiation. CD34-5F cells give rise to short-term engraftment after transplantation in immunodeficient mice, with erythroid progenitors undergoing maturation and hemoglobin switching in vivo. This approach generates large numbers of engraftable patient-specific cells for modeling hematological disease.

Anemia is the most common blood condition worldwide. Women and elderly are particularly at risk, with the prevalence in the elderly population exceeding 10%. Severe anemia associated with chemotherapy, chronic kidney disease, or underlying genetic conditions is often treated with transfusions, erythropoietin (Epo), or glucocorticoids such as dexamethasone (Dex), which stimulate the proliferation of erythroid progenitors. These agents are associated with potentially severe side effects, and many anemias fail to respond. Thus, there is considerable need for novel therapeutics. Diamond-Blackfan anemia (DBA), a severe macrocytic anemia which usually presents in the first year of life (Narla and Ebert, 2010), is associated with mutations in ribosomal protein genes, most commonly RPS19 (Draptchinskaia et al., 1999). Loss of a single allele of RPS19 perturbs the normal stoichiometry of ribosomal subunits, which leads to ribosomal stress and apoptosis of erythroid progenitors (Choesmel et al., 2007; Dutt et al., 2011). Since DBA affects erythroid differentiation, it is an attractive model to develop therapeutics to enhance inefficient erythropoiesis. Mouse models may not recapitulate the relevant aspects of human disease, as in the case of DBA where deletion of a single copy of Rps19 in mice results in only a mild anemia (Matsson et al., 2004). Knockdown of RPS19 by shRNAs in human $CD34^+$ progenitors is often used; however, it is difficult to achieve precise haploinsufficient protein dosage. DBA iPSCs have been described and recapitulate aspects of the disease (Garcon et al., 2013), but the utility of this model for drug discovery has not been exploited.

Herein is described the first unbiased chemical screen for hematological disease using patient iPSCs identifying SMER28 as a candidate therapeutic for DBA Results Hematopoietic Progenitor Differentiation from iPSCs To establish a model of DBA, fibroblasts were reprogrammed using episomal and Sendai methods from patients with RPS19 and RPL5 nonsense mutations. We established multiple independent lines of normal karyotype (Table 1) and confirmed the heterozygous nonsense mutation in iPSCs by Sanger sequencing (FIG. 1A and FIG. 2A). Patient fibroblasts from patient T15 showed the expected decrease in RPS19 protein levels, however RPS19 was not decreased in patient iPSCs (FIG. 1B and FIG. 2B), suggesting that the expression from the remaining copy is sufficient to maintain normal protein levels in iPSCs. However, RPS19 protein was decreased in erythroid cells differentiated from patient iPSC (FIG. 1C) showing a dosage in disease-affected blood cells.

TABLE 1

| Affected Gene | Sample | Mutation | Source | Method | Reprogrammed IPS Lines | Karyotyping | IPS lines used | % $CD34^+CD45^+$ |
|---|---|---|---|---|---|---|---|---|
| RPS19 | T15 | nonsense C280T | NIH | Episomal | 6 lines | ✓ | T15-2, T15-7 | 10-20% |
|  |  |  |  | Sendai | 3 lines | ✓ | T15-18, T15-14 | 10-20% |
| RPL5 | T5 | nonsense C48A | BCH | Episomal | 2 lines | ✓ | not used | <1% |
|  |  |  |  | Sendai | 3 lines | ✓ | T5-2, T5-3 | 5-20% |
| RPL5 parent | 278/9 | — | BCH | Sendai | 3 lines | ✓ | 278 father, 279 mother | 10-20% |
| Normal | $CD34^+$ cells | — | BCH | Episomal | 2 lines | ✓ | CD34IPS-10, -2 | 10-20% |
| Normal | $CD45^+$ cells | — | BCH | Episomal | 1 line | ✓ | CD45IPS-1 | 5-20% |
| Normal | MSCs | — | BCH | Lentiviral | 1 line | ✓ | MSC-IPS1 | 10-20% |

Figure 1E:
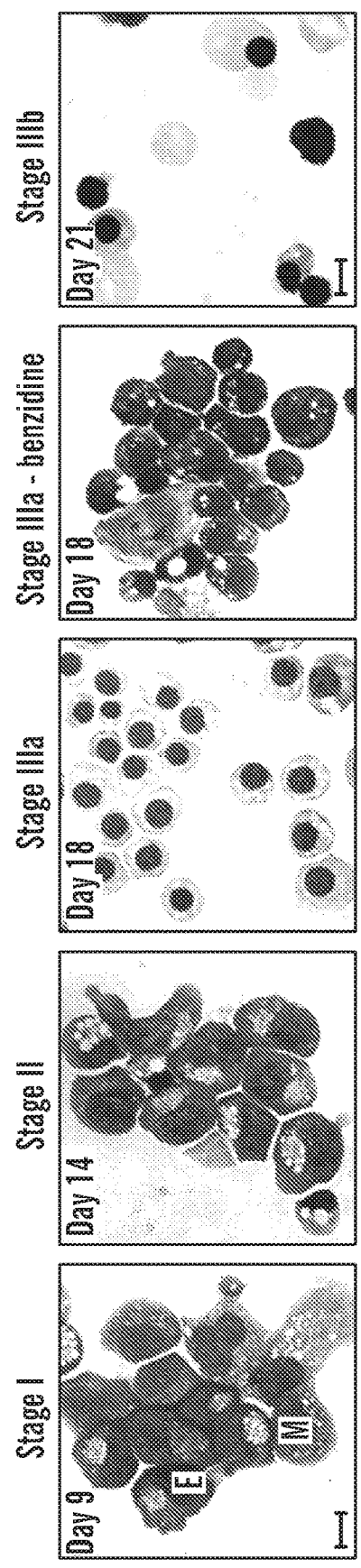
Figure 3A:
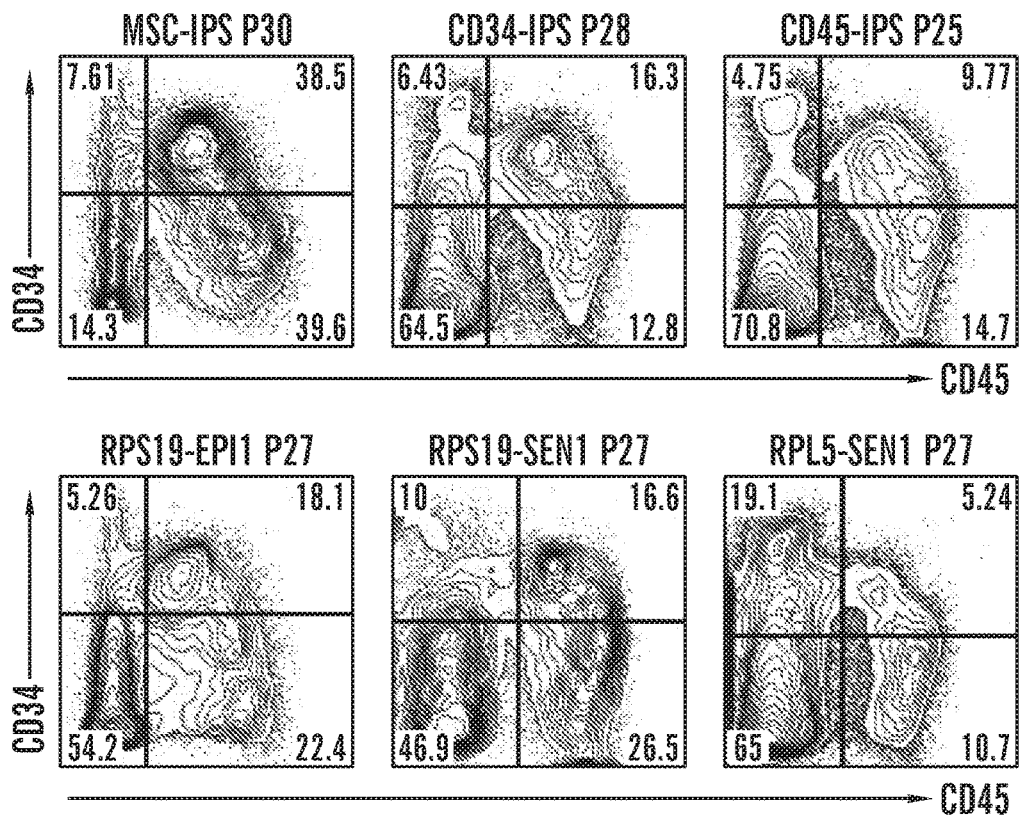
FIGS. 3A and 3B show population analysis of differentiated iPSC.
Figure 3B:
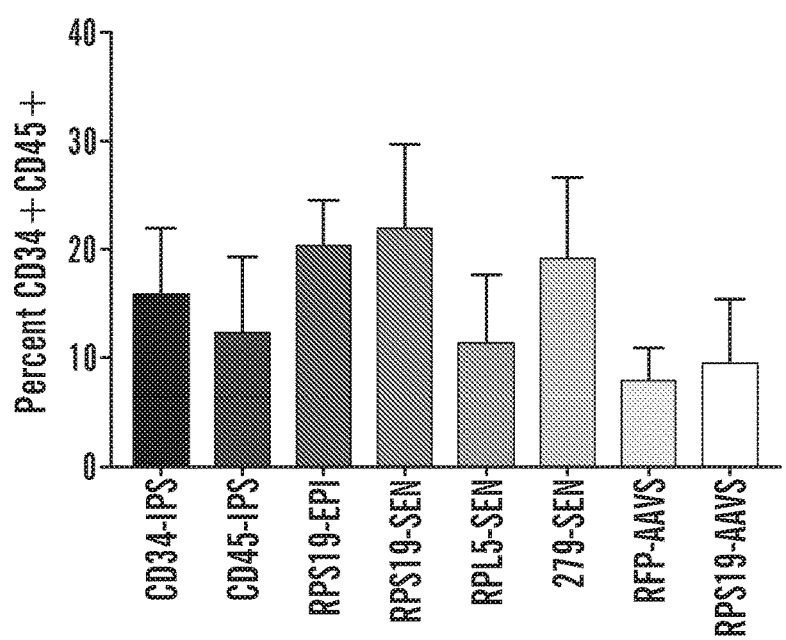
Figure 4A:
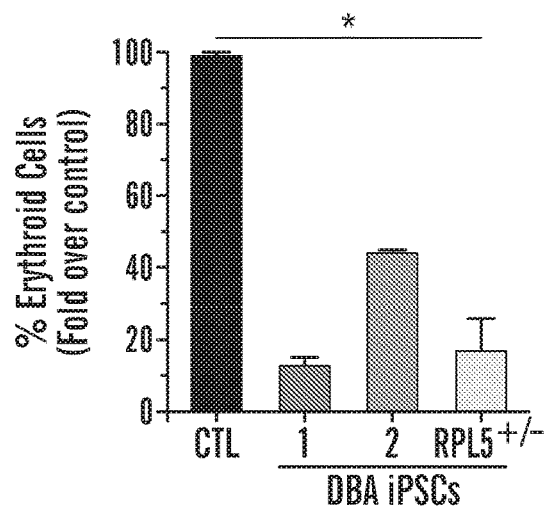
FIGS. 4A-4C show the erythoid population in differentiated iPSC.
Figure 4B:
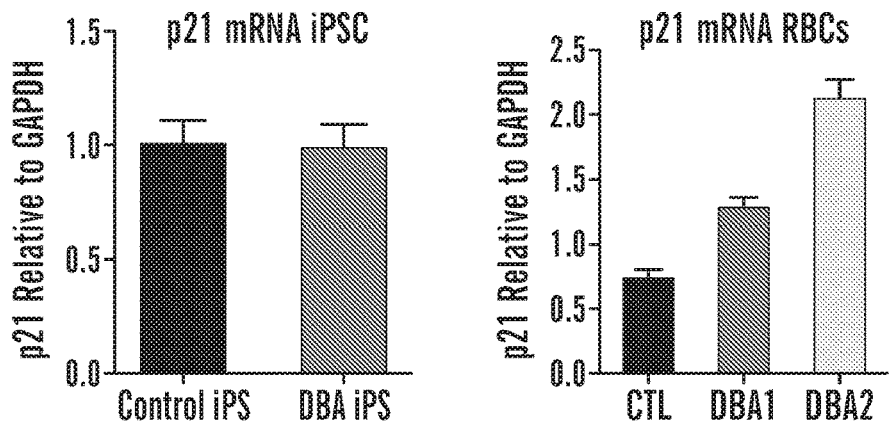
Figure 4C:
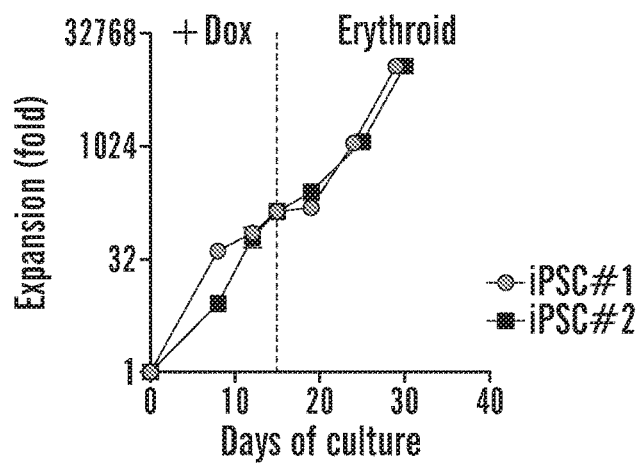

DBA iPSCs were differentiated as embryoid bodies (EB) into day 9 $CD34^+$ $CD43^+$ HPCs (d9-HPCs), or more definitive day 14 $CD34^+$ $CD45^+$ HPCs. DBA and normal iPSCs gave rise to comparable numbers of HPCs, although the frequency varied between lines (FIG. 3). DBA d9-HPCs gave rise to fewer $CD71^+$ Glycophorin A $(GlyA)^+$erythroid cells compared to normal iPSCs (FIG. 4A). In addition, expression of p21 was higher in DBA erythroid cells (FIG. 4B) as noted in other models of DBA. However, it was not possible to carry out further characterization due to the limited proliferative capacity of HPCs differentiated directly from iPSCs. To overcome this limitation, a previously reported transcription factor-based respecification system was adopted to expand iPSC-derived HPCs (Doulatov et al., 2013). HPCs isolated on day 14 of EB differentiation were transduced with the 5F lentiviruses (CD34-5F cells). After 2 weeks of expansion with Dox, progenitors were differentiated using an erythroid maturation protocol that enables large-scale differentiation into mature red blood cells (RBCs) (Lee et al., 2015) (FIG. 1D). The protocol consists of an expansion phase when differentiation is initiated by removal of Dox, followed by maturation stages I-III. CD34-5F progenitors matured in this fashion transitioned through the same morphologic stages as cord blood (CB) $CD34^+$ progenitors (FIG. 1E). CD34-5F cells retain some embryonic features in vitro, such as expression of embryonic and fetal globins, and low efficiency of enucleation, but undergo globin switching and enucleation upon engraftment in vivo (Doulatov et al., 2013). Total expansion was >1×10⁴-fold for control iPSCs, corresponding to >10⁹ RBCs from an average EB batch (FIG. 4C). Thus, this progenitor system represents a powerful platform for molecular interrogation of disease mechanisms and drug discovery.

DBA patients contributed only 13 f 6.8% erythroid engraftment (FIG. 6C, Table 2). Thus, CD34-5F cells derived from DBA iPSCs display reduced erythroid potential in vitro and in vivo, and represent a robust and scalable resource for drug screening.

TABLE 2

| DBA IPSC | CD45+CD33+ | CD45$^{neg}$ GLYA+ | Ter119+ | Ter119$^{neg}$ Myeloid | Ter119$^{neg}$ Erythroid | Total human | Erythroid % |
|---|---|---|---|---|---|---|---|
| m1 | 0.19 | 0.02 | 45.4 | 0.35 | 0.03 | 0.38 | 9.09 |
| m2 | 0.12 | 0.00 | 59.5 | 0.32 | 0.01 | 0.33 | 2.38 |
| m3 | 0.09 | 0.00 | 69.6 | 0.31 | 0.00 | 0.32 | 1.48 |
| m4 | 0.09 | 0.01 | 75.3 | 0.36 | 0.02 | 0.39 | 5.75 |
| m5 | 0.46 | 0.04 | 49.4 | 0.97 | 0.08 | 1.04 | 7.20 |
| m6 | 0.13 | 0.01 | 55.1 | 0.33 | 0.03 | 0.36 | 7.41 |
| m7 | 0.09 | 0.00 | 63.4 | 0.24 | 0.01 | 0.25 | 3.78 |
| m8 | 0.05 | 0.10 | 66.8 | 0.15 | 0.30 | 0.45 | 66.44 |
| m9 | 0.06 | 0.01 | 55.7 | 0.17 | 0.03 | 0.20 | 15.73 |

| Control-IPSC | CD45+CD33+ | CD45$^{neg}$ GLYA+ | Ter119+ | Ter119$^{neg}$ Myeloid | Ter119$^{neg}$ Erythroid | Total human | Erythroid % |
|---|---|---|---|---|---|---|---|
| m1 | 0.21 | 0.52 | 55.2 | 0.47 | 1.16 | 1.63 | 71.23 |
| m2 | 0.32 | 18.30 | 45.5 | 0.61 | 33.58 | 34.18 | 98.23 |
| m3 | 0.05 | 0.21 | 68.3 | 0.18 | 0.66 | 0.84 | 78.95 |
| m4 | 0.11 | 0.28 | 65.3 | 0.32 | 0.81 | 1.12 | 71.79 |
| m5 | 0.16 | 0.52 | 58.6 | 0.39 | 1.26 | 1.64 | 76.47 |
| m6 | 0.02 | 0.03 | 70.1 | 0.08 | 0.09 | 0.17 | 52.94 |

In vitro erythroid differentiation of DBA CD34-5F iPSCs.

Figures 1F, 1G:
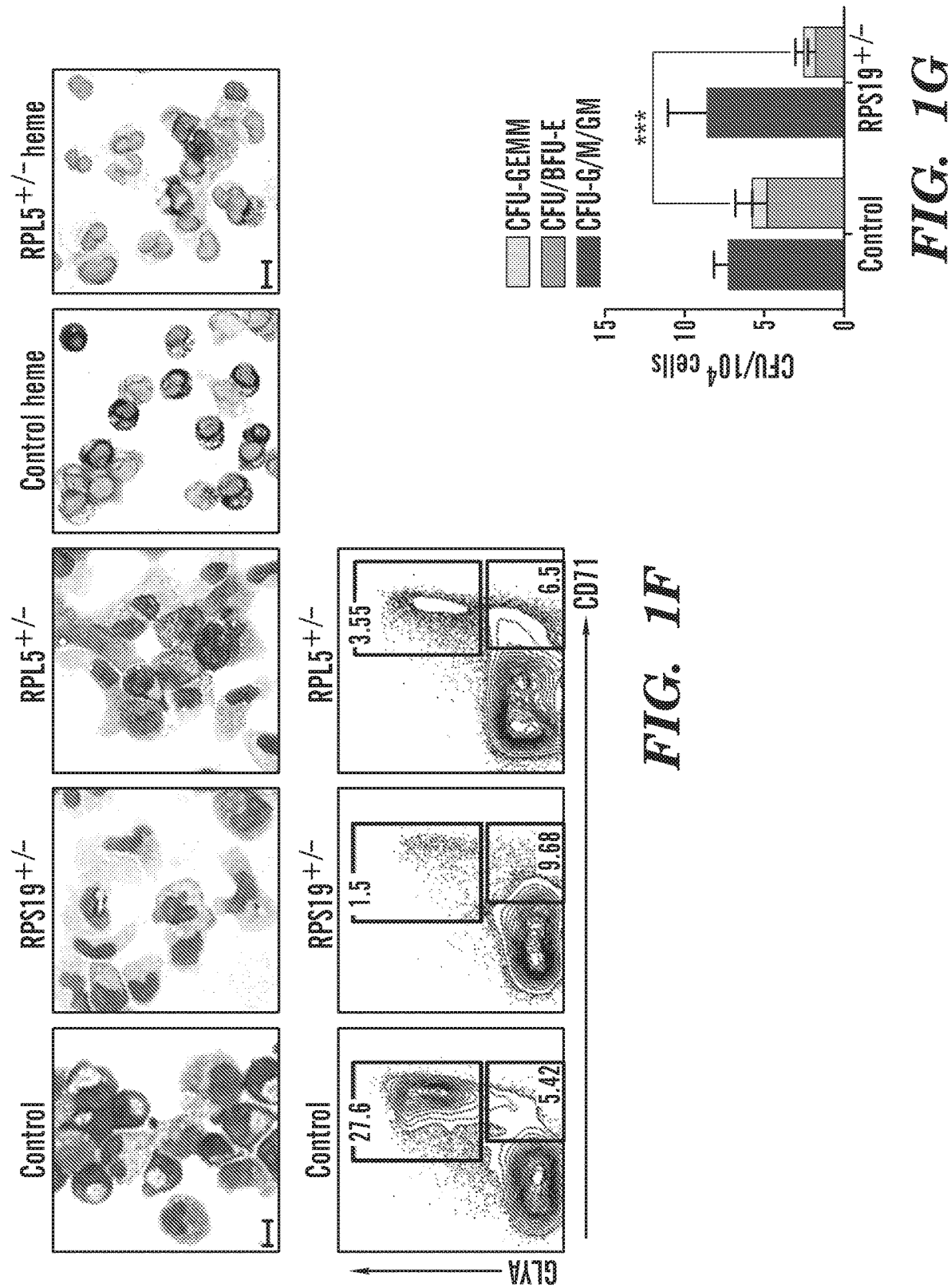
Figure 5A:
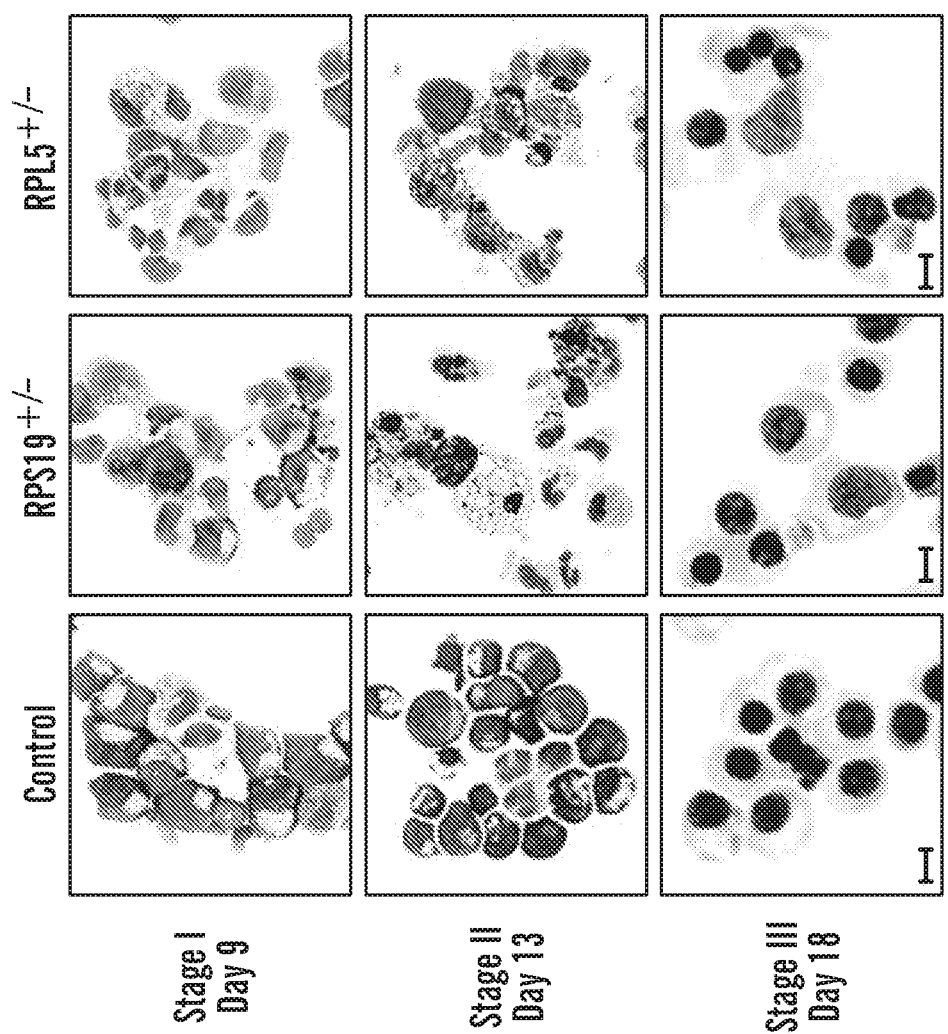

A block in differentiation at the early progenitor (BFU- or CFU-E) stage is a hallmark of DBA, which is characterized by failure of erythropoiesis and macrocytosis (Moniz et al., 2012; Nathan et al., 1978). The same phenomenon was observed during differentiation of DBA iPSCs using the CD34-5F system. Normal early erythroblasts are abundant and distinguished by basophilic cytoplasm because of their high ribosome content. By contrast, virtually no erythroblasts in differentiation of the RPS19 and RPL5 patient iPSCs (FIG. 1F) was found. The number and frequency of CD71⁺GlyA⁺ cells was also dramatically reduced (FIG. 1F bottom and FIGS. 5A and 5B). Furthermore, DBA CD34-5F cells generated normal numbers of myeloid, but reduced numbers of CFU- and BFU-E colonies indicating a specific loss of erythroid progenitors (FIG. 1G). DBA erythroblasts displayed a number of molecular changes characteristic of patient cells, including increased expression of p21 and the frequency of apoptotic cells (FIGS. 5C and 5D). Thus, the CD34-5F in vitro system recapitulates erythroid defects found in DBA.

In vivo erythropoiesis from DBA CD34-5F iPSCs

Figure 7A:
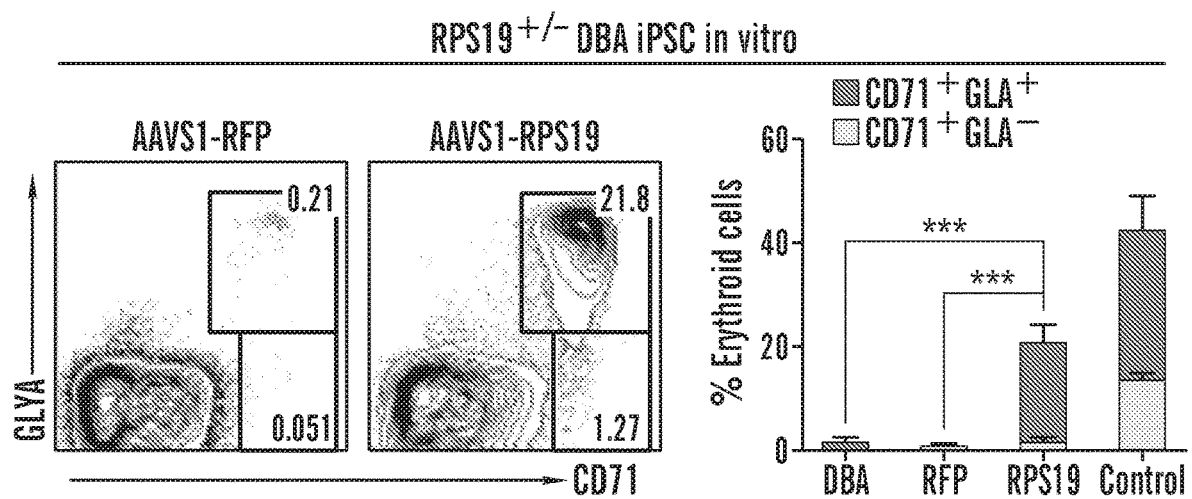
FIGS. 7A-7C show gene complementation of DBA iPSCs.
Figure 7B:
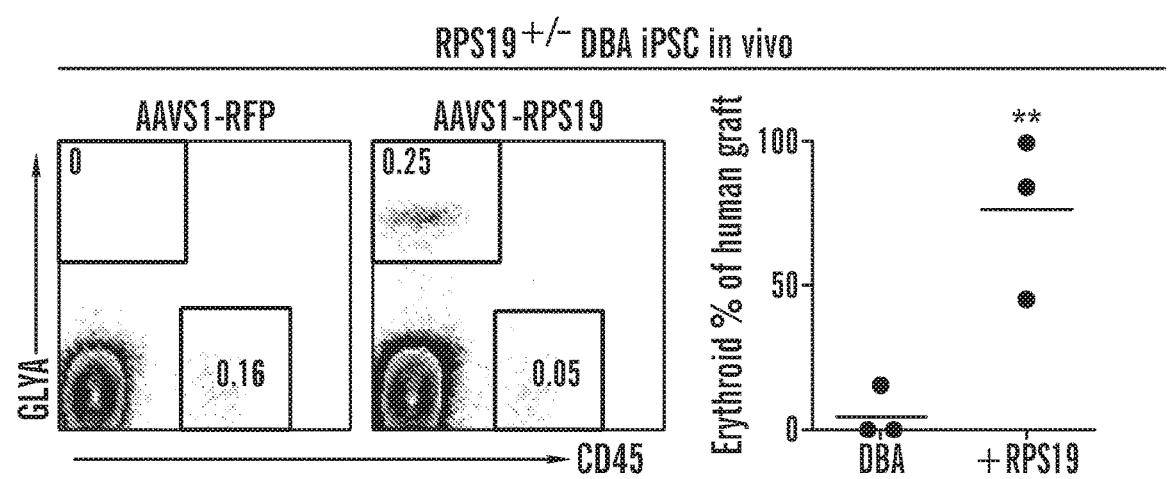
Figure 7C:
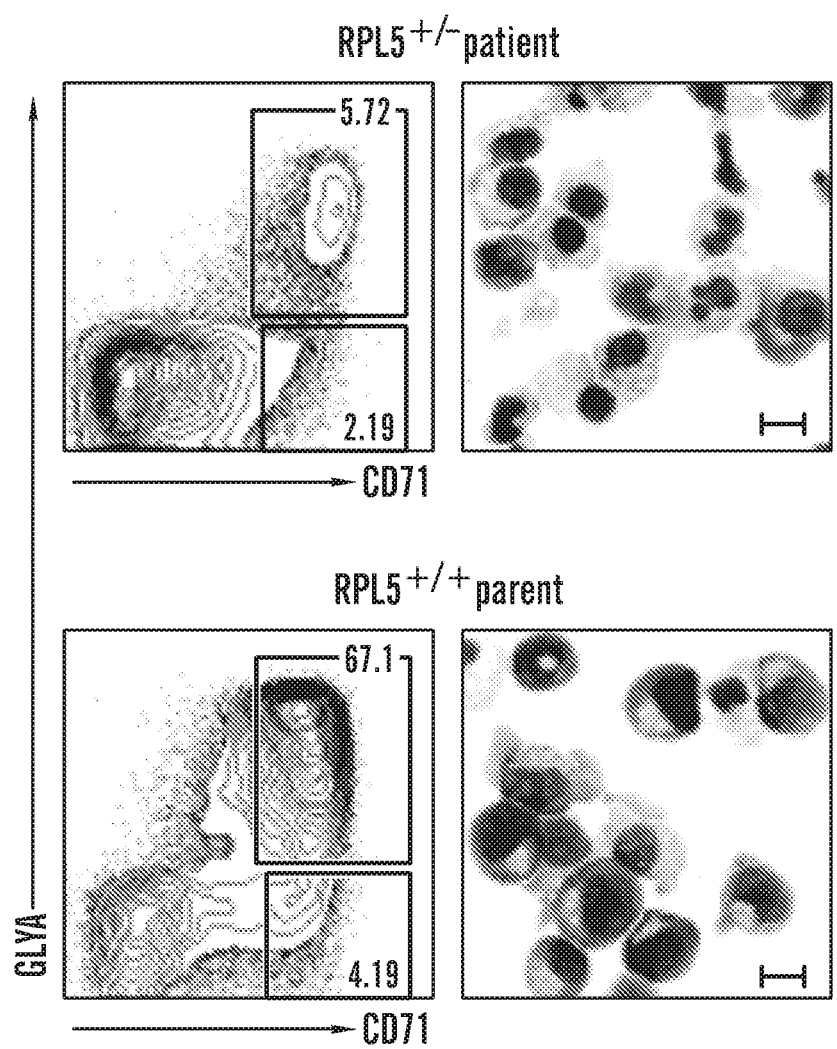

To assess the erythroid potential of DBA iPSCs in vivo, CD34-5F cells were transplanted into adult NSG mice. Four weeks after transplant, CD34-5F cells from normal iPSCs gave rise to both GlyA⁺ CD45⁻erythroid and GlyA⁻CD45⁺ myeloid engraftment (FIG. 2A). By contrast, DBA CD34-5F cells gave rise to myeloid, but little erythroid engraftment (FIG. 6A, FIG. 5E, and FIG. 2). The human erythroid graft consisted predominantly of mature orthochromatic normoblasts and some enucleated reticulocytes (FIG. 6B), consistent with previous observations that iPSC-derived cells undergo maturation and globin switching in vivo (Doulatov et al., 2013). As engraftment capacity differed for each iPSC line, the proportion of erythroid cells relative to the total human graft were monitored in order to normalize RBC output. Normal iPSC-derived CD34-5F cells yielded 75 f 6.0% erythroid contribution, whereas CD34-5F cells from Gene Complementation of DBA iPSCs DBA is a monogenic disorder associated with mutations in ribosomal proteins. However, clinical heterogeneity and finding of ribosomal protein mutations in unaffected relatives suggests the existence of cooperating loci (Willig et al., 1999). To investigate the contribution of RPS19 to disease phenotype and to establish more stringent controls, we used CRISPR/Cas9 to insert a single copy of RPS19, or an irrelevant RFP gene, into the AAVS1 locus. Multiple independent RPS19-complemented iPSC clones showed improved erythroid potential compared to starting DBA iPSCs and RFP controls in vitro (18.7%+1.97, 0.78%±0.52, and 0.98%+0.40 respectively) (FIG. 7A). However, the extent of rescue was lower compared to control iPSCs (42.6%). RPS19-complemented DBA progenitors also restored normal erythroid engraftment in vivo (FIG. 7B). To independently validate our model, we generated iPSCs from the unaffected parents of the RPL5 patient. Parental lines displayed normal erythroid differentiation (FIG. 7C) indicating that defective erythropoiesis is likely due to the RPL5 mutation rather than other haploidentical mutations. These data show that insertion of a single copy of RPS19 can restore erythropoiesis in DBA. The lack of complete normalization by gene replacement suggests that our method of gene correction may not achieve optimal gene dosage for RPS19, or that additional modifier loci contribute to inefficient erythropoiesis in DBA patients.

Large Scale Chemical Screens to Rescue Erythroid Differentiation

Figure 8A:
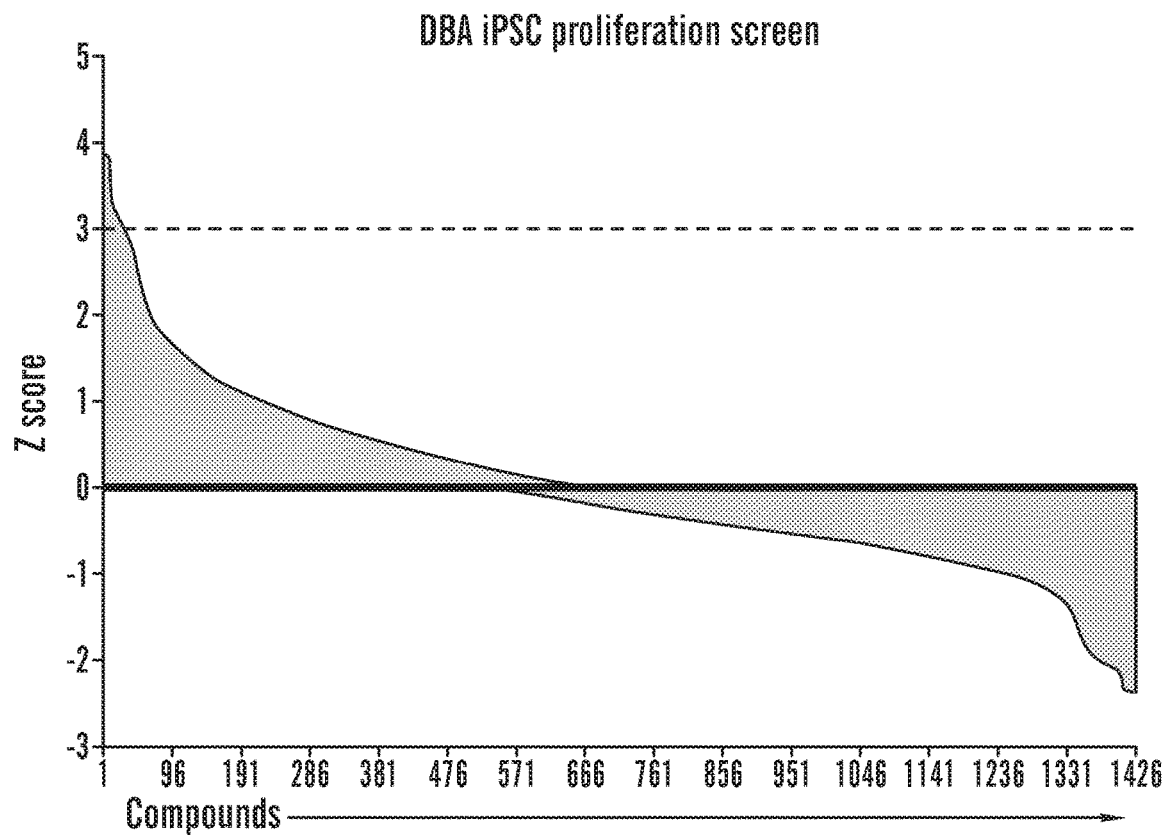
FIGS. 8A-8D shows chemical screens used to identify compounds that rescue defective erythropoiesis.
Figure 8B:
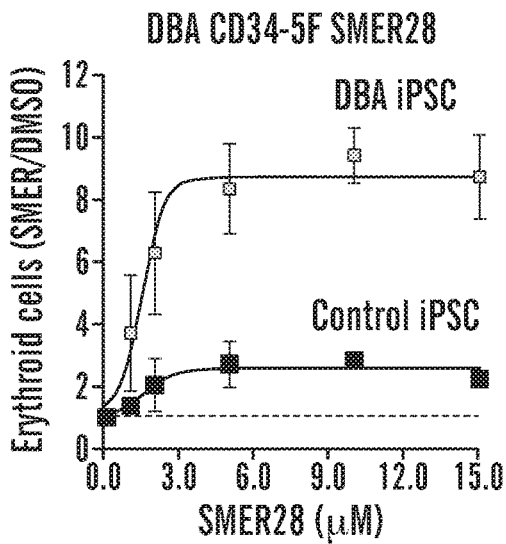
Figure 8C:
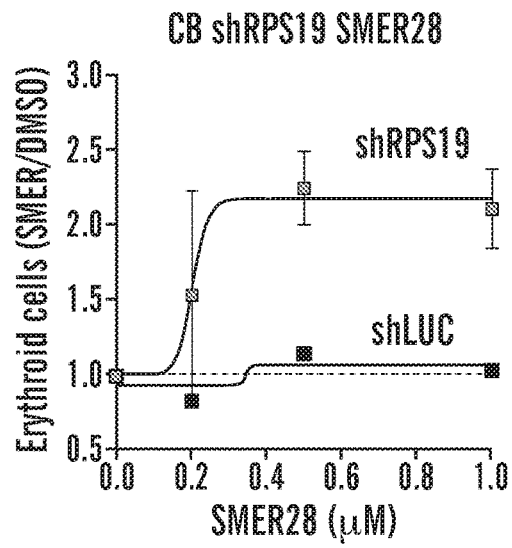
Figure 8D:
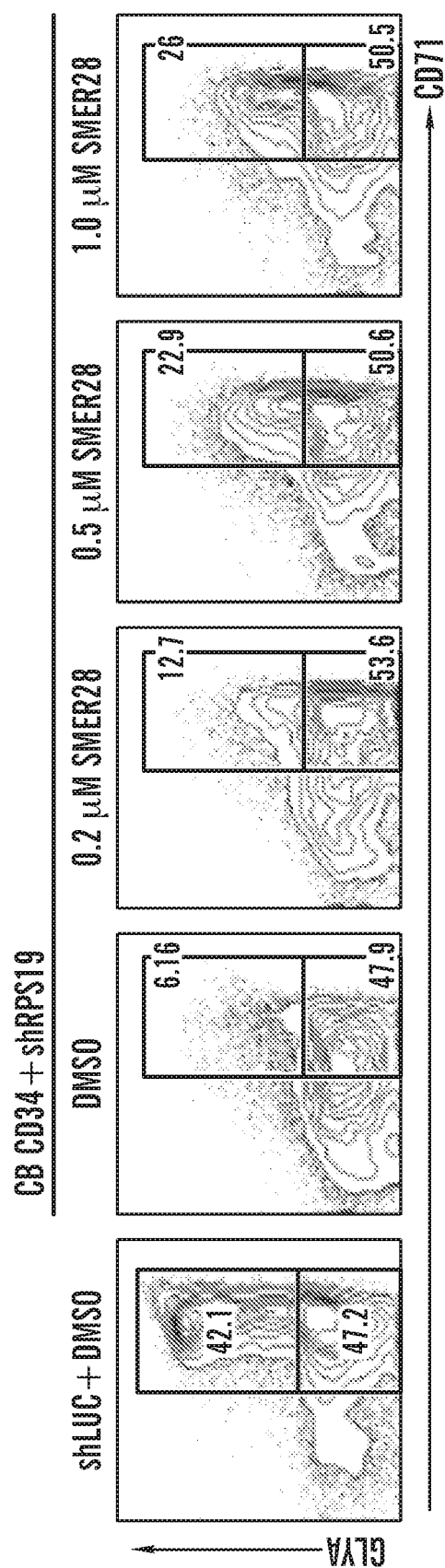
Figure 9A:
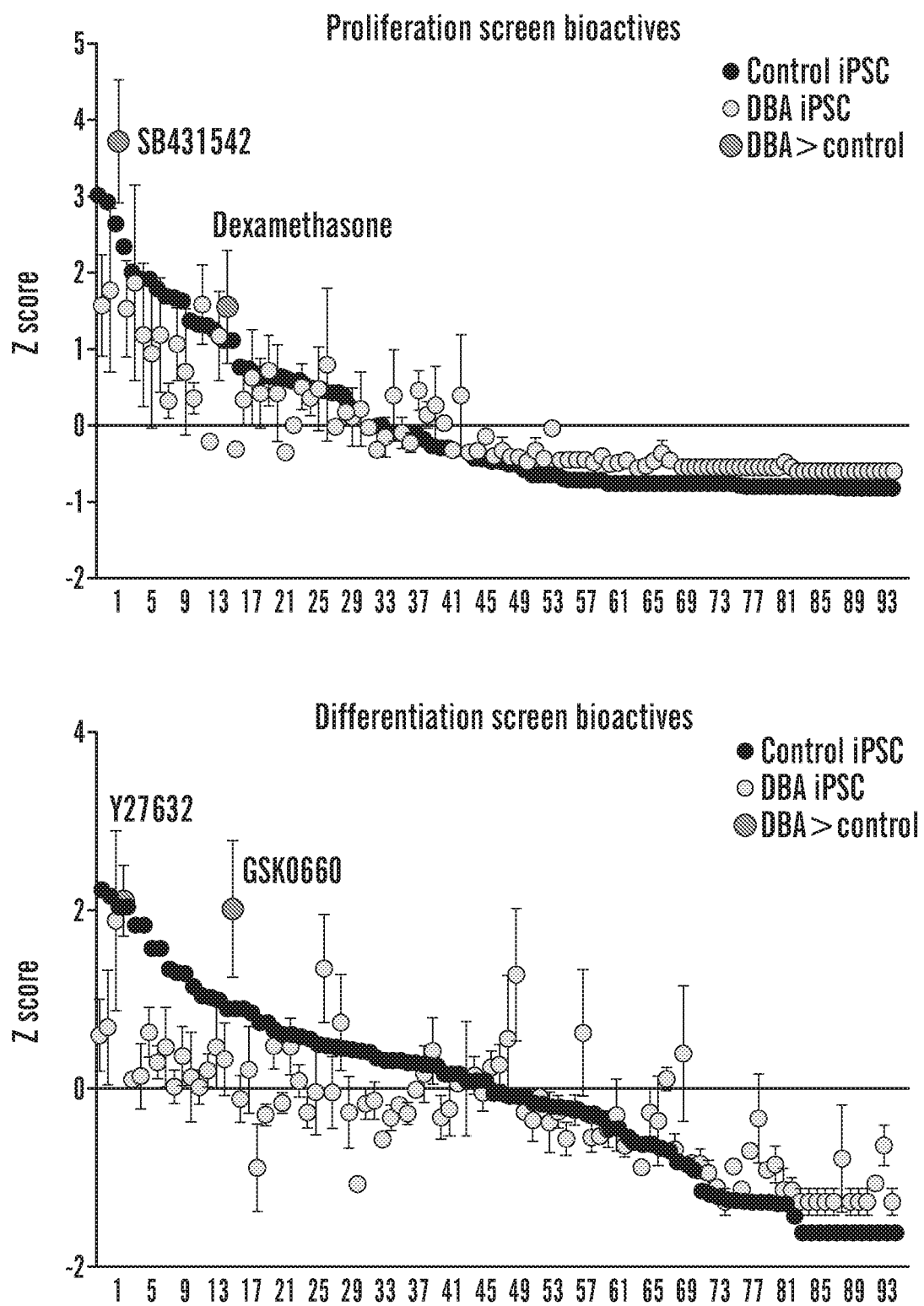
Figure 9C:
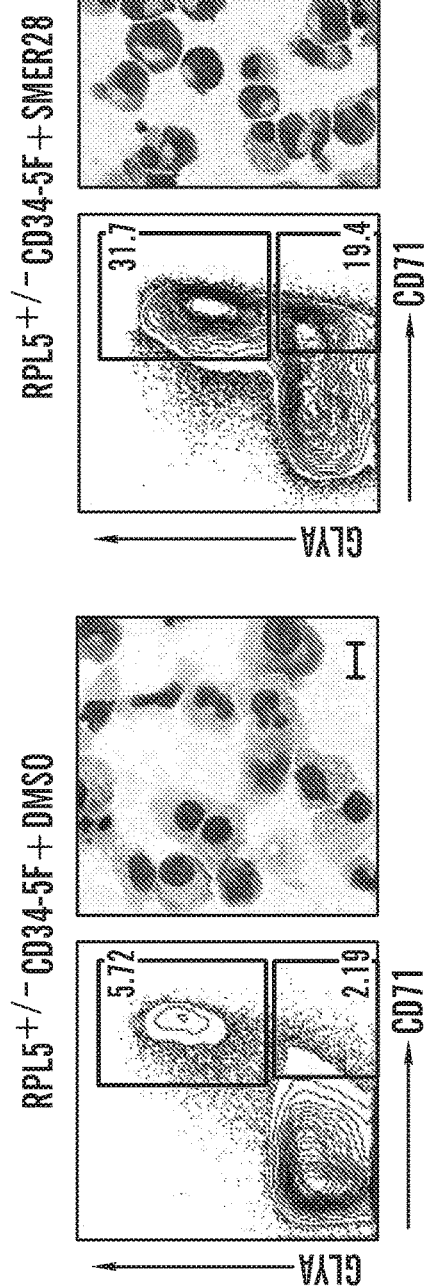
Figure 9D:
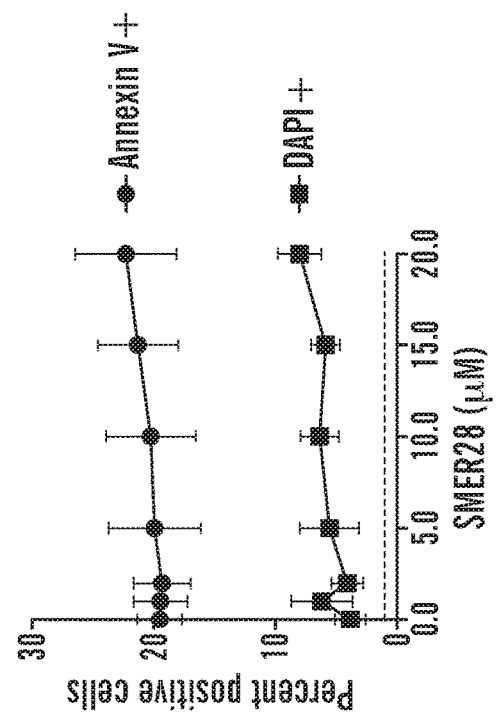

To discover novel therapeutics for DBA, strategies to screen for enhanced proliferation or differentiation of RBCs differentiated from DBA CD34-5F progenitors were developed as described below in the Experimental Procedures. Sigma LOPAC library of 1280 pharmacologically active small molecules were screened, plus 160 selected bioactive compounds (1440 in total), at a concentration of 5 µM, and found compounds that target calcium signaling and autophagy among the top hits (FIG. 8A, and FIGS. 9A and 9B). SMER28, a quinazolinamine derivative previously shown to modulate autophagy (Sarkar et al., 2007), displayed the most profound dose-dependent effect on erythroid differentiation and was characterized further. SMER28 increased the absolute number of CD71$^+$GlyA$^+$erythroid cells from RPS19$^{+/-}$ and RPL5 DBA iPSCs in a dose-dependent manner with the EC$_{50}$ of 1.5 μM (95% confidence interval: 0.63 to 2.37 μM) (FIGS. 8B and 9C). Cytotoxicity at drug doses up to 20 μM (FIG. 9D) was not observed. SMER28 had a smaller effect on control iPSCs (DBA=9.8-fold; control=2.5-fold; EC$_{50}$=1.6 μM) (FIG. 4B). To confirm SMER28 activity in an independent model of DBA, CB CD34$^+$ progenitors were transduced with shRNAs for RPS19 (RPS19). As expected, RPS19$^{sh}$ suppressed erythroid differentiation, and treatment with SMER28 robustly increased erythroid output of RPS19' cells, with the highest activity at lower doses of the drug (FIGS. 8C and 8D). These data suggest that SMER28 promotes erythropoiesis in both normal and DBA cells, with a greater proportional response in diseased cells.

SMER28 Enhances Erythropoiesis In Vivo.

Figure 10A:
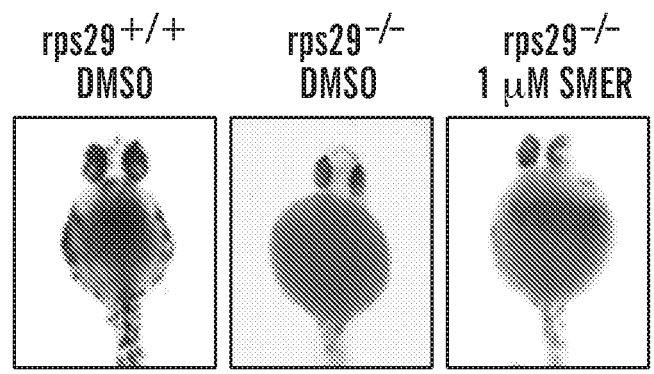
FIGS. 10A-10F shows that SMER28 promotes erythropoiesis in vivo.
Figure 10B:
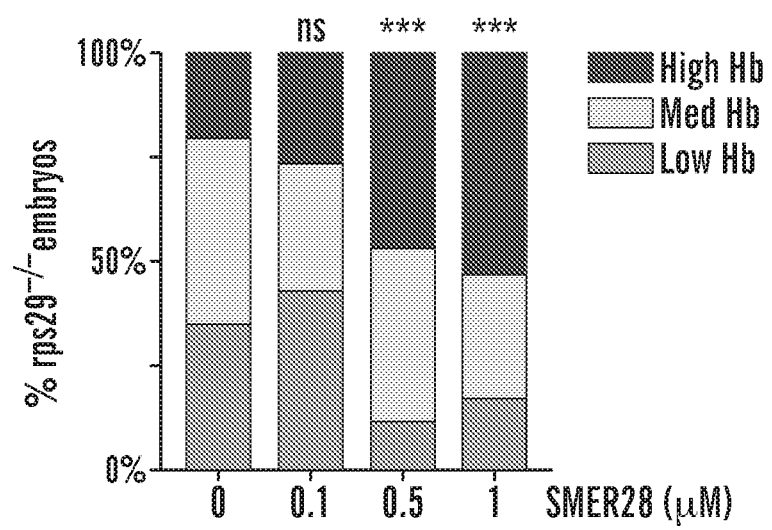

Zebrafish represent an attractive first model for testing potential therapeutic compounds due to ease of drug delivery into the water. Mutations in ribosomal proteins, e.g. Rps29, cause DBA-like anemia in zebrafish (Taylor et al., 2012). RPS29 is also mutated in a subset of DBA patients (Mirabello et al., 2014). Rps29$^{-/+}$ zebrafish have profound anemia, which can be revealed by hemoglobin staining in the yolk sac. Zebrafish embryos treated with SMER28 for 40 hpf showed a robust increase in hemoglobin staining (FIG. 10A). Over 50% of embryos treated with 1 μM SMER28 showed high levels of hemoglobin, compared to 20% for vehicle-treated controls, p<0.05, (FIG. 10B). Thus, SMER28 ameliorates anemia in an in vivo disease model of DBA.

Figure 10C:
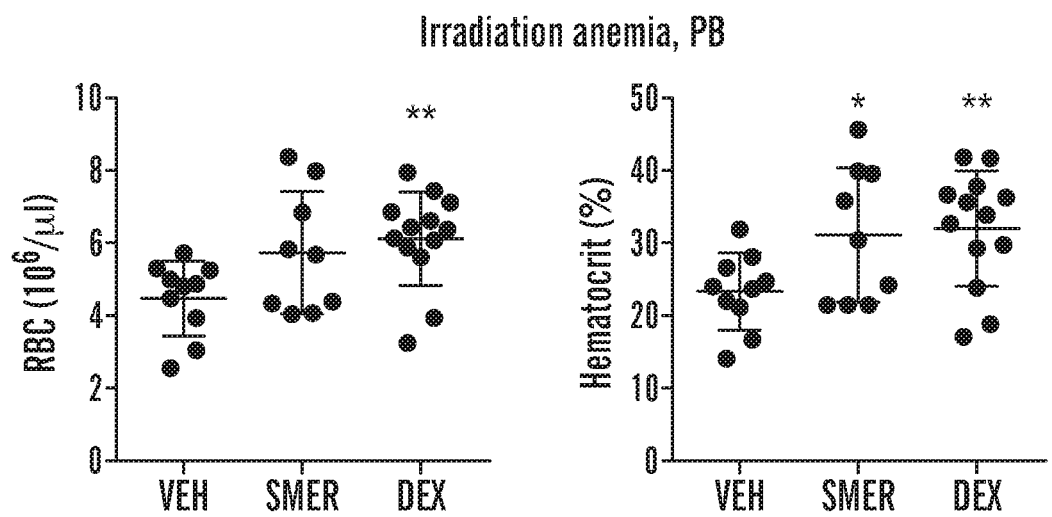
Figure 10D:
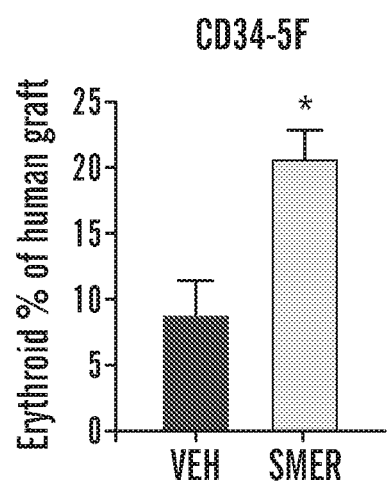
Figure 10E:
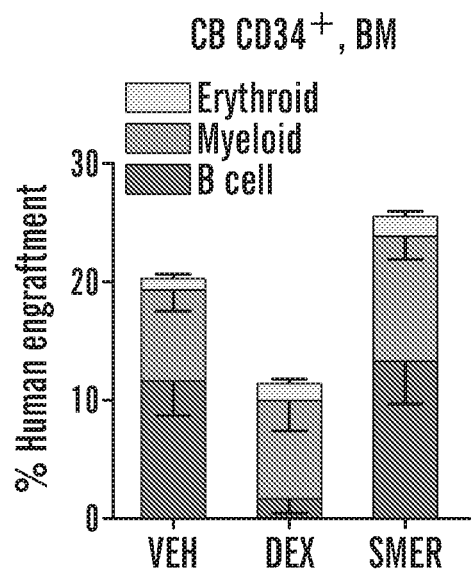
Figure 10F:
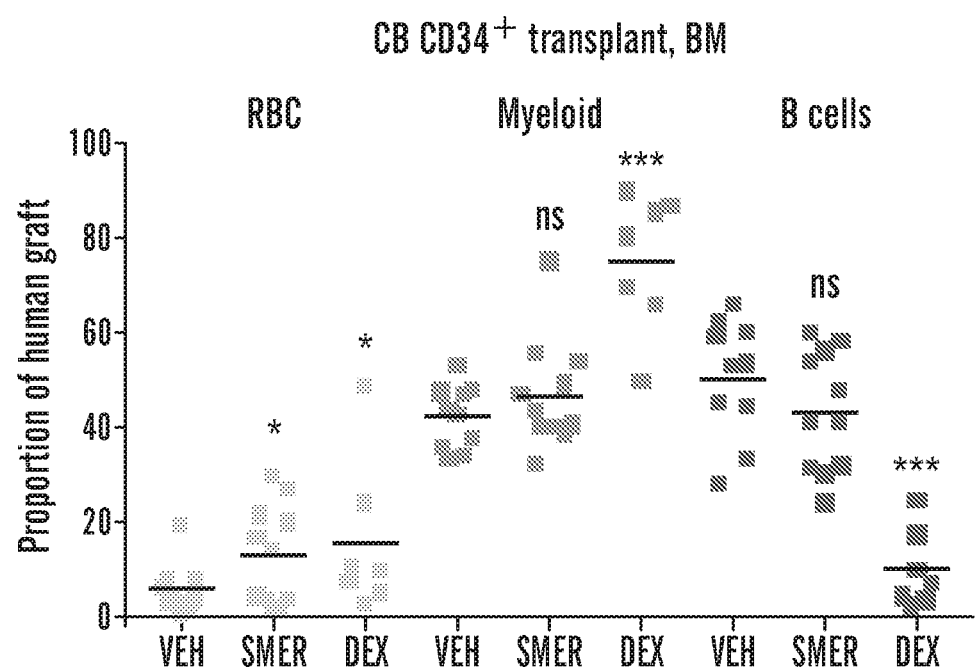

In following evaluation, the effects of administration of SMER28 to mice with irradiation-induced anemia, a model that enables dose-finding and initial testing of safety and bioactivity. The drug was well tolerated in dose escalation up to 20 mg/kg with no overt toxicity. To assess bioactivity, we measured the levels of autophagic marker LC3 in treated animals. LC3-I and LC3-II levels were modestly increased in the liver indicating drug activity in vivo (FIG. 11A). Sub-lethally irradiated mice treated with 10 mg/kg SMER28 had modestly elevated peripheral blood RBC counts (p=0.07) and hematocrit (p=0.04) compared to vehicle controls, although Dex steroid treatment induced a more robust response (p=0.003). (FIG. 10C). We tested the effect of this compound on human cells by treating NSG mice transplanted with human CD34-5F and CB cells. SMER28 increased the output of GlyA$^+$ RBCs from DBA CD34-5F cells (FIG. 10D). Mice transplanted with CB CD34$^+$ cells administered 2 mg/kg SMER28 for 4 weeks trended towards higher human chimerism (19.5% vs 25.2%; ns), and erythroid contribution to human graft (13.0% vs 5.5% RBCs as proportion of human graft; p=0.05) (FIGS. 10E and 10F). While Dex also increased RBC output (10.4%; p=0.04), it nearly abolished human B cells consistent with its lymphotoxic effects (FIG. 10E). By contrast, SMER28 was specific to erythroid cells, and did not affect the distribution of myeloid and lymphoid lineages (FIG. 10F). These data establish preliminary in vivo efficacy of SMER28. While we cannot rule out the effects of irradiation-induced inflammation and tissue damage, the robust effect of SMER28 on RBCs in vitro suggests that it directly promotes erythropoiesis in vivo.

SMER28 Acts on CD34$^+$ Erythroid Precursors.

Figure 12D:
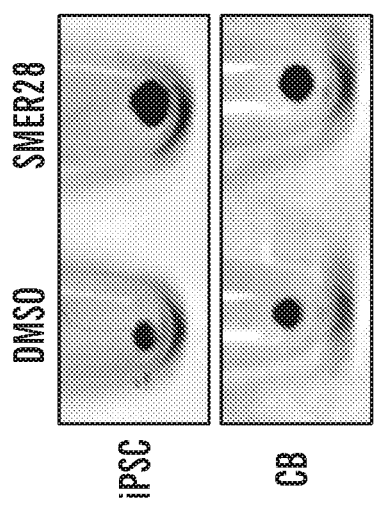

Erythropoiesis is a multi-step process initiated by erythroid precursors and culminating with enucleated RBCs. A key advantage of the CD34-5F system is that cells initiate differentiation in a synchronous manner after Dox withdrawal. To identify the cell types responsive to SMER28 in this developmental process, we treated CD34-5F cells during sequential stages of erythropoiesis. CD34$^+$ progenitors treated only during the initial expansion phase displayed increased output of GlyA$^+$ cells (FIGS. 12A and 12B); absolute numbers in (FIG. 11B). Both DBA progenitors and, to a lesser extent, normal progenitors were responsive (FIG. 12B). By contrast, treatment of erythroblasts during stage I did not significantly increase the number of GlyA$^+$ cells; instead, it primarily expanded CD71$^+$GlyA$^-$ pre-erythroblasts (FIG. 12B; 'stage I'). We validated these findings in the CB CD34$^+$ model. SMER28 treatment of undifferentiated CD34$^+$ RPS19$^{sh}$ cells was sufficient to improve erythroid output (FIG. 12C). These data indicate that SMER28 acts on CD34$^+$ progenitors to promote erythroid differentiation.

Figure 12E:
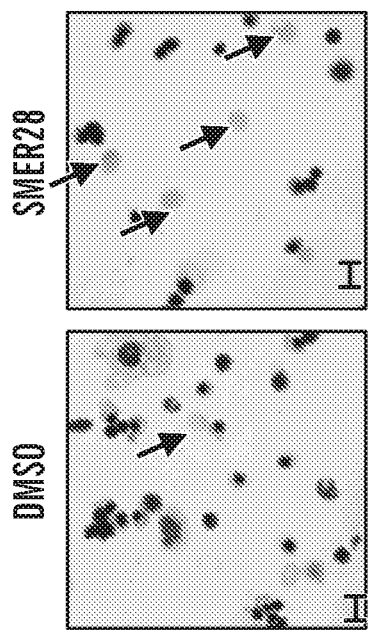
Figure 12F:
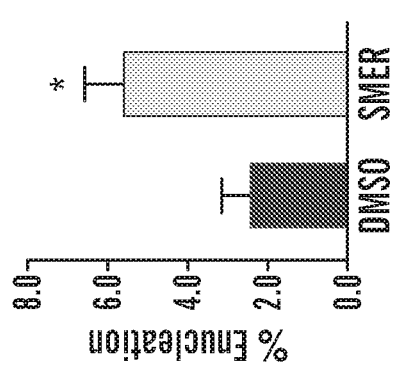

Erythroblasts proliferate rapidly to give rise to terminally differentiated RBCs. While SMER28 treatment of CD34$^+$ progenitors generated more erythroblasts, their output of RBCs was comparable to vehicle controls. By contrast, treatment of erythroblasts during stages I-III of differentiation enhanced the output of iPSC- and CB-derived mature RBCs (FIG. 12D), and increased the efficiency of enucleation (2.4%±1.2 vs 5.6%±1.6) (FIGS. 12E and 12F). These data indicate that SMER28 acts on immature erythroid precursors and mature erythroblasts to increase generation of RBCs.

SMER28 Acts Via Autophagy Factor Atg5/LC3.

Figure 13A:
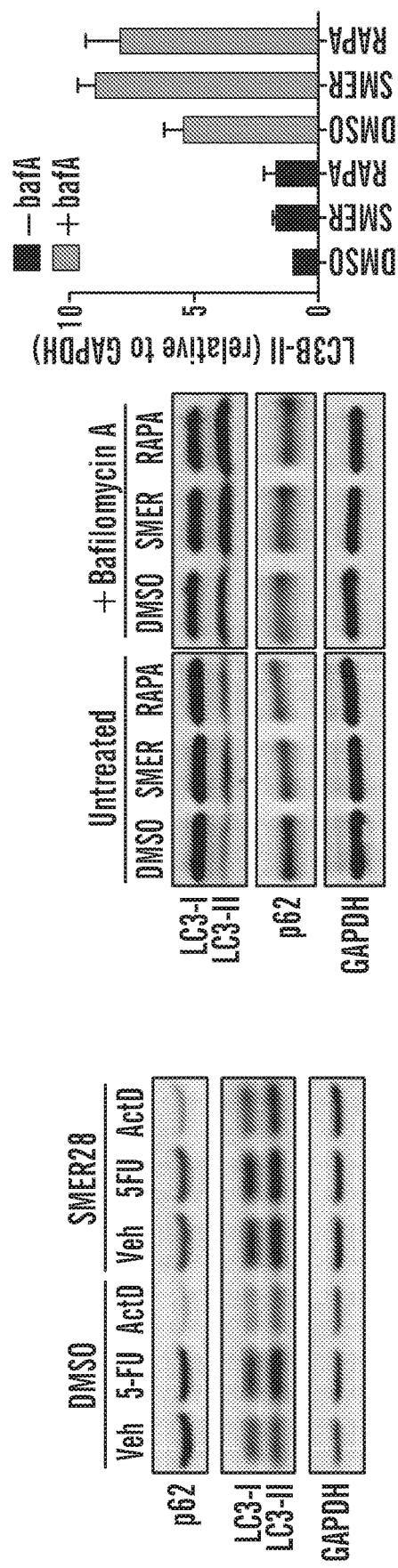
FIGS. 13A-13D shows that SMER28 induces autophagy.
Figure 13B:
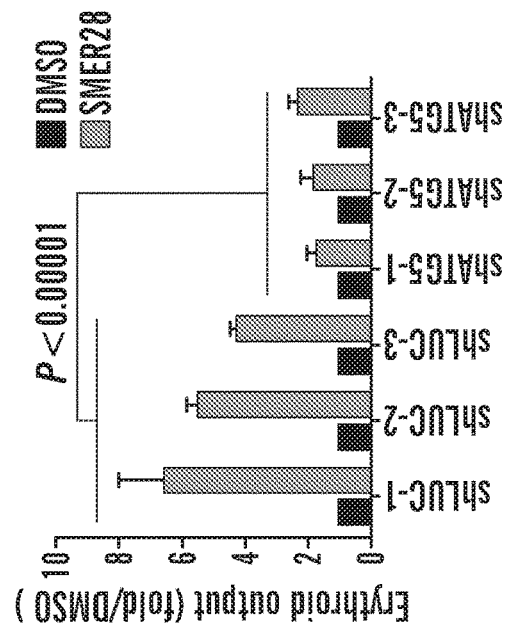

SMER28 was identified as an mTOR-independent inducer of autophagy, by synergizing with rapamycin to promote clearance of protein aggregates in models of neurodegenerative disease (Sarkar et al., 2007; Tian et al., 2011). Autophagy is a pro-survival pathway induced by a variety of stresses, such as nutrient limitation or protein aggregation. Autophagy is required for clearance of mitochondria during terminal erythroid maturation (Mortensen and Simon, 2010), but has not been linked with earlier stages of erythropoiesis. To determine if SMER28 modulates autophagy in erythroid cells, we interrogated the levels of p62 and LC3 in K562 erythroleukemia cells transduced with shRPS19. SMER28 reduced p62 and increased the levels of updated LC3-II isoform associated with autophagosomes (FIG. 13A). Conversion of cytosolic LC3-I into updated LC3-II was also induced by cytotoxic 5-fluorouracil, and occurred in the presence of actinomycin D, indicating that the conversion did not require transcription (FIG. 13A). To measure autophagic flux, we monitored LC3-II levels after blocking lysosomal fusion with bafilomycin A. SMER28 increased LC3-II levels following lysosomal blockade, similarly to the mTOR inhibitor rapamycin (FIG. 13B). These data show that SMER28 increases autophagic flux in erythroid cells.

Figure 13C:
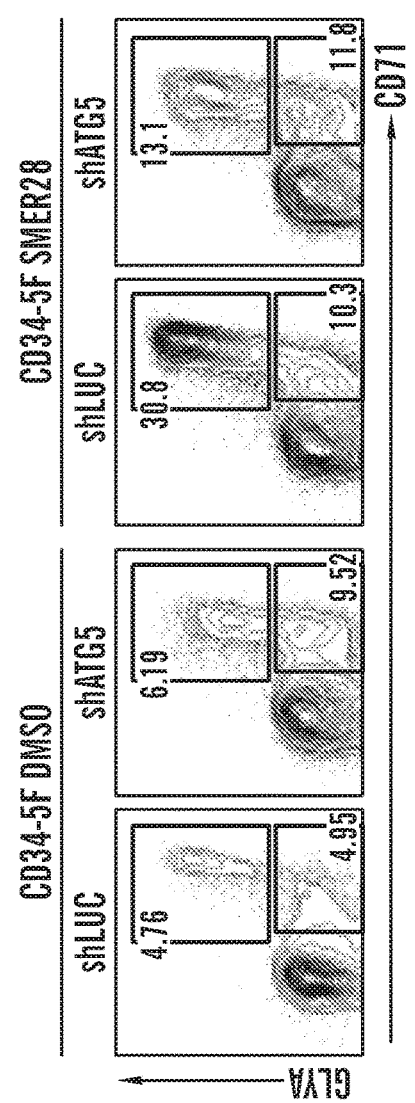
Figure 13D:
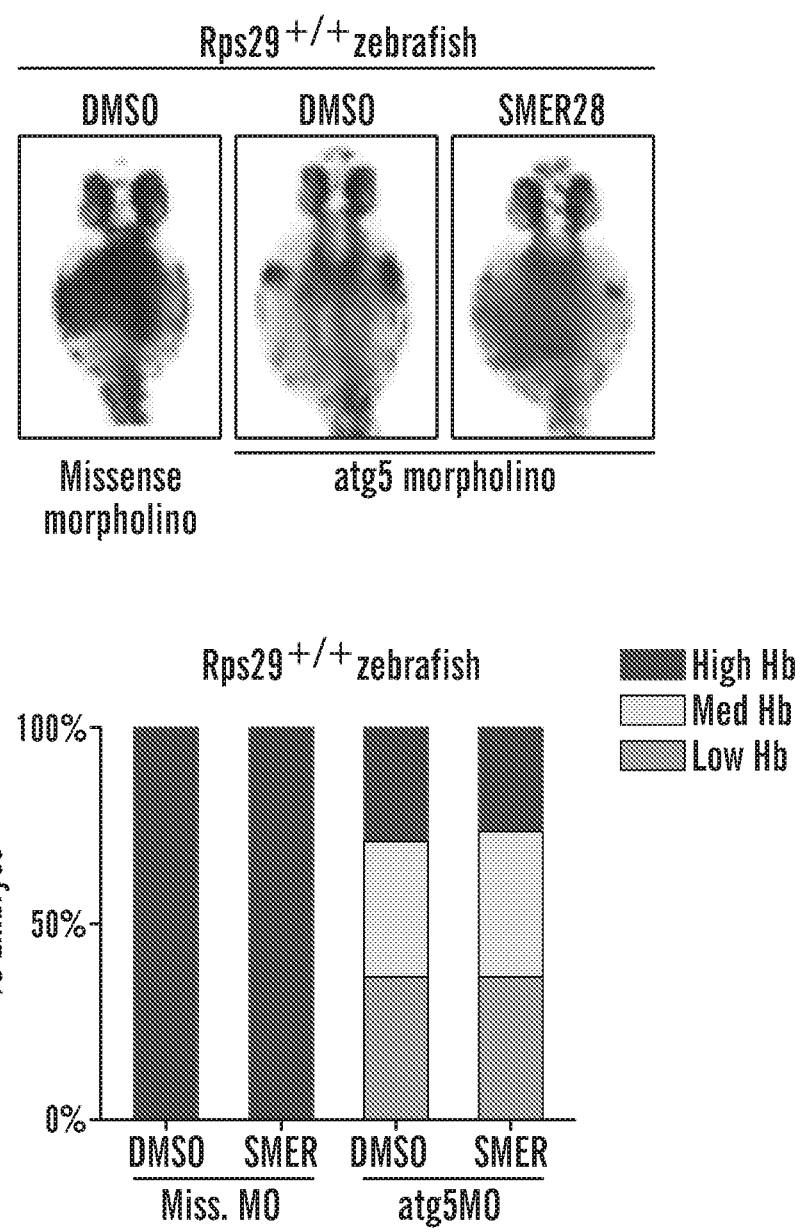

To test if autophagy factors are required for SMER28 function, we transduced CD34-5F progenitors with multiple shRNAs for ATG5 (ATG5'), which is required for LC3 lipidation and autophagosome assembly. Knockdown of ATG5 significantly reduced the effect of SMER28 on erythroid differentiation (p=0.005), indicating that ATG5/LC3 is required for its effects on erythropoiesis (FIG. 13C). To test the role of Atg5 in erythropoiesis, we depleted atg5 in zebrafish using a previously reported morpholino (Hu et al., 2011). We titrated down the doses of atg5 morpholino to eliminate non-specific morpholino toxicity. Injection of atg5, but not missense, morpholino markedly reduced hemoglobin staining in wild-type zebrafish (FIG. 13D). Moreover, atg5 knockdown in rps29$^{+/-}$ zebrafish abolished the rescue of erythropoiesis by SMER28 (FIG. 13D). Taken together, these findings indicate that autophagy factor Atg5 is required for erythropoiesis, and SMER28 acts by inducing LC3 lipidation via Atg5, suggesting that it activates autophagy to promote differentiation of erythroid prog.

Table 3. List of significant hits from the chemical library screen. List of the hit compounds screened from the screen of Signma LOPAC chemical library and a library of selected bioactive compounds (1440 total). DBA34-5F cells were plated in erythroid-promoting conditions in 384-well format. Erythroid proliferation was measured in the presence of 5 µM of each compound. Hits were defined by the combined Z-score >3 for two independent DBA iPSC lines, and preferential effect against DBA compared to normal cells (2 normal iPSC lines).

TABLE 3

| Hit compound | Biological function |
| --- | --- |
| 8-MIMX | Calmodulin-PDE1 inhibitor |
| Cilnidipine | Calcium channel inhibitor |
| Carbamazepine | Calcium signaling inhibitor |
| Sodium taurocholate | Taurine biosynthesis |
| Pyrilamine maleate | H1 histamine reverse agonist |
| Aminoresveratrol sulfate | SIRT1 activator |
| 1-Aminobenzotriazole | Cytochrome P450 inhibitor |
| SMER28 | Inducer of autophagy |
| A3 hydrochloride | Casein kinase inhibitor |
| Bicalutamide (CDX) | Androgen receptor inhibitor |
| EHNA | Adenosine deaminase inhibitor |
| SB431542 | TGFβ inhibitor |
| Dexamethasone | Glucocorticoid agonist |
| DAPT | Inhibitor of γ-secretase |
| AGK2 | SIRT2 inhibitor |
| IWP-2 | Inhibitor of Wnt secretion |
| DLPC | NR5A2 agonist |
| Troglitazone | PPARγ receptor agonist |
| Splitomycin | SIRT2 inhibitor |
| Y27632 | ROCK1 kinase inhibitor |
| EBPC | Aldose reductase inhibitor |
| Mibefradil dihydrochloride | Calcium channel inhibitor |

DISCUSSION

Reprogramming to induced pluripotency is a powerful approach to modeling disease that enables drug screening against pathologic human cellular phenotypes. To test prospective therapeutics, iPSCs must first be differentiated into disease-relevant cell types, such as dopaminergic neurons, cardiomyocytes, or red blood cells. Since mature cell types lack proliferative capacity, differentiation protocols must be massively scaled up, which presents a challenge for obtaining adequate and consistent cell populations to perform drug screens. As a result, most studies to date have surveyed known therapeutics or tested limited numbers of drug candidates (Avior et al., 2016; Engle and Vincent, 2014; Grskovic et al., 2011). An alternative approach to enable large-scale drug screens involves isolating and expanding intermediate progenitors to serve as a defined scalable source of target cells (Doulatov and Daley, 2013; Sterneckert et al., 2014). While isolation of progenitors has been reported for neural, cardiac, and endodermal lineages (Cheng et al., 2012; Li et al., 2011), these have not to date been used for chemical screening.

Patient-specific iPSCs have been characterized for many hematological diseases, including anemias, neutropenia, myeloproliferative disease, CML, and immunodeficiencies (Garcon et al., 2013; Kumano et al., 2012; Nayak et al., 2015; Saliba et al., 2013; Tulpule et al., 2013; Vo and Daley, 2015). While HPCs can be obtained by directed differentiation, these progenitors are largely myeloid lineage-restricted and lack proliferative and engraftment potential. As a result, unbiased drug screens for hematological diseases have not been reported to date. To overcome this limitation, directed differentiation was combined with transcription factor reprogramming to endow multi-lineage iPSC-derived HPCs with self-renewal potential (Doulatov et al., 2013). CD34-5F cells can be maintained as progenitors, induced to differentiate into transfusion-scale quantities of RBCs, and engrafted in vivo. As a proof of principle, this platform was applied to carry out unbiased chemical screens for anemia therapeutics using DBA as a genetically tractable model. It was demonstrated that SMER28 promotes erythropoiesis in multiple models of DBA in vitro and in vivo. These findings establish the iPSC progenitor model as a platform for drug discovery in hematological diseases. Alternative approaches involve generation of reversibly immortalized erythroid and megakaryocyte cell lines with MYC, BMI-1, and BCL-XL, or suppression of Gata1 (Hirose et al., 2013; Nakamura et al., 2014; Noh et al., 2015). These lines are a promising source of universal donor RBCs and platelets for clinical transfusion and might also prove useful for drug screening.

These findings show that SMER28 enhances erythropoiesis by stimulating autophagy. Autophagy plays important roles in development, homeostasis, and cancer, and is induced to cope with cellular stresses, such as nutrient deprivation (Galluzzi et al., 2014; Rubinsztein et al., 2012). The role of autophagy in hematopoiesis is only beginning to be elucidated. Autophagy serves a cytoprotective function in HSCs (Mortensen et al., 2011; Warr et al., 2013), and is required for clearance of mitochondria in terminal erythroid maturation (Mortensen and Simon, 2010). Expression of autophagic genes is directly activated by the erythroid master regulator GATA1 (Kang et al., 2012), however the role of autophagy in early erythroid development has not been established. SMER28 increases autophagic flux, measured by LC3 lipidation, in erythroid cells. In addition, loss of Atg5, which is required for LC3 lipidation and autophagosome assembly, blocks the effects of SMER28 on erythropoiesis in human and zebrafish models. Without wiching to be bound by a particular theory, it is possible that the Atg5/LC3 axis mediates these effects independently of autophagic cargo degradation, for example in LC3-assisted phagocytosis (Bestebroer et al., 2013; Kimmey et al., 2015).

Experimental Procedures

Patient samples and reprogramming. Skin fibroblasts were obtained by biopsy from patient T15 (UPN NCI 131-1) enrolled in an open cohort study (NCI 02-C-0052, ClinicalTrials.gov Identifier: NCT00027274) approved by the NCI Institutional Review Board. Skin fibroblasts were obtained from patient T5 according to the institutional guidelines approved by the Boston Children's Hospital Institutional Review Board. Patient fibroblasts were independently reprogrammed with episomal and Sendai virus delivery of pluripotency factors. Control iPSC lines used in this study were: CD45-IPSCand CD34-IPS, reprogrammed from normal donors, and MSC-IPS1 (Park et al., 2008). The episomal protocol was as previously described with modifications (Okita et al., 2011). The Amaxa nucleofector was used according to manufacturer instructions with 1 µg of each plasmid. After plating, media were changed every other day in MEF media for 6 days. At day 6, cells were split, and after 24 hours media were changed to KOSR-based human embryonic stem cell media (below). For Sendai reprogramming, fibroblasts were reprogrammed using the Cytotune iPSC Sendai Reprogramming Kit following manufacturer's instructions. All lines were characterized by karyotyping. The summary of iPSC lines is shown in Table 1.

iPSC Cultures. Human iPSC lines were maintained on Matrigel (BD) in mTeSR1 (StemCell Technologies) media. Media were changed daily and cells were passaged in a 1:8-1:10 ratio every 5-7 days using standard passaging techniques with Dispase (StemCell). Prior to initiating differentiation, colonies were passaged for one passage onto mouse embryonic fibroblasts (GlobalStem) in human embryonic stem cell media: DMEM/F 12+20% KnockOut-Serum Replacement (Invitrogen), 1 mM L-Glu, 1 mM NEAA, 0.1 mM β-mercaptoethanol, and 10 µg/ml bFGF.

EB differentiation. EB differentiation was performed as previously described (Chadwick et al., 2003). Briefly, iPSC colonies were scraped into non-adherent rotating 10 cm plates at the ratio of 2:1. The EB media was KO-DMEM+ 20% FBS (Stem Cell), 1 mM L-glutamine, 1 mM NEAA, penicillin/streptomycin, 0.1 mM β-mercaptoethanol, 200 µg/ml h-transferrin, and 50 µg/ml ascorbic acid. After 24 hrs, media was changed by allowing EBs to settle by gravity, and replaced with EB media supplemented with growth factors: 50 µg/ml BMP4 (R&D Systems), 300 µg/ml SCF, 300 µg/ml FLT3, 50 µg/ml G-CSF, 20 µg/ml IL-6, 10 µg/ml IL-3 (all Peprotech). Media was changed on days 5 and 10. EBs were dissociated on days 9-10 and day 14 by digesting with collagenase B (Roche), followed by treatment with enzyme-free dissociation buffer (Gibco), and filtered through an 80 µm filter. Dissociated EBs were frozen in 10% DMSO, 40% FBS freezing solution.

Lentivirus and shRNA plasmids. 5F lentiviral plasmids: HOXA9, ERG, RORA, SOX4, and MYB were in pinducer-21 Dox-inducible lentiviral vector (available from Addgene). shRNAs for RPS19 and ATG5 were purchased from Open Biosystems in pLKO.1-TurboGFP lentiviral vector. TFR1 (TFRC) overexpression constructs were purchased from GeneCopoeia: IMAGE: 100005489 and NM_001128148.1. Both constructs were verified to have identical sequence containing only the 2283 bp ORF. Lentiviral particles were produced by transfecting 293T-17 cells (ATCC) with the lentiviral plasmids and 3rd-generation packaging plasmids. Virus was harvested 24 hours after transfection and concentrated by ultracentrifugation at 23,000 rpm for 2 hrs. All viruses were titered by serial dilution on 293T cells.

Progenitor sorting. Dissociated EB cells were thawed using Lonza Poietics protocol (http://bio.lonza.com/uploads/tx_mwaxmarketingmaterial/Lonza ManualsProductInstructions Procedure_for_Thawing_Poietics_Cells.pdf) and resuspended at $1\times10^6$/100 µl staining buffer (PBS+2% FBS). Cells were stained with a 1:50 dilution of CD45 PE-Cy5 (Immu19.2; Clontech), CD34 PE-Cy7 (8G12; BD), and DAPI for 20 min at RT. All sorting was performed on a BD FACS Aria II cell sorter using a 70 µm nozzle.

5F gene transfer and CD34-5F culture. Sorted CD34$^+$ CD45+EB progenitors were seeded on retronectin-coated (10 µg/cm$^2$) 96 well plates at a density of $2\text{-}5\times10^4$ cells per well. The infection media was SFEM (StemCell) with 50 µg/ml SCF, 50 µg/ml FLT3, 50 µg/ml TPO, 50 µg/ml IL6, 10 µg/ml IL3 (all R&D Systems). Lentiviral infections were carried out in a total volume of 150 µl. The multiplicity of infection (MOT) for the factors was MOI=5 for ERG and HOXA9, and MOI=3 for RORA, SOX4, and MYB. Virus was concentrated onto cells by centrifuging the plate at 2500 rpm for 30 min at RT. Infections were carried out for 24 hrs. After gene transfer, CD34-5F cells were cultured in SFEM with 50 µg/ml SCF, 50 µg/ml FLT3, 50 µg/ml TPO, 50 µg/ml IL6, and 10 µg/ml IL3 (all R&D Systems). Dox was added at 21 g/ml (Sigma). Cultures were maintained at a density of $<1\times10^6$ cells/ml, and media were changed every 3-4 days. After 14 days of culture, CD34-5F were plated in the erythroid protocol or transplanted in vivo.

Erythroid differentiation. Differentiation was performed essentially as described (Lee et al., 2015). CD34 expansion phase (4 days): To initiate differentiation CD34-5F cells were cultured in progenitor media without Dox. Stage I (5 days): Media were changed to: IMDM+1% BSA (Gibco), 20% FBS (Stem Cell Technologies), 1 mM L-glutamine, penicillin/streptomycin, 500 µg/ml h-transferrin (Sigma), 10 µg/ml human insulin (CellSciences), 1 µM β-estradiol, 1 µM Dex, 6U Epo (CellSciences), 100 µg/ml SCF, and 5 µg/ml IL-3. Cells were seeded at a density of $<1\times10^5$ cells/ml in 24-well plates. Stage 11 (4 days). Media were changed to: IMDM+1% BSA, 20% FBS, 1 mM L-glutamine, penicillin/ streptomycin, 500 µg/ml h-transferrin, 10 µg/ml human insulin, 6U Epo, and 50 µg/ml SCF. Cells were seeded at a density of $<2\times10^5$ cells/ml in 24-well plates. Stage III (10 days) Media were changed to: IMDM+1% BSA, 20% FBS, 1 mM L-glutamine, penicillin/streptomycin, 500 µg/ml h-transferrin, 10 µg/ml human insulin, and 2U Epo. Cells were seeded at a density of $<5\times10^5$ cells/ml in 24-well plates.

Large-scale chemical screens. The LOPAC 1280 library of pharmacologically active small molecules was purchased from Sigma. Compounds were provided at a 10 mM concentration in the 384 or 96 well format. Each plate was diluted to 10 µM in erythroid stage I media. CD34-5F cells from two control and four DBA iPSCs were plated at 1000 cells/well into glass-bottom 96 well plates, or 250 cells/well in 384 well plates (Greiner). Equal volume of diluted compound was added using a liquid robotic handler such that the final concentration was 5 µM. For proliferation screen, cells were cultured for 9 days, and erythroid growth was measured in a plate reader using the ATP-Lite kit (Perkin-Elmer). For differentiation screen, cells were cultured for 7 days, and stained with the panel of erythroid antibodies (see Flow cytometry). Each plate was acquired on BD LSR-II cytometer equipped with a high-throughput sampler to measure percent CD71 GlyA$^+$erythroid cells. From either screen, raw values for each plate were converted into Z-scores, and compounds were ranked by combined Z-score.

Drug treatments. SMER28 was purchased from Tocris and diluted in 10 mM aliquots in DMSO. The final concentration for CD34-5F and CB CD34$^+$erythroid treatments was 0.2-10 µM as indicated in the text. The final concentration for K562 cell treatments was 20-40 µM. Ferric citrate (1-50 µM) and deferoxamine (100-200 µM) (Sigma) were dissolved in PBS and added on days 0-4 of "expansion" culture, and washed off prior to erythroid stage I (days 4-9) differentiation. For in vivo experiments, SMER28 aliquots were diluted in vehicle solution: 30% PEG-400, 5% propylene glycol, and 0.5% Tween-80. Dosing for human xenograft experiments was 2 mg/kg; for mouse models 10-20 mg/kg. Dexamethasone was purchased as Dex-sodium phosphate (DexSP) water-soluble formulation (Santa Cruz), and diluted in PBS vehicle (1 mg/kg). NSG mice were sub-lethally irradiated at 275 rads, and administered 100 µl of drug or vehicle by oral gavage daily.

Zebrafish Studies. Fish were maintained under approved laboratory conditions. The strain hi2903, an insertional mutant in the first intron of ribosomal protein s29 (rps29), the transferrin receptor 1a hypomorph, cia$^{tm25f}$, and WT AB strain were used for zebrafish studies (Amsterdam et al., 2004). For the SMER28 treatment, rps29 were incrossed and embryos were collected and treated at 50% epiboly, approximately 5 hours post fertilization (hpf). Benzidine staining was performed at 40hpf as described previously (Paffett-Lugassy and Zon, 2005). For ferric citrate and hinokitiol treatments, rps29 were incrossed and embryos were collected and treated at 24hpf. Embryos were stained with benzidine at 72hpf. For morpholino injections, the previously published atg5 and missense morpholino oligos were purchased through Gene Tools, LLC (Hu et al., 2011). The sequence for atg5 MO SEQ ID No 1; 5' CATCCTTGTCATCTGCCATTATCAT 3' and for the missense MO: SEQ ID No 2; 5' CATCGTTGTCATCTCCCATAATGAT 3'. Embryos were injected at the one cell stage with 1.6ng of MO and treated with SMER between 5-40hpf.

REFERENCES

All references cited herein, in the specification and Examples are incorporated in their entirety by reference.

Amsterdam, A., Sadler, K. C., Lai, K., Farrington, S., Bronson, R. T., Lees, J. A., and Hopkins, N. (2004). Many ribosomal protein genes are cancer genes in zebrafish. PLoS biology 2, E139.

Avior, Y., Sagi, I., and Benvenisty, N. (2016). Pluripotent stem cells in disease modelling and drug discovery. Nat Rev Mol Cell Biol 17, 170-182.

Bestebroer, J., V'Kovski, P., Mauthe, M., and Reggiori, F. (2013). Hidden behind autophagy: the unconventional roles of ATG proteins. Traffic 14, 1029-1041.

Burns C E, Galloway J L, Smith A C, et al. A genetic screen in zebrafish defines a hierarchical network of pathways required for hematopoietic stem cell emergence. Blood 2009; 113:5776-82.

Chadwick, K., Wang, L., Li, L., Menendez, P., Murdoch, B., Rouleau, A., and Bhatia, M. (2003). Cytokines and BMP-4 promote hematopoietic differentiation of human embryonic stem cells. Blood 102, 906-915.

Cheng, X., Ying, L., Lu, L., Galvao, A. M., Mills, J. A., Lin, H. C., Kotton, D. N., Shen, S. S., Nostro, M. C., Choi, J. K., et al. (2012). Self-renewing endodermal progenitor lines generated from human pluripotent stem cells. Cell Stem Cell 10, 371-384.

Chin D, Means A R. Calmodulin: a prototypical calcium sensor. Trends Cell Biol 2000; 10:322-8.

Choesmel, V., Bacqueville, D., Rouquette, J., Noaillac-Depeyre, J., Fribourg, S., Cretien, A., Leblanc, T., Tchernia, G., Da Costa, L., and Gleizes, P. E. (2007). Impaired ribosome biogenesis in Diamond-Blackfan anemia. Blood 109, 1275-1283.

Danilova N, Sakamoto K M, Lin S. Ribosomal protein L11 mutation in zebrafish leads to haematopoietic and metabolic defects. Br J Haematol 2011; 152:217-28.

Doulatov, S., and Daley, G. Q. (2013). Development. A stem cell perspective on cellular engineering. Science 342, 700-702.

Doulatov, S., Vo, L. T., Chou, S. S., Kim, P. G., Arora, N., Li, H., Hadland, B. K., Bernstein, I. D., Collins, J. J., Zon, L. I., et al. (2013). Induction of multipotential hematopoietic progenitors from human pluripotent stem cells via respecification of lineage-restricted precursors. Cell Stem Cell 13, 459-470.

Dowdle, W. E., Nyfeler, B., Nagel, J., Elling, R. A., Liu, S., Triantafellow, E., Menon, S., Wang, Z., Honda, A., Pardee, G., et al. (2014). Selective VPS34 inhibitor blocks autophagy and uncovers a role for NCOA4 in ferritin degradation and iron homeostasis in vivo. Nat Cell Biol 16, 1069-1079.

Draptchinskaia N, Gustaysson P, Andersson B, et al. The gene encoding ribosomal protein S19 is mutated in Diamond-Blackfan anaemia. Nat Genet 1999; 21:169-75.

Dutt S, Narla A, Lin K, et al. Haploinsufficiency for ribosomal protein genes causes selective activation of p53 in human erythroid progenitor cells. Blood 2011; 117:2567-76.

Ebert B L, Lee M M, Pretz J L, et al. An RNA interference model of RPS19 deficiency in Diamond-Blackfan anemia recapitulates defective hematopoiesis and rescue by dexamethasone: identification of dexamethasone-responsive genes by microarray. Blood 2005; 105:4620-6.

Ebert B L, Pretz J, Bosco J, et al. Identification of RPS14 as a 5q-syndrome gene by RNA interference screen. Nature 2008; 451:335-9.

Engle, S. J., and Vincent, F. (2014). Small molecule screening in human induced pluripotent stem cell-derived terminal cell types. J Biol Chem 289, 4562-4570.

Flygare J, Kiefer T, Miyake K, et al. Deficiency of ribosomal protein S19 in CD34+ cells generated by siRNA blocks erythroid development and mimics defects seen in Diamond-Blackfan anemia. Blood 2005; 105:4627-34.

Fumagalli S, Di Cara A, Neb-Gulati A, et al. Absence of nucleolar disruption after impairment of 40S ribosome biogenesis reveals an rpL 11-translation-dependent mechanism of p53 induction. Nat Cell Biol 2009; 11:501-8.

Galluzzi, L., Pietrocola, F., Levine, B., and Kroemer, G. (2014). Metabolic control of autophagy. Cell 159, 1263-1276.

Garcon, L., Ge, J., Manjunath, S. H., Mills, J. A., Apicella, M., Parikh, S., Sullivan, L. M., Podsakoff, G. M., Gadue, P., French, D. L., et al. (2013). Ribosomal and hematopoietic defects in induced pluripotent stem cells derived from Diamond Blackfan anemia patients. Blood.

Grskovic, M., Javaherian, A., Strulovici, B., and Daley, G. Q. (2011). Induced pluripotent stem cells-opportunities for disease modelling and drug discovery. Nat Rev Drug Discov 10, 915-929.

Heijnen, H. F., van Wijk, R., Pereboom, T. C., Goos, Y. J., Seinen, C. W., van Oirschot, B. A., van Dooren, R., Gastou, M., Giles, R. H., van Solinge, W., et al. (2014). Ribosomal protein mutations induce autophagy through S6 kinase inhibition of the insulin pathway. PLoS Genet 10, e1004371.

Heilker, R., Traub, S., Reinhardt, P., Scholer, H. R., and Sterneckert, J. (2014). iPS cell derived neuronal cells for drug discovery. Trends Pharmacol Sci 35, 510-519.

Hirose, S., Takayama, N., Nakamura, S., Nagasawa, K., Ochi, K., Hirata, S., Yamazaki, S., Yamaguchi, T., Otsu, M., Sano, S., et al. (2013). Immortalization of erythroblasts by c-MYC and BCL-XL enables large-scale erythrocyte production from human pluripotent stem cells. Stem Cell Reports 1, 499-508.

Hu, Z., Zhang, J., and Zhang, Q. (2011). Expression pattern and functions of autophagy-related gene atg5 in zebrafish organogenesis. Autophagy 7, 1514-1527.

Inagaki M, Kawamoto S, Itoh H, et al. Naphthalenesulfonamides as calmodulin antagonists and protein kinase inhibitors. Mol Pharmacol 1986; 29:577-81.

Isenberg J S, Ridnour L A, Perruccio E M, Espey M G, Wink D A, Roberts D D. Thrombospondin-1 inhibits endothelial cell responses to nitric oxide in a cGMP-dependent manner. Proc Natl Acad Sci U.S. 2005; 102:13141-6.

Jaako P, Flygare J, Olsson K, et al. Mice with ribosomal protein S19 deficiency develop bone marrow failure and symptoms like patients with Diamond-Blackfan anemia. Blood 2011; 118:6087-96.

Kang, Y. A., Sanalkumar, R., O'Geen, H., Linnemann, A. K., Chang, C. J., Bouhassira, E. E., Farnham, P. J., Keles, S., and Bresnick, E. H. (2012). Autophagy driven by a master regulator of hematopoiesis. Mol Cell Biol 32, 226-239.

Kimmey, J. M., Huynh, J. P., Weiss, L. A., Park, S., Kambal, A., Debnath, J., Virgin, H. W., and Stallings, C. L. (2015). Unique role for ATG5 in neutrophil-mediated immunopathology during *M. tuberculosis* infection. Nature 528, 565-569.

Kumano, K., Arai, S., Hosoi, M., Taoka, K., Takayama, N., Otsu, M., Nagae, G., Ueda, K., Nakazaki, K., Kamikubo, Y., et al. (2012). Generation of induced pluripotent stem cells from primary chronic myelogenous leukemia patient samples. Blood 119, 6234-6242.

Lee, H. Y., Gao, X., Barrasa, M. I., Li, H., Elmes, R. R., Peters, L. L., and Lodish, H. F. (2015). PPAR-alpha and glucocorticoid receptor synergize to promote erythroid progenitor self-renewal. Nature 522, 474-477.

Li, W., Sun, W., Zhang, Y., Wei, W., Ambasudhan, R., Xia, P., Talantova, M., Lin, T., Kim, J., Wang, X., et al. (2011). Rapid induction and long-term self-renewal of primitive neural precursors from human embryonic stem cells by small molecule inhibitors. Proc Natl Acad Sci USA 108, 8299-8304.

Lu S J, Feng Q, Park J S, et al. Biologic properties and enucleation of red blood cells from human embryonic stem cells. Blood 2008; 112:4475-84.

Mancias, J. D., Wang, X., Gygi, S. P., Harper, J. W., and Kimmelman, A. C. (2014). Quantitative proteomics identifies NCOA4 as the cargo receptor mediating ferritinophagy. Nature 509, 105-109.

Matsson, H., Davey, E. J., Draptchinskaia, N., Hamaguchi, I., Ooka, A., Leveen, P., Forsberg, E., Karlsson, S., and Dahl, N. (2004). Targeted disruption of the ribosomal protein S19 gene is lethal prior to implantation. Mol Cell Biol 24, 4032-4037.

McGowan K A, Li J Z, Park C Y, et al. Ribosomal mutations cause p53-mediated dark skin and pleiotropic effects. Nat Genet 2008; 40:963-70.

Mirabello, L., Macari, E. R., Jessop, L., Ellis, S. R., Myers, T., Giri, N., Taylor, A. M., McGrath, K. E., Humphries, J. M., Ballew, B. J., et al. (2014). Whole-exome sequencing and functional studies identify RPS29 as a novel gene mutated in multicase Diamond-Blackfan anemia families. Blood 124, 24-32.

Miyake K, Flygare J, Kiefer T, et al. Development of cellular models for ribosomal protein S19 (RPS19)-deficient diamond-blackfan anemia using inducible expression of siRNA against RPS19. Mol Ther 2005; 11:627-37.

Moniz, H., Gastou, M., Leblanc, T., Hurtaud, C., Cretien, A., Lecluse, Y., Raslova, H., Larghero, J., Croisille, L., Faubladier, M., et al. (2012). Primary hematopoietic cells from DBA patients with mutations in RPL11 and RPS19 genes exhibit distinct erythroid phenotype in vitro. Cell Death Dis 3, e356.

Mortensen, M., and Simon, A. K. (2010). Nonredundant role of Atg7 in mitochondrial clearance during erythroid development. Autophagy 6, 423-425.

Mortensen, M., Soilleux, E. J., Djordjevic, G., Tripp, R., Lutteropp, M., Sadighi-Akha, E., Stranks, A. J., Glanville, J., Knight, S., Jacobsen, S. E., et al. (2011). The autophagy protein Atg7 is essential for hematopoietic stem cell maintenance. J Exp Med 208, 455-467.

Nakamura, S., Takayama, N., Hirata, S., Seo, H., Endo, H., Ochi, K., Fujita, K., Koike, T., Harimoto, K., Dohda, T., et al. (2014). Expandable megakaryocyte cell lines enable clinically applicable generation of platelets from human induced pluripotent stem cells. Cell Stem Cell 14, 535-548.

Narla, A., and Ebert, B. L. (2010). Ribosomopathies: human disorders of ribosome dysfunction. Blood 115, 3196-3205.

Nayak, R. C., Trump, L. R., Aronow, B. J., Myers, K., Mehta, P., Kalfa, T., Wellendorf, A. M., Valencia, C. A., Paddison, P. J., Horwitz, M. S., et al. (2015). Pathogenesis of ELANE-mutant severe neutropenia revealed by induced pluripotent stem cells. J Clin Invest 125, 3103-3116.

Noh, J. Y., Gandre-Babbe, S., Wang, Y., Hayes, V., Yao, Y., Gadue, P., Sullivan, S. K., Chou, S. T., Machlus, K. R., Italiano, J. E., Jr., et al. (2015). Inducible Gata1 suppression expands megakaryocyte-erythroid progenitors from embryonic stem cells. J Clin Invest 125, 2369-2374.

North T E, Goessling W, Peeters M, et al. Hematopoietic stem cell development is dependent on blood flow. Cell 2009; 137:736-48.

North T E, Goessling W, Walkley C R, et al. Prostaglandin E2 regulates vertebrate haematopoietic stem cell homeostasis. Nature 2007; 447:1007-11.

Okita, K., Matsumura, Y., Sato, Y., Okada, A., Morizane, A., Okamoto, S., Hong, H., Nakagawa, M., Tanabe, K., Tezuka, K., et al. (2011). A more efficient method to generate integration-free human iPS cells. Nature methods 8, 409-412.

Paffett-Lugassy, N. N., and Zon, L. I. (2005). Analysis of hematopoietic development in the zebrafish. Methods in molecular medicine 105, 171-198.

Park, I. H., Zhao, R., West, J. A., Yabuuchi, A., Huo, H., Ince, T. A., Lerou, P. H., Lensch, M. W., and Daley, G. Q. (2008). Reprogramming of human somatic cells to pluripotency with defined factors. Nature 451, 141-146.

Rodriguez-Vilarrupla A, Jaumot M, Abella N, et al. Binding of calmodulin to the carboxy-terminal region of p21 induces nuclear accumulation via inhibition of protein kinase C-mediated phosphorylation of Ser153. Mol Cell Biol 2005; 25:7364-74.

Rubinsztein, D. C., Codogno, P., and Levine, B. (2012). Autophagy modulation as a potential therapeutic target for diverse diseases. Nat Rev Drug Discov 11, 709-730.

Saliba, J., Hamidi, S., Lenglet, G., Langlois, T., Yin, J., Cabagnols, X., Secardin, L., Legrand, C., Galy, A., Opolon, P., et al. (2013). Heterozygous and homozygous JAK2(V617F) states modeled by induced pluripotent stem cells from myeloproliferative neoplasm patients. PLoS One 8, e74257.

Sarkar, S., Perlstein, E. O., Imarisio, S., Pineau, S., Cordenier, A., Maglathlin, R. L., Webster, J. A., Lewis, T. A., O'Kane, C. J., Schreiber, S. L., et al. (2007). Small molecules enhance autophagy and reduce toxicity in Huntington's disease models. Nat Chem Biol 3, 331-338.

Sterneckert, J. L., Reinhardt, P., and Scholer, H. R. (2014). Investigating human disease using stem cell models. Nat Rev Genet 15, 625-639.

Sweitzer T D, Hanover J A. Calmodulin activates nuclear protein import: a link between signal transduction and nuclear transport. Proc Natl Acad Sci USA 1996; 93:14574-9.

Takagi M, Absalon M J, McLure K G, Kastan M B. Regulation of p53 translation and induction after DNA damage by ribosomal protein L26 and nucleolin. Cell 2005; 123:49-63.

Taules M, Rodriguez-Vilarrupla A, Rius E, et al. Calmodulin binds to p21(CipI) and is involved in the regulation of its nuclear localization. J Biol Chem 1999; 274:24445-8.

Taylor A M, Humphries J M, White R M, Murphey R D, Burns C E, Zon L L Hematopoietic defects in rps29 mutant zebrafish depend upon p53 activation. Exp Hematol 2012; 40:228-37 e5.

Thisse C, Thisse B. High-resolution in situ hybridization to whole-mount zebrafish embryos. Nat Protoc 2008; 3:59-69.

Tian, Y., Bustos, V., Flajolet, M., and Greengard, P. (2011). A small-molecule enhancer of autophagy decreases levels of Abeta and APP-CTF via Atg5-dependent autophagy pathway. FASEB J 25, 1934-1942.

Tulpule, A., Kelley, J. M., Lensch, M. W., McPherson, J., Park, I. H., Hartung, O., Nakamura, T., Schlaeger, T. M., Shimamura, A., and Daley, G. Q. (2013). Pluripotent stem cell models of Shwachman-Diamond syndrome reveal a common mechanism for pancreatic and hematopoietic dysfunction. Cell Stem Cell 12, 727-736.

Vlachos A, Ball S, Dahl N, et al. Diagnosing and treating Diamond Blackfan anaemia: results of an international clinical consensus conference. Br J Haematol 2008; 142: 859-76.

Vlachos A, Muir E. How I treat Diamond Blackfan anemia. Blood 2010; 116:3715-23.

Vo, L. T., and Daley, G. Q. (2015). De novo generation of HSCs from somatic and pluripotent stem cell sources. Blood 125, 2641-2648.

Warr, M. R., Binnewies, M., Flach, J., Reynaud, D., Garg, T., Malhotra, R., Debnath, J., and Passegue, E. (2013). FOXO3A directs a protective autophagy program in haematopoietic stem cells. Nature 494, 323-327.

Willig, T. N., Draptchinskaia, N., Dianzani, I., Ball, S., Niemeyer, C., Ramenghi, U., Orfali, K., Gustaysson, P., Garelli, E., Brusco, A., et al. (1999). Mutations in ribosomal protein S19 gene and diamond blackfan anemia: wide variations in phenotypic expression. Blood 94, 4294-4306.

Doulatov, S., Daley, G. Q., et al. (2017). Drug discovery for Diamond-Blackfan anemia using reprogrammed hematopoietic progenitors. Sci. Transl. Med. 8, 9 (376).

Rinderspacher, A., Landry, D. W., et al. (2009), Potent inhibitors of Huntingtin protein aggregation in a cell-based assay. Bioorg. Med. Chem. Lett. 19, 1715-1717.

SEQUENCE LISTING

CATCCTTGTC ATCTGCCATT ATCAT (SEQ ID NO: 01)

CATCGTTGTC ATCTCCCATA ATGAT (SEQ ID NO: 02)

What is claimed is:

1. A method of treating a subject with a ribosomal disorder or ribosomopathy, comprising administering to a subject having a ribosomal disorder or ribosomopathy an effective amount of a compound having structure II,

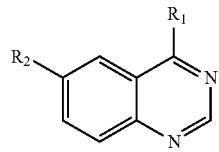

wherein
R$_1$ is —OR$_A$, —SR$_A$, —N(R$_A$)$_2$, or

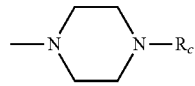

—CH$_2$CH$_2$R$_D$, wherein each occurrence of R$_A$, R$_C$, and R$_D$ are each independently a hydrogen or an aliphatic moiety;
R$_2$ is hydrogen, halogen, or OR$_B$, wherein each occurrence of R$_B$ is independently a hydrogen or an aliphatic moiety;
and pharmaceutically acceptable forms thereof, and
wherein the ribosomal disorder or ribosomopathy is selected from a group consisting of:
Diamond Blackfan anemia (DBA), inherited erythroblastopenia, 5q-syndrome, Schwachman-Diamond syndrome, dyskeratosis congenita, cartilage hair hypoplasia, Treacher Collins syndrome, Hoyeraal-Hreidarsson syndrome, and Prader-Willi syndrome.

2. The method of claim 1, wherein R$_1$ is NHR$_A$.

3. The method of claim 1, wherein R$_A$ is a C$_2$-C$_6$ alkenyl moiety.

4. The method of claim 1, wherein R$_2$ is a halogen or —OR$_B$.

5. The method of claim 1, wherein R$_1$ is —OR$_A$, R$_A$ is an allyl moiety and R$_2$ is a halogen.

6. The method of claim 1, wherein R$_1$ is —NHR$_A$, where R$_A$ is a C$_2$-C$_6$ alkenyl; and R$_2$ is a halogen.

7. The method of claim 1, wherein the ribosomal disorder or ribosomopathy is DBA or inherited erythroblastopenia and wherein R$_1$ is —NHR$_A$, R$_A$ is a C$_2$-C$_6$ alkenyl, and R$_2$ is a halogen.

8. The method of claim 1, wherein the compound is 6-Bromo-N-2-propenyl-4-quinazolinamine having Structure III (SMER28):

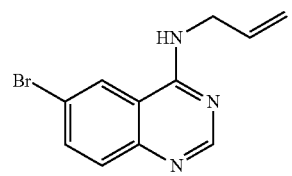

9. The method of claim 1, wherein the ribosomal disorder or ribosomopathy is DBA.

10. The method of claim 1, wherein the ribosomal disorder or ribosomopathy is DBA or inherited erythroblastopenia.

11. The method of claim 1, wherein the subject has DBA1, DBA2, DBA3, DBA4, DBA5, DBA6, DBA7, or DBA8.

12. The method of claim 1, wherein the subject has at least one mutation in ribosomal protein selected from the group consisting of: ribosomal protein S7 (RPS7), ribosomal protein S10 (RPS10), ribosomal protein S19 (RPS19), ribosomal protein 524 RPS24), ribosomal protein S26(RPS26), ribosomal protein S17 (RPS17), ribosomal protein S27L (RPS27L), ribosomal protein S29A (RPS29A), ribosomal protein L35A (RPL35A1, ribosomal protein L5 (RPL51, and ribosomal protein L11(RPL11).

13. The method of claim 1, wherein the subject has a mutation in ribosomal protein S19 (RPS19).

14. The method of claim 1, wherein the compound increases levels of hemoglobin in the subject.

15. The method of claim 1, wherein the compound increases levels of red blood cells in the subject.

16. The method of claim 1, wherein the compound induces autophagic flux in an erythroid cell or population thereof in the subject.

17. The method of claim 1, wherein the compound increases erythropoiesis in vivo or in vitro.

18. The method of claim 1, wherein the compound decreases p62 levels and increases levels of lipidated LC3-II.

19. A method for treating DBA, the method comprising; administering to a subject having DBA a therapeutically effective amount of 6-Bromo-N-2-propenyl-4-quinazolinamine (SWR28) or a pharmaceutically acceptable salt thereof.

20. The method of claim 19, wherein the subject has a mutation in ribosomal protein S19 RPS19.

21. A method for increasing rate of red blood cell (RBC) differentiation, the method comprising: contacting an erythroblast or a population thereof at stages I-III of differentiation with SMER28.

* * * * *

UNITED STATES PATENT AND TRADEMARK OFFICE
CERTIFICATE OF CORRECTION

Page 1 of 2

PATENT NO. : 11,980,620 B2
APPLICATION NO. : 16/620064
DATED : May 14, 2024
INVENTOR(S) : Sergei Doulatov et al.

It is certified that error appears in the above-identified patent and that said Letters Patent is hereby corrected as shown below:

In the Claims

In Claim 1, at Column 67, Lines 6-14, please replace:

"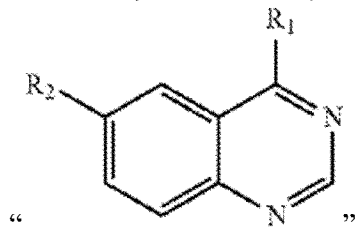"

With:

-- 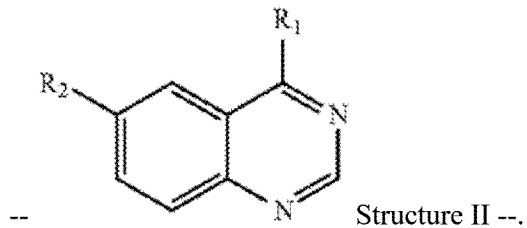 Structure II --.

In Claim 1, at Column 67, Lines 16-23, please replace:

"$R_1$ is -$OR_A$, -$SR_A$, -$N(R_A)_2$, or ⟨piperazine-$R_C$⟩ -$CH_2CH_2R_D$"

With:

-- $R_1$ is -$OR_A$, -$SR_A$, -$N(R_A)_2$, ⟨piperazine-$R_C$⟩, or -$CH_2CH_2R_D$ --.

Signed and Sealed this
Eleventh Day of February, 2025

Coke Morgan Stewart
*Acting Director of the United States Patent and Trademark Office*

CERTIFICATE OF CORRECTION (continued)
U.S. Pat. No. 11,980,620 B2

In Claim 1, at Column 67, Line 31, please replace:
"selected from a group consisting of"
With:
-- selected from the group consisting of --.

In Claim 12, at Column 68, Line 22, please replace:
"524 RPS24)"
With:
-- S24 (RPS24) --.

In Claim 12, at Column 68, Line 22, please replace:
"S26(RPS26)"
With:
-- S26 (RPS26) --.

In Claim 12, at Column 68, Line 25, please replace:
"(RPL35A1"
With:
-- (RPL35A) --.

In Claim 12, at Column 68, Line 25, please replace:
"(RPL51"
With:
-- (RPL5) --.

In Claim 19, at Column 68, Line 44, please replace:
"(SWR28)"
With:
-- (SMER28) --.

In Claim 20, Column 68, Line 47, please replace:
"RPS19"
With:
-- (RPS19) --.

SEQUENCE LISTING

```
<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Morpholino oligonucleotide sequence

<400> SEQUENCE: 1
catccttgtc atctgccatt atcat                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Morpholino oligonucleotide sequence

<400> SEQUENCE: 2
catcgttgtc atctcccata atgat                                          25

<210> SEQ ID NO 3
<211> LENGTH: 15
<212> TYPE: DNA
<213> ORGANISM: Homo sapiens
<220> FEATURE:
```

```
<221> NAME/KEY: CDS
<222> LOCATION: (1)..(15)

<400> SEQUENCE: 3 ttc agc cga ggc tcc                                              15
Phe Ser Arg Gly Ser
1               5

<210> SEQ ID NO 4
<211> LENGTH: 5
<212> TYPE: PRT
<213> ORGANISM: Homo sapiens

<400> SEQUENCE: 4

Phe Ser Arg Gly Ser
1               5

<210> SEQ ID NO 5
<211> LENGTH: 15
<212> TYPE: DNA
<213> ORGANISM: Homo sapiens

<400> SEQUENCE: 5
ttcagctgag gctcc                                                 15

<210> SEQ ID NO 6
<211> LENGTH: 12
<212> TYPE: DNA
<213> ORGANISM: Homo sapiens
<220> FEATURE:
<221> NAME/KEY: CDS
<222> LOCATION: (1)..(12)

<400> SEQUENCE: 6 aag aga tac caa                                                  12
Lys Arg Tyr Gln
1

<210> SEQ ID NO 7
<211> LENGTH: 4
<212> TYPE: PRT
<213> ORGANISM: Homo sapiens

<400> SEQUENCE: 7

Lys Arg Tyr Gln
1

<210> SEQ ID NO 8
<211> LENGTH: 12
<212> TYPE: DNA
<213> ORGANISM: Homo sapiens

<400> SEQUENCE: 8
aagagatamc aa                                                    12
```